US012559710B2

(12) United States Patent
Azersky et al.

(10) Patent No.: US 12,559,710 B2
(45) Date of Patent: Feb. 24, 2026

(54) LIQUID LEVEL AND FLOW RATE DETECTION WITHIN A CELL PROCESSING SYSTEM

(71) Applicant: Cellares Corporation, South San Francisco, CA (US)

(72) Inventors: Vladimir Azersky, San Jose, CA (US); David Freiberger, San Francisco, CA (US); Caitlin A. Regan, San Mateo, CA (US); Wilson Wai Toy, San Francisco, CA (US); Matthias Weber, South San Francisco, CA (US); Yiming Xu, San Mateo, CA (US)

(73) Assignee: Cellares Corporation, South San Francisco, CA (US)

( * ) Notice: Subject to any disclaimer, the term of this patent is extended or adjusted under 35 U.S.C. 154(b) by 0 days.

(21) Appl. No.: 19/091,700

(22) Filed: Mar. 26, 2025

(65) Prior Publication Data

US 2025/0304904 A1      Oct. 2, 2025

Related U.S. Application Data

(60) Provisional application No. 63/570,739, filed on Mar. 27, 2024.

(51) Int. Cl.
| | |
|---|---|
| *C12M 1/36* | (2006.01) |
| *C12M 1/34* | (2006.01) |
| *C12M 3/00* | (2006.01) |
| *G01F 23/02* | (2006.01) |

(52) U.S. Cl.
CPC ............ *C12M 41/48* (2013.01); *C12M 23/44* (2013.01); *C12M 41/44* (2013.01); *G01F 23/02* (2013.01)

(58) Field of Classification Search
None
See application file for complete search history.

(56) References Cited

U.S. PATENT DOCUMENTS

| | | |
|---|---|---|
| 3,728,227 A | 4/1973 | Elson et al. |
| 4,234,023 A | 11/1980 | Sogi et al. |
| 4,696,902 A | 9/1987 | Bisconte |
| 4,839,292 A | 6/1989 | Cremonese |
| 4,911,833 A | 3/1990 | Schoendorfer et al. |
| 5,058,619 A | 10/1991 | Zheng |
| 5,656,491 A | 8/1997 | Cassani et al. |
| 6,102,678 A | 8/2000 | Peclat |
| 6,267,559 B1 | 7/2001 | Mossman et al. |
| 6,649,419 B1 | 11/2003 | Anderson |
| 7,550,287 B2 | 6/2009 | Hibino et al. |
| 7,745,209 B2 | 6/2010 | Martin et al. |
| 7,816,128 B2 | 10/2010 | Nakashima et al. |
| 8,158,426 B2 | 4/2012 | Wilson et al. |
| 8,158,427 B2 | 4/2012 | Wilson et al. |
| 8,168,432 B2 | 5/2012 | Wilson et al. |

| | | |
|---|---|---|
| 8,273,572 B2 | 9/2012 | Martin et al. |
| 8,415,144 B2 | 4/2013 | Wilson et al. |
| 8,440,458 B2 | 5/2013 | Zijlstra et al. |
| 8,470,589 B2 | 6/2013 | Martin et al. |
| 8,492,140 B2 | 7/2013 | Smith et al. |
| 8,546,142 B2 | 10/2013 | Martin et al. |
| 8,697,443 B2 | 4/2014 | Wilson et al. |
| 8,727,132 B2 | 5/2014 | Miltenyi et al. |
| 8,809,044 B2 | 8/2014 | Wilson |
| 8,846,399 B2 | 9/2014 | Martin et al. |
| 8,956,860 B2 | 2/2015 | Vera et al. |
| 9,040,290 B2 | 5/2015 | Martin et al. |
| 9,045,721 B2 | 6/2015 | Martin et al. |
| 9,080,149 B2 | 7/2015 | Bosio et al. |
| 9,255,243 B2 | 2/2016 | Wilson et al. |
| 9,279,099 B2 | 3/2016 | Okano et al. |
| 9,290,730 B2 | 3/2016 | Martin et al. |
| 9,410,114 B2 | 8/2016 | Wilson et al. |
| 9,441,192 B2 | 9/2016 | Wilson et al. |
| 9,499,780 B2 | 11/2016 | Smith et al. |
| 9,534,195 B2 | 1/2017 | Smith et al. |
| 9,556,485 B2 | 1/2017 | Lin et al. |
| 9,567,565 B2 | 2/2017 | Vera et al. |

(Continued)

FOREIGN PATENT DOCUMENTS

| | | |
|---|---|---|
| CN | 104203333 A | 12/2014 |
| CN | 108660060 A | 10/2018 |

(Continued)

OTHER PUBLICATIONS

Shabalina et al. ("ARTag, AprilTag and CALTag Fiducial Systems Comparison in a Presence of Partial Rotation: Manual and Automated Approaches" in ICINCO (2017) LNEE 495:536-558 92019), Springer Nature Switzerland).*
ChargePoint (2021). Aseptic split butterfly valve 10-6 sterility assurance, located at https://www.thechargepoint.com/products/aseptic-split-butterfly-valve-10-6-sterility-assurance/, 2 total pages.
CPC (2014). "6 traits of non-spill: How quick disconnect couplings evolved for low-pressure fluid handling," White Paper 8004, 4 total pages.
CPC (2014). "How single-use connections advance aseptic processing: Increased process flexibility and reliability, reduced costs," White Paper 7004, 6 total pages.
CPC (2018). Comparison Guide: Tube Welders and Aseptic Connectors, Technical Guide 7009, 3 total pages.
EMD Millipore (2015). "Lynx® S2S Connector—Low temperature compatibility (−80 C)," 4 total pages.

(Continued)

*Primary Examiner* — Lori A. Clow
(74) *Attorney, Agent, or Firm* — Cooley LLP

(57)      ABSTRACT

The present disclosure relates to systems and methods for monitoring liquid levels within cartridges of automated cell processing systems during cell processing. A method for automated cell processing may first include coupling a cell processing cartridge to an instrument configured to perform a cell processing operation with at least one module of the cartridge. Next, the method may include detecting, via a vision system of the instrument, a liquid level of a liquid within one or more cell processing modules of the cartridge. Finally, the method may include determining a volume of the liquid based on the liquid level.

22 Claims, 23 Drawing Sheets

(56) References Cited

U.S. PATENT DOCUMENTS

| | | | |
|---|---|---|---|
| 9,597,355 | B2 | 3/2017 | Magnant |
| 9,625,463 | B2 | 4/2017 | Miltenyi et al. |
| 9,701,932 | B2 | 7/2017 | Smith et al. |
| 9,732,317 | B2 | 8/2017 | Wilson |
| 9,783,768 | B2 | 10/2017 | Larcher et al. |
| 9,845,451 | B2 | 12/2017 | Martin et al. |
| 10,047,342 | B2 | 8/2018 | Eibl et al. |
| 10,053,663 | B2 | 8/2018 | Kabaha et al. |
| 10,119,970 | B2 | 11/2018 | Miltenyi et al. |
| 10,131,876 | B2 | 11/2018 | Kaiser et al. |
| 10,253,316 | B2 | 4/2019 | Masquelier et al. |
| 10,294,658 | B2 | 5/2019 | Scannon et al. |
| 10,323,258 | B2 | 6/2019 | Bernate et al. |
| 10,329,559 | B1 | 6/2019 | Masquelier et al. |
| 10,385,307 | B2 | 8/2019 | Rowley et al. |
| 10,421,959 | B1 | 9/2019 | Masquelier et al. |
| 10,508,288 | B1 | 12/2019 | Bernate et al. |
| 10,519,437 | B1 | 12/2019 | Masquelier et al. |
| 10,533,156 | B2 | 1/2020 | Vera et al. |
| 10,584,333 | B1 | 3/2020 | Masquelier et al. |
| 10,584,334 | B1 | 3/2020 | Masquelier et al. |
| 10,588,994 | B2 | 3/2020 | Kawamura et al. |
| 10,620,212 | B2 | 4/2020 | Miltenyi et al. |
| 10,689,669 | B1 | 6/2020 | Feldman et al. |
| 10,705,090 | B2 | 7/2020 | Miltenyi et al. |
| 10,705,091 | B2 | 7/2020 | Miltenyi et al. |
| 10,723,986 | B2 | 7/2020 | Smith et al. |
| 10,724,043 | B2 | 7/2020 | Sixto et al. |
| 10,844,338 | B1 | 11/2020 | Smith et al. |
| 11,161,111 | B2 | 11/2021 | Kabaha et al. |
| 11,198,845 | B2 | 12/2021 | Parietti et al. |
| 11,371,018 | B2 | 6/2022 | Shi et al. |
| 11,376,587 | B2 | 7/2022 | Thakkar et al. |
| 11,447,745 | B2 | 9/2022 | Shi et al. |
| 11,701,654 | B2 | 7/2023 | Azersky et al. |
| 11,786,896 | B2 | 10/2023 | Thakkar et al. |
| 11,826,756 | B2 | 11/2023 | Azersky et al. |
| 11,872,557 | B2 | 1/2024 | Biz et al. |
| 12,157,119 | B2 | 12/2024 | Gerlinghaus et al. |
| 12,180,453 | B2 | 12/2024 | Chang et al. |
| 12,305,156 | B2 | 5/2025 | Burkeen et al. |
| 12,337,321 | B2 | 6/2025 | Malleo et al. |
| 12,350,664 | B2 | 7/2025 | Pesch et al. |
| 12,350,667 | B2 | 7/2025 | Azersky et al. |
| 12,350,668 | B2 | 7/2025 | Azersky et al. |
| 12,399,193 | B2 | 8/2025 | Tian et al. |
| 12,403,468 | B2 | 9/2025 | Azersky et al. |
| 2003/0030272 | A1 | 2/2003 | Johnson et al. |
| 2005/0260743 | A1 | 11/2005 | Drake et al. |
| 2006/0194193 | A1 | 8/2006 | Tsuruta et al. |
| 2006/0257999 | A1 | 11/2006 | Chang et al. |
| 2007/0185472 | A1 | 8/2007 | Baumfalk et al. |
| 2008/0057568 | A1 | 3/2008 | Kan et al. |
| 2008/0176318 | A1 | 7/2008 | Wilson et al. |
| 2009/0042281 | A1 | 2/2009 | Chang et al. |
| 2009/0247417 | A1 | 10/2009 | Haas et al. |
| 2010/0172045 | A1* | 7/2010 | Goodman .......... G11B 15/6835 |
| 2010/0301071 | A1 | 12/2010 | Alstad et al. |
| 2011/0003380 | A1 | 1/2011 | Miltenyi et al. |
| 2012/0138156 | A1 | 6/2012 | Hofman et al. |
| 2012/0148415 | A1 | 6/2012 | Brueckner |
| 2013/0115617 | A1 | 5/2013 | Wilson |
| 2013/0189120 | A1 | 7/2013 | Nelson et al. |
| 2014/0309795 | A1 | 10/2014 | Norton et al. |
| 2015/0307829 | A1 | 10/2015 | Dedry et al. |
| 2016/0208216 | A1 | 7/2016 | Vera et al. |
| 2016/0303563 | A1 | 10/2016 | Granier et al. |
| 2016/0320381 | A1 | 11/2016 | Holmes et al. |
| 2016/0320422 | A1 | 11/2016 | Fritchie et al. |
| 2017/0014149 | A1 | 1/2017 | Nakayashiki et al. |
| 2017/0058527 | A1 | 3/2017 | Williams et al. |
| 2017/0239420 | A1 | 8/2017 | Wells |
| 2017/0248697 | A1 | 8/2017 | Lo |
| 2017/0307502 | A1 | 10/2017 | Mason et al. |
| 2017/0313977 | A1 | 11/2017 | Wilson |

| | | | |
|---|---|---|---|
| 2017/0321226 | A1 | 11/2017 | Gill et al. |
| 2017/0362554 | A1 | 12/2017 | Martin et al. |
| 2018/0031592 | A1 | 2/2018 | Dority |
| 2018/0051243 | A1 | 2/2018 | Hogan et al. |
| 2018/0078935 | A1 | 3/2018 | Hung et al. |
| 2018/0185849 | A1 | 7/2018 | Kaplan et al. |
| 2018/0196918 | A1 | 7/2018 | Sadowski et al. |
| 2019/0212233 | A1 | 7/2019 | Jovanovich et al. |
| 2019/0275519 | A1 | 9/2019 | Castillo et al. |
| 2019/0292510 | A1 | 9/2019 | Tandon et al. |
| 2019/0316120 | A1 | 10/2019 | Masquelier et al. |
| 2020/0009557 | A1 | 1/2020 | Frigard et al. |
| 2020/0025782 | A1 | 1/2020 | Ahlfors |
| 2020/0095550 | A1 | 3/2020 | Vera et al. |
| 2020/0132534 | A1 | 4/2020 | Luedemann |
| 2020/0159198 | A1 | 5/2020 | Kapre et al. |
| 2020/0283713 | A1 | 9/2020 | Ball et al. |
| 2020/0292552 | A1 | 9/2020 | Miltenyi et al. |
| 2020/0353004 | A1 | 11/2020 | Nowak et al. |
| 2020/0368411 | A1 | 11/2020 | Camisani et al. |
| 2020/0406221 | A1 | 12/2020 | Dabrowski et al. |
| 2021/0032583 | A1 | 2/2021 | Smith et al. |
| 2021/0035655 | A1 | 2/2021 | Tanouchi et al. |
| 2021/0047668 | A1 | 2/2021 | Dabrowski et al. |
| 2021/0079344 | A1 | 3/2021 | Bosio et al. |
| 2021/0147807 | A1 | 5/2021 | Lickert et al. |
| 2021/0253997 | A1 | 8/2021 | Wilson |
| 2021/0269755 | A1 | 9/2021 | Smith et al. |
| 2021/0283565 | A1 | 9/2021 | Gerlinghaus et al. |
| 2021/0283606 | A1 | 9/2021 | Thakkar et al. |
| 2021/0301239 | A1 | 9/2021 | Natsume et al. |
| 2021/0324318 | A1 | 10/2021 | Parietti et al. |
| 2021/0354104 | A1 | 11/2021 | Pesch et al. |
| 2022/0002652 | A1 | 1/2022 | Patrick et al. |
| 2022/0127558 | A1 | 4/2022 | Sowwan et al. |
| 2022/0143610 | A1 | 5/2022 | Biz et al. |
| 2022/0150650 | A1 | 5/2022 | Rucker |
| 2022/0163438 | A1 | 5/2022 | Klas et al. |
| 2022/0282199 | A1 | 9/2022 | Vann |
| 2022/0284574 | A1* | 9/2022 | Wagner .................. C12M 23/42 |
| 2022/0325219 | A1 | 10/2022 | Parietti et al. |
| 2022/0347683 | A1 | 11/2022 | Thakkar et al. |
| 2023/0044320 | A1 | 2/2023 | Chalony et al. |
| 2023/0149922 | A1 | 5/2023 | Thakkar et al. |
| 2023/0159917 | A1 | 5/2023 | Handique et al. |
| 2023/0321650 | A1 | 10/2023 | Azersky et al. |
| 2023/0415154 | A1 | 12/2023 | Pesch et al. |
| 2023/0415155 | A1 | 12/2023 | Biz et al. |
| 2024/0018955 | A1 | 1/2024 | Hannah et al. |
| 2024/0165613 | A1 | 5/2024 | Azersky et al. |
| 2024/0167466 | A1 | 5/2024 | Paraluppi |
| 2024/0240764 | A1 | 7/2024 | Gabrielli et al. |
| 2024/0254426 | A1 | 8/2024 | Elpel et al. |
| 2024/0255537 | A1 | 8/2024 | Malleo et al. |
| 2024/0279585 | A1 | 8/2024 | Griffin et al. |
| 2024/0279588 | A1 | 8/2024 | Malleo et al. |
| 2024/0318116 | A1 | 9/2024 | Chang et al. |
| 2024/0326043 | A1 | 10/2024 | Gerlinghaus et al. |
| 2024/0369586 | A1 | 11/2024 | Tian et al. |
| 2024/0377420 | A1 | 11/2024 | Cesarek |
| 2024/0390897 | A1 | 11/2024 | Azersky et al. |
| 2024/0390898 | A1 | 11/2024 | Azersky et al. |
| 2024/0399365 | A1 | 12/2024 | Biz et al. |
| 2024/0402206 | A1 | 12/2024 | Boppart et al. |
| 2025/0002837 | A1 | 1/2025 | Bharat |
| 2025/0059492 | A1 | 2/2025 | Beban et al. |
| 2025/0065331 | A1 | 2/2025 | Malleo et al. |
| 2025/0066708 | A1 | 2/2025 | Burkeen et al. |
| 2025/0066709 | A1 | 2/2025 | Grout et al. |
| 2025/0129321 | A1 | 4/2025 | Malleo et al. |
| 2025/0207076 | A1 | 6/2025 | Marchiando et al. |
| 2025/0236832 | A1 | 7/2025 | Chang et al. |
| 2025/0283026 | A1 | 9/2025 | Carmichael et al. |

FOREIGN PATENT DOCUMENTS

| | | | |
|---|---|---|---|
| EP | 0246912 | A2 | 11/1987 |
| EP | 0991389 | A1 | 4/2000 |
| EP | 0824380 | B1 | 1/2002 |

(56) References Cited

FOREIGN PATENT DOCUMENTS

| | | | |
|---|---|---|---|
| EP | 3134512 B1 | 1/2019 | |
| EP | 2809449 B1 | 10/2019 | |
| EP | 3359294 B1 | 5/2020 | |
| EP | 3928867 A1 | 12/2021 | |
| GB | 2268187 A | 1/1994 | |
| JP | 2007325586 A | 12/2007 | |
| KR | 20130018286 A | 2/2013 | |
| WO | WO-2006102416 A2 | 9/2006 | |
| WO | WO-2006112870 A1 | 10/2006 | |
| WO | WO-2006118282 A1 | 11/2006 | |
| WO | WO-2007139742 A1 | 12/2007 | |
| WO | WO-2009072003 A2 | 6/2009 | |
| WO | WO-2017041051 A1 | 3/2017 | |
| WO | WO-2017123663 A1 | 7/2017 | |
| WO | WO-2018015561 A1 | 1/2018 | |
| WO | WO-2018102471 A1 | 6/2018 | |
| WO | WO-2019232504 A2 | 12/2019 | |
| WO | WO-2020009700 A1 | 1/2020 | |
| WO | WO-2020014264 A1 | 1/2020 | |
| WO | WO-2021168368 A1 | 8/2021 | |
| WO | WO-2021183687 A2 | 9/2021 | |
| WO | WO-2021212124 A1 | 10/2021 | |
| WO | WO-2024112702 A1 | 5/2024 | |
| WO | WO-2024206703 A1 | 10/2024 | |
| WO | WO-2025007051 A2 | 1/2025 | |
| WO | WO-2025038974 A1 | 2/2025 | |
| WO | WO-2025041046 A1 | 2/2025 | |
| WO | WO-2025202944 A2 | 10/2025 | |

OTHER PUBLICATIONS

Final Office Action for U.S. Appl. No. 17/331,554 mailed Aug. 29, 2024, 18 pages.
Final Office Action for U.S. Appl. No. 18/799,963 mailed Jan. 30, 2025, 10 pages.
Final Office Action mailed on Apr. 28, 2022, for U.S. Appl. No. 17/198,134, filed Mar. 10, 2021, 11 pages.
Final Office Action mailed on Apr. 28, 2022, for U.S. Appl. No. 17/331,554, filed May 26, 2021, 16 pages.
Final Office Action mailed on Jul. 31, 2023, for U.S. Appl. No. 17/331,554, filed May 26, 2021, 19 pages.
Final Office Action mailed on Mar. 31, 2023, for U.S. Appl. No. 17/579,478, filed Jan. 19, 2022, 8 pages.
Garcia et al., "Microfluidic Screening of Electric Fields for Electroporation" Sci Rep. Feb. 19, 2016; 6:21238. pp. 1-11.
Genetic Engineering & Biotechnology News (2006). "Thermal welding for sterile connections," located at https://www.genengnews.com/magazine/47/thermal-welding-for-sterile-connections/, 5 total pages.
International Search Report and Written Opinion for PCT Application No. PCT/IB2024/058105 mailed Dec. 16, 2024, 12 pages.
International Search Report and Written Opinion for PCT Application No. PCT/US2024/022079 mailed Sep. 12, 2024, 25 pages.
International Search Report and Written Opinion for PCT Application No. PCT/US2024/042795 mailed Dec. 16, 2024, 11 pages.
International Search Report mailed on Oct. 13, 2021, for PCT Application No. PCT/US2021/021773, filed on Mar. 10, 2021, 13 pages.
Invitation to Pay Additional Fees for International Application No. PCT/US2024/022079 dated Jul. 17, 2024, 19 pages.
Jain, S. et al. (2011). "The complete automation of cell culture: improvements for high-throughput and high-content screening," J. Biomol. Screen 16:932-939.
Kato, R. et al. (2010). "A Compact, Automated Cell Culture System for Clinical Scale Cell Expansion from Primary Tissues," Tissue Engineering: Part C 16:947-956.
Kempner, M.E. and Felder, R.A., "A review of cell culture automation". JALA: Journal of the Association for Laboratory Automation (Apr. 2002); 7(2): 56-62.

Kino-Oka, M. et al. (2005). "Bioreactor Design for Successive Culture of Anchorage-Dependent Cells Operated in an Automated Manner," Tissue Engineering 11:535-545.
Knoll, A. et al. (2004). "Flexible automation of cell culture and tissue engineering tasks," Biotechnol. Prog. 20:1825-1835.
Lutkemeyer, D. et al. (2000). "First steps in robot automation of sampling and sample management during cultivation of mammalian cells in pilot scale," Biotechnol. Prog. 16:822-828.
MEDInstill (2021). INTACT™ Connectors, located at https://www.medinstill.com/intactconnectors.php, 1 total page.
Millipore® (2020). "Technical Brief—Choosing the right sterile connector based on design and sterility test results," 4 total pages.
Millipore Sigma (2020). "Lynx® CDR Connectors," Datasheet, 4 total pages.
Millipore Sigma (2021). Lynx® CDR Connectors, located at https://www.emdmillipore.com/US/en/product/Lynx-CDR-Connectors,MM_NF-C188801, 2 total pages.
Non-Final Office Action for U.S. Appl. No. 18/244,051 mailed Oct. 9, 2024, 10 pages.
Non-Final Office Action for U.S. Appl. No. 18/759,602 mailed Feb. 20, 2025, 15 pages.
Non-Final Office Action for U.S. Appl. No. 18/759,602 mailed Nov. 8, 2024, 10 pages.
Non-Final Office Action for U.S. Appl. No. 18/792,358 mailed on Nov. 6, 2024, 5 pages.
Non-Final Office Action for U.S. Appl. No. 18/799,963 mailed Sep. 30, 2024, 9 pages.
Non-Final Office action for U.S. Appl. No. 18/920,607 mailed Feb. 28, 2025, 10 pages.
Non-Final Office Action mailed on Apr. 24, 2024, for U.S. Appl. No. 17/331,554, filed May 26, 2021, 17 pages.
Non-Final Office Action mailed on Dec. 22, 2022, for U.S. Appl. No. 17/579,478, filed Jan. 19, 2022, 8 pages.
Non-Final Office Action mailed on Dec. 3, 2021, for U.S. Appl. No. 17/331,556, filed May 26, 2021, 9 pages.
Non-Final Office Action mailed on Feb. 3, 2022, for U.S. Appl. No. 17/198,134, filed Mar. 10, 2021, 5 pages.
Non-Final Office Action mailed on Jun. 26, 2023, for U.S. Appl. No. 17/198,134, filed Mar. 10, 2021, 15 pages.
Non-Final Office Action mailed on Mar. 16, 2023, for U.S. Appl. No. 17/331,554, filed May 26, 2021, 16 pages.
Non-Final Office Action mailed on Oct. 28, 2021, for U.S. Appl. No. 17/331,554, filed May 26, 2021, 11 pages.
Non-Final Office Action mailed on Oct. 6, 2021, for U.S. Appl. No. 17/198,134, filed Mar. 10, 2021, 7 pages.
Non-Final Office Action mailed on Sep. 13, 2023, for U.S. Appl. No. 18/141,329, filed Apr. 28, 2023, 7 pages.
Notice of Allowance for U.S. Appl. No. 17/331,554 mailed Mar. 5, 2025, 8 pages.
Notice of Allowance for U.S. Appl. No. 18/487,884 mailed Feb. 26, 2025, 8 pages.
Notice of Allowance for U.S. Appl. No. 18/792,358 mailed on Mar. 3, 2025, 8 pages.
Notice of Allowance for U.S. Appl. No. 18/792,360 mailed Mar. 4, 2025, 9 pages.
Notice of Allowance for U.S. Appl. No. 18/792,360 mailed on Jan. 29, 2025, 9 pages.
Notice of Allowance for U.S. Appl. No. 18/810,388 mailed Jan. 21, 2025, 8 pages.
Notice of Allowance for U.S. Appl. No. 18/810,388 mailed on Oct. 9, 2024, 9 pages.
Notice of Allowance mailed on Apr. 11, 2024, for U.S. Appl. No. 17/198,134, filed Mar. 10, 2021, 9 pages.
Notice of Allowance mailed on Jul. 18, 2023, for U.S. Appl. No. 17/849,422, filed Jun. 24, 2022, 8 pages.
Notice of Allowance mailed on Jul. 25, 2023, for U.S. Appl. No. 17/579,478, filed Jan. 19, 2022, 8 pages.
Notice of Allowance mailed on Jun. 8, 2023, for U.S. Appl. No. 17/849,422, filed Jun. 24, 2022, 8 pages.
Notice of Allowance mailed on Mar. 1, 2022, for U.S. Appl. No. 17/331,556, filed May 26, 2021, 8 pages.
Notice of Allowance mailed on Mar. 22, 2023, for U.S. Appl. No. 17/992,784, filed Nov. 22, 2022, 8 pages.

(56) References Cited

OTHER PUBLICATIONS

Notice of Allowance mailed on Oct. 4, 2023, for U.S. Appl. No. 18/141,329, filed Apr. 28, 2023, 8 pages.

Pharma Japan, "Astellas Set to Cut Development Time with Cell Culture Robot, Eyes 4 Billion Yen Profit per Product" Aug. 9, 2023, 3 pages.

Qu, B. et al., "Droplet Electroporation in Microfluidics for Efficient Cell Transformation with or without Cell Wall Removal," Lab Chip (2012) 12:4483-4488.

Saint Gobain (2017). "Pure-Fit® SC—Secure aseptic connections," Brochure, 5 total pages.

Sartorius Stedim Biotech (2011). "Opta® SFT," 4 total pages.

Schwartz C., "Optimizing Cell Separation with Beckman Coulter's Centrifugal Elutriation System," Beckmann Coulter Life Sciences (2014) 6 total pages.

SeriesLock™ (2021). Features and Specifications, located at https://serieslock.com/, 5 total pages.

Shi, Y. et al. (1992). "Performance of Mammalian Cell Culture Bioreactor with a New Impeller Design," Biotechnology and Bioengineering 40:260-270.

Steris (2018). "A compilation of material compatibilities with vaporized hydrogen peroxide," 2 total pages.

Steris (2018). "Sterility assurance levels (SALS): Irradiation," 3 total pages.

Steris (2020). "Overview of sterilization technology comparison," 1 total page.

Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.

U.S. Appl. No. 18/988,628, filed Dec. 19, 2024, by Marchiando et al.

U.S. Appl. No. 29/898,923, filed Aug. 2, 2023, by Gerlinghaus et al.

Written Opinion of the International Searching Authority mailed on Oct. 13, 2021, for PCT Application No. PCT/US2021/021773, filed on Mar. 10, 2021, 20 pages.

Final Office Action for U.S. Appl. No. 18/244,051 mailed Apr. 4, 2025, 11 pages.

Final Office Action for U.S. Appl. No. 18/759,602 mailed on May 28, 2025, 12 pages.

Final Office Action for U.S. Appl. No. 18/807,699 mailed on Aug. 20, 2025, 22 pages.

Final Office Action for U.S. Appl. No. 18/920,607 mailed Jun. 4, 2025, 10 pages.

International Search Report and Written Opinion for PCT Application No. PCT/US2024/036245 mailed Jun. 11, 2025, 13 pages.

Non-Final Office Action for U.S. Appl. No. 18/807,699 mailed Apr. 29, 2025, 19 pages.

Notice of Allowance for U.S. Appl. No. 17/331,554 mailed Apr. 10, 2025, 6 pages.

Notice of Allowance for U.S. Appl. No. 18/487,884 mailed on Apr. 3, 2025, 8 pages.

Notice of Allowance for U.S. Appl. No. 18/799,963 mailed Jul. 1, 2025, 7 pages.

Notice of Allowance for U.S. Appl. No. 18/810,388 mailed Apr. 30, 2025, 5 pages.

Notice of Allowance for U.S. Appl. No. 19/075,709 mailed Jul. 29, 2025, 10 pages.

* cited by examiner

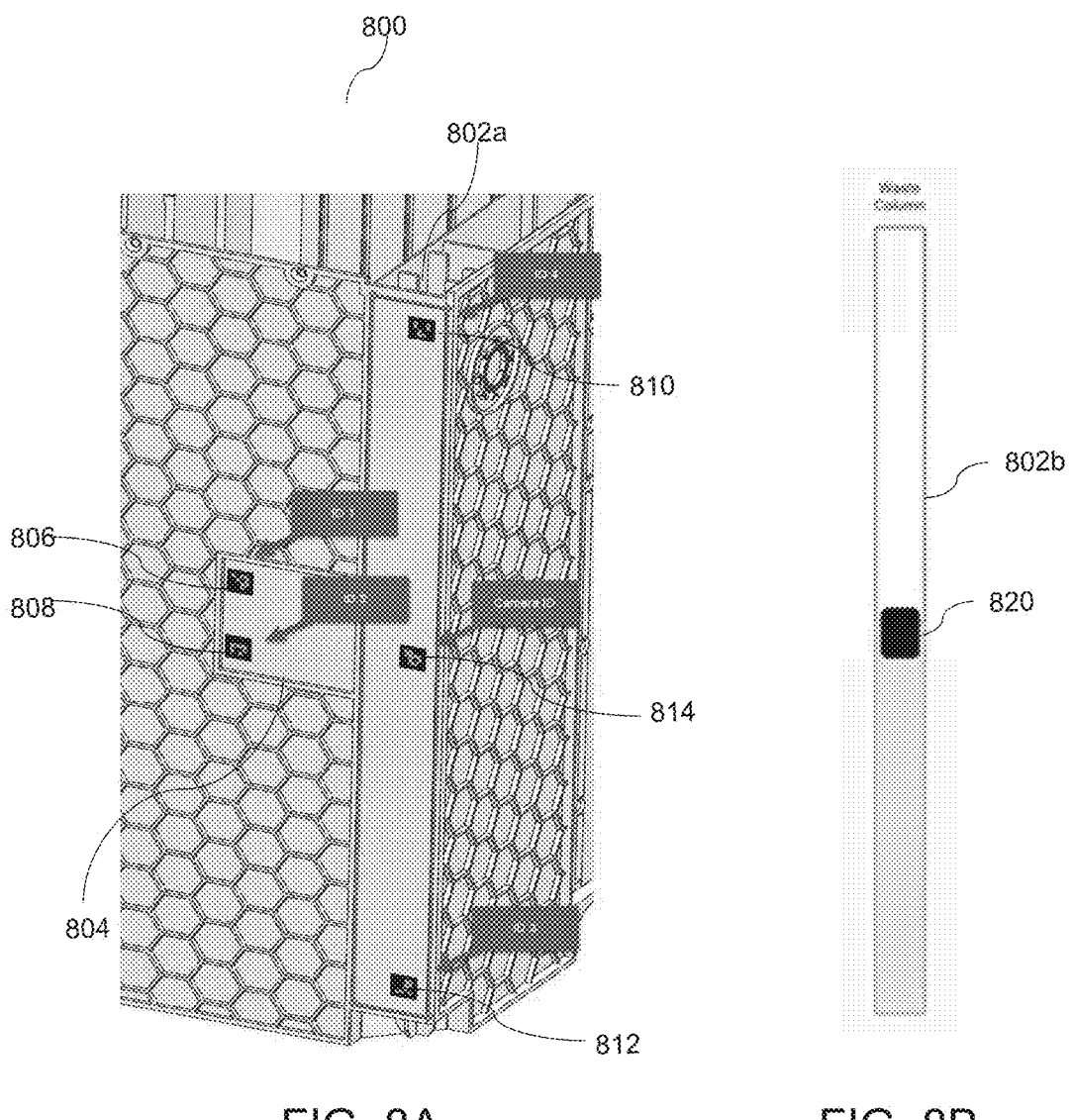
FIG. 8A                    FIG. 8B

1100

1500

Couple a calibration cartridge to a cell processing instrument
1502

Detect a location of one or more fiducial markers of the
cartridge using vision system of the instrument 1504

Generate a calibration result using the detected locations 1506

Figure 16:
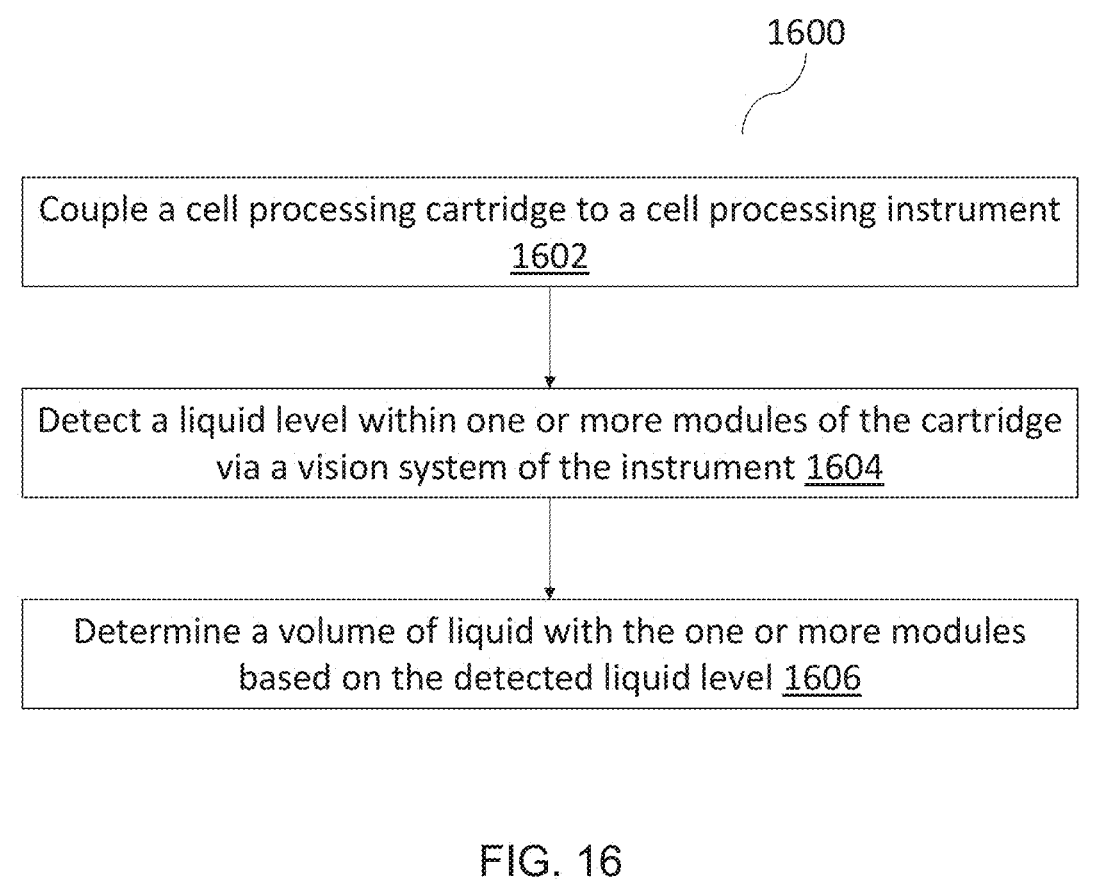

1600

Couple a cell processing cartridge to a cell processing instrument
1602

Detect a liquid level within one or more modules of the cartridge
via a vision system of the instrument 1604

Determine a volume of liquid with the one or more modules
based on the detected liquid level 1606

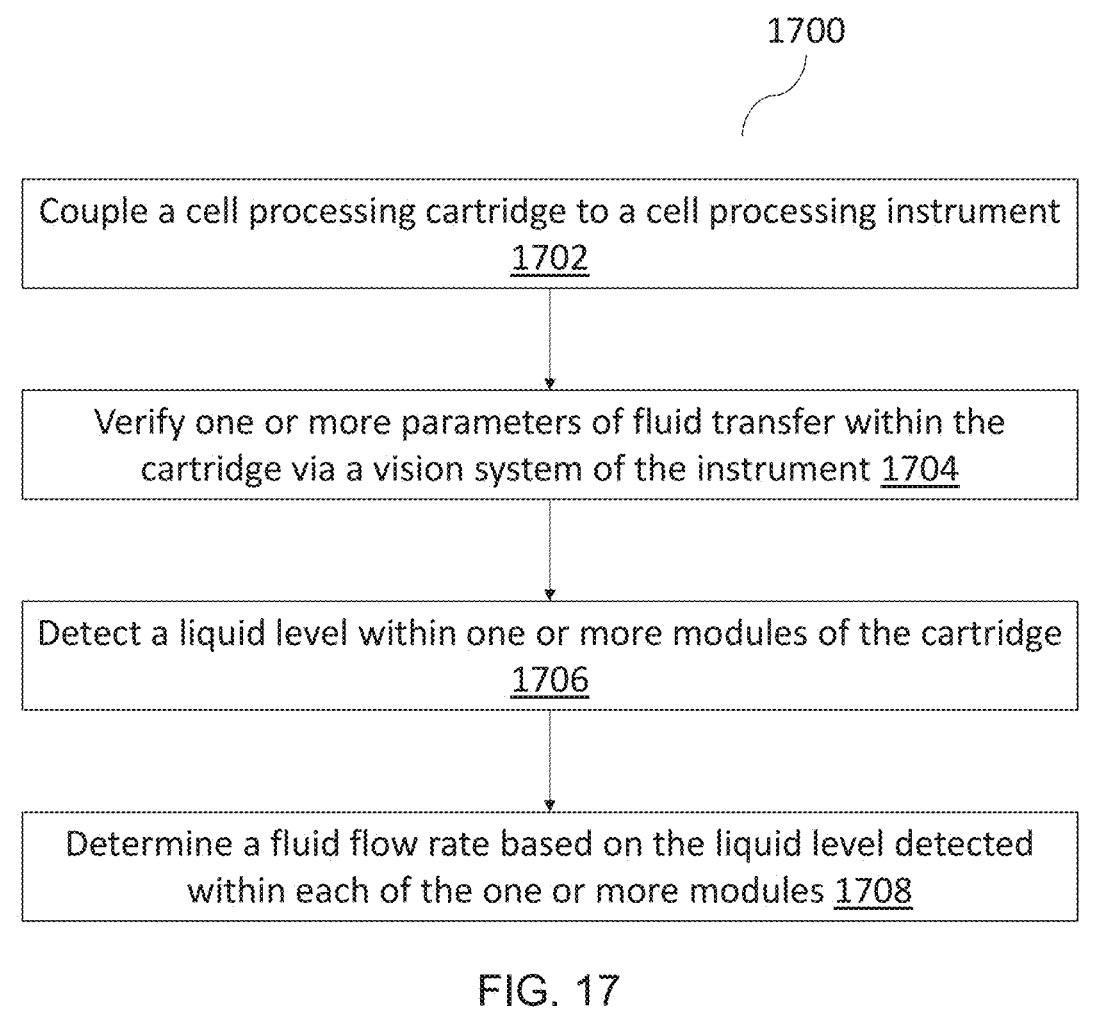

Couple a cell processing cartridge to a cell processing instrument
1702

Verify one or more parameters of fluid transfer within the
cartridge via a vision system of the instrument 1704

Detect a liquid level within one or more modules of the cartridge
1706

Determine a fluid flow rate based on the liquid level detected
within each of the one or more modules 1708

FIG. 17

LIQUID LEVEL AND FLOW RATE DETECTION WITHIN A CELL PROCESSING SYSTEM

CROSS REFERENCE TO RELATED APPLICATIONS

This application claims priority to U.S. Provisional Patent Application No. 63/570,739 filed Mar. 27, 2024, the content of which is incorporated herein by reference in its entirety for all purposes.

TECHNICAL FIELD

The present disclosure relates to systems, devices, and methods for monitoring liquid levels and liquid flow rates within automated cell processing systems.

BACKGROUND

Cell processing generally involves collecting and manufacturing cell products for therapeutic use. These cell products often achieve effective and robust clinical responses in patients. However, cell processing is a complex, often labor-intensive process that is difficult to scale up and is prone to human error and contamination. While recent efforts have been made regarding, for example, the ability to automate movements of cells between processing steps, conventional cell processing procedures still include numerous inefficiencies. For example, conventional "automated" cell processing systems often combine automated steps with cumbersome manual operations performed in expensive biosafety cabinets and/or cleanrooms. As another example, these systems generally rely on pre-configured instrumentation and tubing sets that limit operational flexibility and do not reliably prevent process failure due to human error. Moreover, most efforts to automate cell product manufacturing have been directed to automating individual processing steps of a cell therapy manufacturing workflow, and even systems that automate several steps may lack end-to-end process flexibility, process robustness, and process scalability. Therefore, there is a need for new and improved cell processing systems having decreased overhead, end-to-end process flexibility, process robustness, and requiring little to no operator interaction. For example, a desirable cell processing system may be a fully automated system including a workcell housing a plurality of cell processing instruments, where each instrument may interface with a cell processing cartridge (e.g., a unit carrying a cell product) to perform one or more steps of a cell processing procedure. The cell processing system may additionally be a multi-cartridge system (i.e., for processing multiple cartridges in parallel), which may provide additional benefits such as high-throughput and scalable manufacturing.

Monitoring the liquid levels and fluid transfer parameters within cartridges of such a system may further enhance efficiency and safety during cell processing. For example, verifying that a liquid level of the cartridge is at a desired level, or that a planned fluid transfer occurred between two components of the cartridge, may enhance the precision and accuracy of fluid filling and exchange within the cartridge. Additionally, such monitoring may reduce risk of system damage by, for example, detecting or predicting that liquid may overflow out of the cartridge, and modifying the fluid transfer therein to prevent the overflow. Therefore, it may be beneficial for the system to monitor the liquid levels and fluid transfer parameters within the cartridge.

Accordingly, there is a need for novel cell processing systems and methods for monitoring liquid levels and fluid transfer within a cell processing cartridge during automated cell processing.

SUMMARY

Described herein are systems, devices, and methods useful for cell processing. A method for calibrating an automated cell processing system may include coupling a calibration cartridge to an instrument within a cell processing workcell. The instrument may include a vision system and the calibration cartridge may include one or more fiducial markers. The method may also include detecting a location of each of the one or more fiducial markers using the vision system and generating a calibration result using the locations of each of the one or more fiducial markers. Generating the calibration result may include determining a region of interest (ROI) defined by the locations of each of the one or more fiducial markers and mapping the ROI onto a reference image. The calibration result may be an alignment map defining alignment between the vision system the instrument and the one or more fiducial markers of the calibration cartridge. In some variations, the method may further include applying the alignment map to an output of each of the one or more sensors during an automated cell processing procedure. In some variations, the output may include one or more images of the calibration cartridge obtained by the vision system. Moreover, the automated cell processing system may be calibrated during initial setup of the system. Further, the instrument may include a bioprocessing instrument or a sterile liquid transfer instrument.

In some variations, the calibration result may be generated for one or more modules of the calibration cartridge, where a cell processing cartridge may be configured to interface with the instrument to perform a cell processing operation, the cell processing cartridge comprising each of the one or more modules. In some variations, the method may further include coupling the cell processing cartridge to the instrument, where one or more cameras of the vision system may be directed toward the one or more modules of the cell processing cartridge when the cell processing cartridge is coupled to the instrument. Further, each of the one or more modules may include at least one fluid compartment configured to store a liquid therein. The one or more modules may include one or more of a bioreactor module, a magnetic cell separation (MCS) module, a centrifugal counterflow elutriation module, and a waste module. In some variations, the bioreactor module may include a bioreactor compartment, a mixing compartment, and one or more thermal compartments. In some variations, the calibration result may be a first calibration result and the one or more modules include the MCS module, the method may further include: detecting one or more features of the MCS module of the calibration cartridge using the vision system, generating an MCS module map based on the one or more features that defines alignment between an actual position of the calibration cartridge and a desired position of the calibration cartridge, and applying the MCS module map to an output of the vision system during a cell processing procedure to align the vision system to the MCS module.

In some variations, the calibration result may include a first calibration result, and the method may further include detecting coordinates of a calibration image having a known dimension using the vision system and generating a second calibration result using the coordinates of the calibration image. Generating the second calibration result may include mapping an output of the vision system to the coordinates of the calibration image. The second calibration result may be, for example, a distortion map defining distortion of the calibration image from the coordinates of the output of the vision system. In some variations, the method may further include applying the distortion map to the output of each of the one or more sensors during an automated cell processing procedure to compensate for the distortion. Moreover, the output comprises a real-time image. Furthermore, the method may include combining the first and second calibration results into a combined calibration result and applying the combined calibration result to an output of the vision system during a cell processing procedure.

The vision system may include a plurality of cameras supported by the instrument. One or more of the plurality of cameras may include a lens having a focal length of between about 8 mm and about 18 mm, or a focal length of between about 35 mm and about 50 mm.

Moreover, a method for automated cell processing may include coupling a cartridge to an instrument configured to perform a cell processing operation with at least one module of the cartridge, detecting, via a vision system of the instrument, a liquid level of a liquid within one or more modules of the cartridge, and determining a volume of the liquid based on the detected liquid level. Further, the instrument may include a bioprocessing instrument or a sterile liquid transfer instrument.

For each of the one or more modules, determining the volume of the liquid may include transforming a real-time image of a fluid compartment of the module to a numerical array representing one or more intensity gradients of the real-time image, identifying a peak intensity gradient of the numerical array, and determining a location of the liquid level based a position of the peak intensity gradient. The method may further include converting the location of the liquid level to a volume of the liquid based on a geometry of a fluid compartment of the cartridge.

In some variations, the vision system may include a plurality of cameras supported by the instrument. One or more of the plurality of cameras may be directed toward one of the one or more modules of the cartridge when the cartridge is coupled to the instrument. In some variations, the one or more modules may include one or more of a plurality of a bioreactor module, a magnetic cell separation (MCS) module, a centrifugal counterflow elutriation module, and a waste module. Each of the one or more modules may be configured to store liquid within at least one fluid compartment of the module. Moreover, the bioreactor module may include a bioreactor compartment, a mixing compartment, and one or more thermal compartments.

In some variations, the waste module may carry a floating member therein. The floating member may be configured to float at least partially above a surface of the liquid within the waste module. Determining the volume of the liquid may include identifying a location of the surface of the liquid based on one or both of an outline and a size of the floating member, transforming a real-time image of a fluid compartment of the waste module to a numerical array representing one or more intensity gradients of the real-time image, identifying a peak intensity gradient of the numerical array, and determining a location of the liquid level based on the location of the surface of the liquid and a position of the peak intensity gradient.

Another method for automated cell processing may include coupling a cartridge to an instrument configured to perform a cell processing operation with at least one module of the cartridge, verifying, via a vision system of the instrument, a flow path of liquid transfer from a first module of the cartridge to a second module of the cartridge. detecting, via the vision system, a liquid volume within one or both of the first and second modules during the liquid transfer, and determining a rate of the liquid transfer based on variations of the liquid volumes within the first and second modules. In some variations, the method may further include comparing the liquid volume of the first module to a liquid volume threshold and stopping the liquid transfer when the liquid volume of the first module is about equal to or less than the liquid volume threshold. Additionally, or alternatively, the method may further include comparing the liquid volume of the second module to a liquid volume threshold and stopping the liquid transfer when the liquid volume of the second module about equal to or is greater than the liquid volume threshold. In some variations, the plurality of modules may include two or more of a bioreactor module, a magnetic cell separation (MCS) module, a centrifugal counterflow elutriation module, and a waste module. Moreover, the vision system may include a plurality of cameras supported by the instrument. One or more of the plurality of cameras may be directed toward one or more modules of the cartridge when the cartridge is coupled to the instrument. Additionally, in some variations, the instrument may be a bioprocessing instrument or a sterile liquid transfer instrument.

Further, a system for automated cell processing may include a cartridge, which may have one or more modules for cell processing, and an instrument which may be configured to couple to the cartridge to perform a cell processing operation. The instrument may include an enclosure and a vision system positioned on the enclosure and configured to detect a liquid level of the liquid within the one or more modules of the cartridge. Additionally, the instrument may include a processor configured to determine a volume of the liquid based on the liquid level. Further, the instrument may include a bioprocessing instrument or a sterile liquid transfer instrument. In some variations, the system may further include a fluidic bus configured to transfer liquid between the one or more modules of the cartridge.

The vision system may include a plurality of cameras. In some variations, the enclosure of the instrument may have a plurality of sides, and each of the plurality of cameras may positioned on one of the plurality of sides of the enclosure. In some variations, one or more of the plurality of cameras may be directed toward one of the one or more modules of the cartridge when the cartridge is coupled to the instrument.

In some variations, the one or more modules may include one or more of a plurality of a bioreactor module, a magnetic cell separation (MCS) module, a centrifugal counterflow elutriation module, and a waste module. Each of the one or more modules may be configured to store liquid within at least one fluid compartment of the module. Moreover, the bioreactor module may include a bioreactor compartment, a mixing compartment, and one or more thermal compartments.

In some variations, the waste module may carry a floating member therein. The floating member may be configured to float at least partially above a surface of the liquid within the waste module. The processor may be configured to determine a change in one or both of an outline and a size of the floating member to detect the liquid level within the waste module.

Another system for automated cell processing may include a cartridge, which may have one or more modules for cell processing, and an instrument which may be configured to interface with at least one of the one or more modules to perform a cell processing operation. The instrument may include an enclosure and vision system positioned on the enclosure. The vision system may be configured to verify a flow path of liquid transfer from a first module of the one or more modules to a second module of the one or more modules and detect a liquid volume within one or both of the first and second modules during the liquid transfer. Furthermore, the instrument may include a processor configured to determine a rate of the liquid transfer based on variations of one or both of the detected liquid volumes within the first and second modules. In some variations, the system may further include a pump configured to maintain a desired rate of the liquid transfer between the first and second modules. The pump may be configured to turn off when a liquid level condition is met. The liquid level condition may be a threshold of the liquid volume within the first module, and the pump may turn off when the liquid volume within the first module is about equal to or less than the liquid volume threshold. Additionally, or alternatively, the liquid level condition may be a threshold of the liquid volume within the second module, and the pump may turn off when the liquid volume within the second module is about equal to or greater than the liquid volume threshold. In some variations, the system may further include a fluidic bus for transferring liquid between the two or more of the plurality of modules. The plurality of modules comprises two or more of a bioreactor module, a magnetic cell separation (MCS) module, a centrifugal counterflow elutriation module, and a waste module. Moreover, the vision system may include a plurality of cameras supported by the instrument. One or more of the plurality of cameras may be configured to face a fluid compartment of one or more of the plurality of modules of the cartridge. Finally, in some variations, the instrument may be a bioprocessing instrument or a sterile liquid transfer instrument.

BRIEF DESCRIPTION OF THE DRAWINGS

FIG. 8A is a rendering of an exterior view of an illustrative variation of a waste module of a cartridge. FIG. 8B is a depiction of a front view of an illustrative variation of a waste column of a waste module.

FIG. 16 is a flow diagram of an illustrative method for monitoring liquid levels within a cartridge during cell processing.

FIG. 17 is a flow diagram of an illustrative method for monitoring fluid transfer within a cartridge during cell processing.

DETAILED DESCRIPTION

Figure 1A:
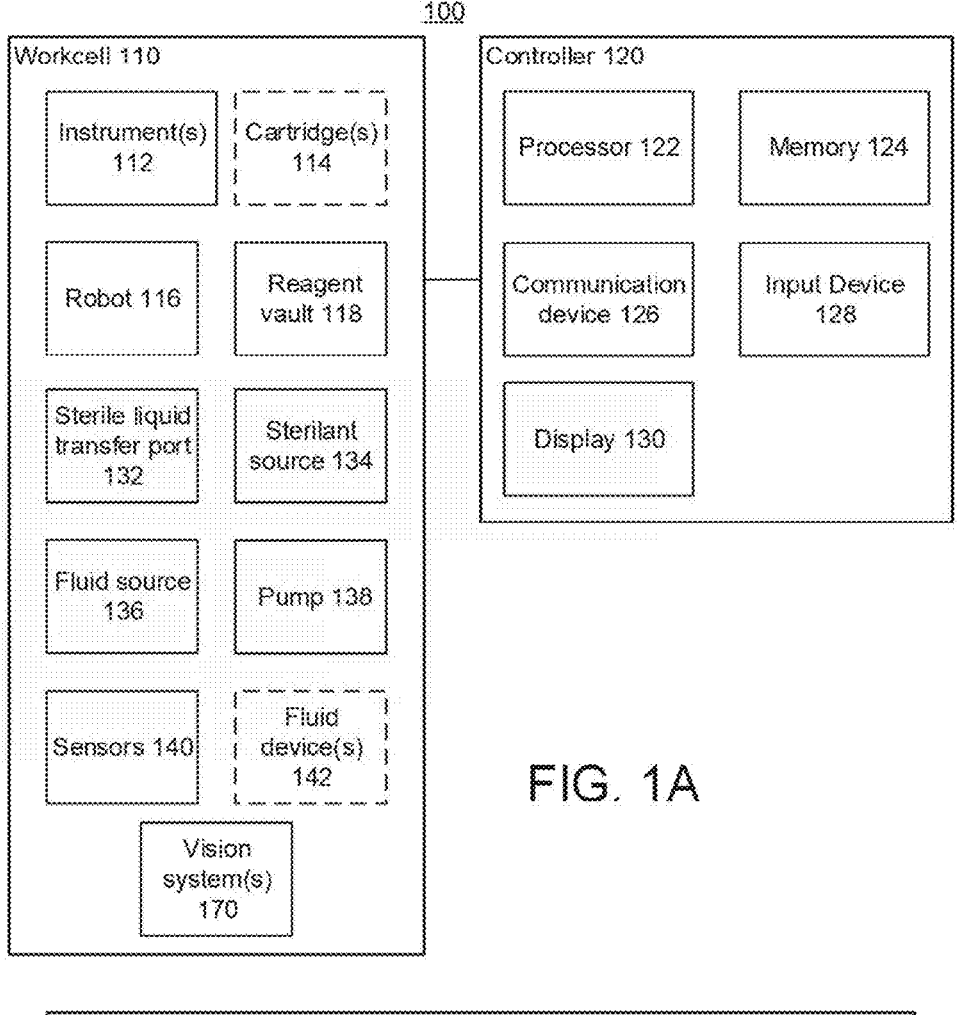
FIG. 1A is a block diagram of an illustrative variation of a workcell of a cell processing system.

Described herein are systems, devices, and methods for automated cell processing including systems, devices, and methods useful for monitoring liquid levels and fluid transfer (e.g., for monitoring parameters thereof) within a cell processing cartridge during automated cell processing. In general, the cell processing systems ("systems") herein may be fully or partially automated, and may include a workcell housing a plurality of cell processing instruments ("instruments"), where each instrument may be configured to interface with a cell processing cartridge ("cartridge") to perform one or more steps of a cell processing procedure. In particular, each instrument may be configured to receive a cartridge and interface with one or more cell processing modules ("modules") thereof. An advantage of such split module designs is that expensive components (e.g., sensors, motors, heaters, lasers, pumps, processors, etc.) may be retained in the workcell. Additionally, the use of disposable cartridges may eliminate the need, in such variations, to sterilize cartridges between use. Still, even disposable cartridges may require sterilization steps (e.g., prior to entering the workcell and/or after exiting the workcell), which may not be compatible with on-board electronics (e.g., gamma radiation may destroy on-board electronics of the cartridges with high energy photons). Thus, in some variations, the cartridges herein may include few to no electronics (e.g., no electronics) to enhance manufacturing, cost, and process efficiency.

To perform a cell processing procedure for a single cartridge (e.g., for a cell product carried by the cartridge), fluid (e.g., liquid) may be transferred between the modules of the cartridge. For example, fluid(s) including liquids and/or mixtures may be transferred into and/or out of a module (e.g., one or more modules) of the cartridge during cell processing. The liquids and/or mixtures may include one or more of cell culture media, buffer, cytokines, proteins, enzymes, polynucleotides, transfection reagents, non-viral vectors, viral vectors, antibiotics, nutrients, cryoprotectants, solvents, cellular materials, waste, and pharmaceutically acceptable excipients. It may be desirable to monitor the fluid (e.g., liquid) level(s) within the cartridges herein, such as to monitor a liquid level (i.e., volume) within and/or fluid transfer between one or more modules thereof during cell processing. For example, monitoring the liquid levels and fluid transfer parameters within a cartridge using a feedback loop (e.g., comparing real-time liquid levels to desired liquid levels) may facilitate precise filling operations within the cartridge based on real-time calculations and verifications of liquid levels and/or fluid transfer parameters such as flow rates and flow paths. Additionally, system damage may be prevented if the liquid levels within fluid compartment(s) (e.g., of the modules) of the cartridge are monitored to detect potential liquid overflow from the compartment(s). Thus, monitoring liquid levels and/or fluid transfer within the cartridge may enhance the efficiency and safety of auto-mated cell processing.

However, monitoring the liquid levels and/or fluid trans-fer may be difficult. In some variations, a cartridge may include one or more sensors for detecting liquid levels, flow rates, and/or flow paths. Alternatively, as described above, it may be beneficial to use a cartridge having few to no on-board electronics. For example, a cartridge having no on-board electronics may be compatible with a gamma radiation sterilization step, which is a low-cost form of sterilization that does not produce toxic residues. Therefore, the systems, devices, and methods herein may include solutions for monitoring liquid levels and/or liquid flow rates and paths within the cartridge via the workcell (e.g., via the instrument(s) of the workcell). As described herein throughout, the instruments herein may include a vision system having one or more sensors (e.g., supported by an enclosure of the instrument) that are configured to detect the liquid levels and/or fluid transfer parameters within a car-tridge interfacing with the instrument. Furthermore, the systems, devices, and methods herein may be configured to calibrate fluid transfer within a cell processing cartridge (e.g., a calibration cartridge comprising a substantially iden-tical structure as a cell processing cartridge).

Exemplary variations of systems, devices, and methods for calibrating fluid transfer within a cartridge for cell processing, as well as monitoring liquid levels and fluid transfer of the cartridge during cell processing, are described in detail below.

I. Cell Processing Systems

The cell processing systems herein may be automated and configured for manufacturing of cell products for biomedical applications. The systems herein may additionally be con-figured for processing multiple cartridges in parallel (i.e., may be multi-cartridge systems) to provide high-throughput manufacturing and process scalability. Any suitable cell processing procedure may be performed using the systems and devices described herein, and may include steps such as growing, enriching, selecting, sorting, expanding, activat-ing, transducing, electroporating, washing, and the like. For example, a cell processing procedure may include the steps of digesting tissue using an enzyme reagent to release a select cell population into solution, enriching cells using a CCE instrument, washing cells using the CCE instrument, selecting cells in the solution using a selection instrument, sorting cells in the solution using a sorting instrument, differentiating or expanding the cells in a bioreactor, acti-vating cells using an activating reagent, electroporating cells, transducing cells using a vector, and finishing a cell product.

An illustrative cell processing system for use with the methods herein is shown in FIG. 1A. Shown there is a block diagram of a cell processing system 100 including a work-cell 110 and controller 120. The workcell 110 may include one or more of instrument(s) 112, a robot 116 (e.g., robotic arm), a reagent vault 118, a sterile liquid transfer port 132, a sterilant source 134, a fluid source 136, a pump 138, sensor(s) 140, and vision system(s) 170. Cartridge(s) 114 and fluid device(s) 142, which may be provided outside of the workcell 110 and used within used within the workcell 110, are illustrated in dashed lines. In some variations, a fluid device 142 may be a liquid transfer device, such as a sterile liquid transfer device (SLTD). The robot 116 may be configured to move the cartridge(s) 114 and/or fluid device(s) 142 throughout the workcell 110. For example, the robot 116 may be configured to move the cartridge(s) 114 between one or more instrument(s) 112 such that various cell processing operations may be performed on the cartridge(s) 114. As another example, the robot 116 may be configured to releasably couple the fluid device(s) 142 to the cartridge(s) 114 and/or the instrument(s) 112 such that fluids (e.g., liquids) may be transferred between the fluid device(s) 142 and the cartridge(s) 114 and/or the instrument(s) 112. However, it should be appreciated that the fluid device 142 may be configured to transfer any fluid (which includes liquids), whether sterile or not. The pump 138 may be configured to engage a cartridge 114 within a docking station of an instrument 112. For example, the pump 138 may include a rotor configured to control a flow rate of fluid transfer within the cartridge 114. For example, an opera-tional speed (e.g., rotational speed) of the pump 138 may correspond to the flow rate, and may be adjusted (e.g., via the controller 120) to control fluid transfer within the cartridge 114.

The sensor(s) 140 may include one or more sensors (e.g., bubble sensors, optical sensors, etc.) supported by the instru-ment(s) 112 for generating data for the cartridge 114 (s) interfacing with the instrument(s) 112. As explained in detail herein, the vision system(s) 170 may include one or more sensors, which may be or include a subset (e.g., some) or all of the sensors 140, such as one or more cameras for detecting and/or generating data (e.g., image data, such as real-time image data) of liquid levels (i.e., volumes) within the cartridge(s) 114. The vision system(s) 170 may generally be supported by (e.g., mounted on or within walls of) enclosures of the instrument(s) 112. In some variations, each of a plurality of instruments 112 may include an associated vision system 170. Alternatively, in some variations, a subset (e.g., fewer than all) of a plurality of instruments 112 of the workcell 110 may include an associated vision system 170. Further, the vision system(s) 170 may include one or more additional components (e.g., light sources, mirrors, prisms, polarizers, and/or the like) for providing light, and reflect-ing, separating, angling, and/or filtering the light to create optical paths for the one or more sensors of the vision system(s) 170. In some variations, the cartridge(s) 114 may support some of the additional components of the vision system(s) 170 for creating optical paths within the cartridge(s) 114.

In some variations, the controller 120, including one or more features thereof, may be operably coupled to (e.g., wirelessly) the vision system(s) 170, or may be a component of the vision system(s) 170. The controller 120 may include one or more of a processor 122, a memory 124, a communication device 126, an input device 128, and a display 130. As described herein, the controller 120 may be configured to receive liquid level and/or flow rate and flow path data of the cartridge(s) 114 from one or more of the sensors 140. In some variations, the controller 120 may be configured to determine (e.g., via processor 122) a liquid level (i.e., volume) of liquid within a given module (or fluid compartment thereof) using the data from the vision system(s) 170. Additionally, or alternatively, the controller 120 may be configured to determine (e.g., via processor 122) one or more fluid transfer parameters, such as a flow rate of fluid transfer within a cartridge 114 using data from the vision system(s) 170. Further, in some variations, the controller 120 may be configured to control (e.g., using processor 122) precise filling of one or more modules of a cartridge 114 by comparing data from the vision system(s) 170 to a liquid level condition. Further, in some variations, a status (e.g., a real-time status) of the liquid level and/or fluid transfer data of one or more of the cartridge(s) 114 may be displayed for operator viewing and/or interaction via display 130.

Figure 1B:
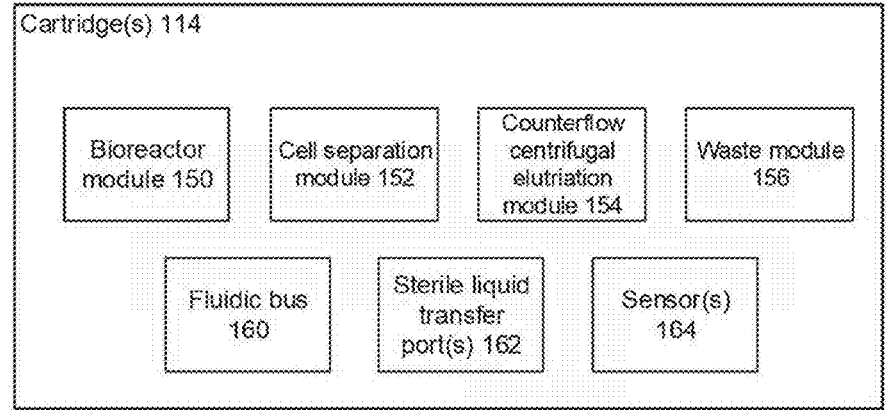
FIG. 1B is a block diagram of an illustrative variation of a cartridge of the cell processing system.

As described above, the cartridge(s) 114 may include one or more modules, such as a plurality of modules, for cell processing. The modules may generally include one or more of a bioreactor module, a counterflow centrifugal elutriation (CCE) module, a magnetic cell sorter (MCS) module (e.g., magnetic-activated cell selection (MACS) module), a waste module, an electroporation (EP) module, a sorting module (e.g., fluorescence activated cell sorting (FACS) module), an acoustic flow cell module, a centrifugation module, a microfluidic enrichment module, a transduction module, and/or the like. For example, as shown in FIG. 1B, a cartridge 114 may include a bioreactor module 150, an MCS module 152, a CCE module 154, and a waste module 156. Additionally, the cartridge 114 may include a fluidic bus 162 for facilitating fluid transfer within the cartridge 114 (e.g., between modules thereof), and a sterile liquid transfer port(s) 164 for facilitating fluid transfer into/out of the cartridge 114. For example, the sterile liquid transfer port(s) 164 may be couplable to a corresponding sterile liquid transfer port of a fluid device 142 such that fluid (e.g., liquid) may be transferred between the cartridge and the fluid device via the ports. Optionally, in some variations, the cartridge 114 may further include sensors 166, such as one or more sensors for detecting the liquid levels and/or liquid flow rates and paths within the cartridge 114.

Figure 2:
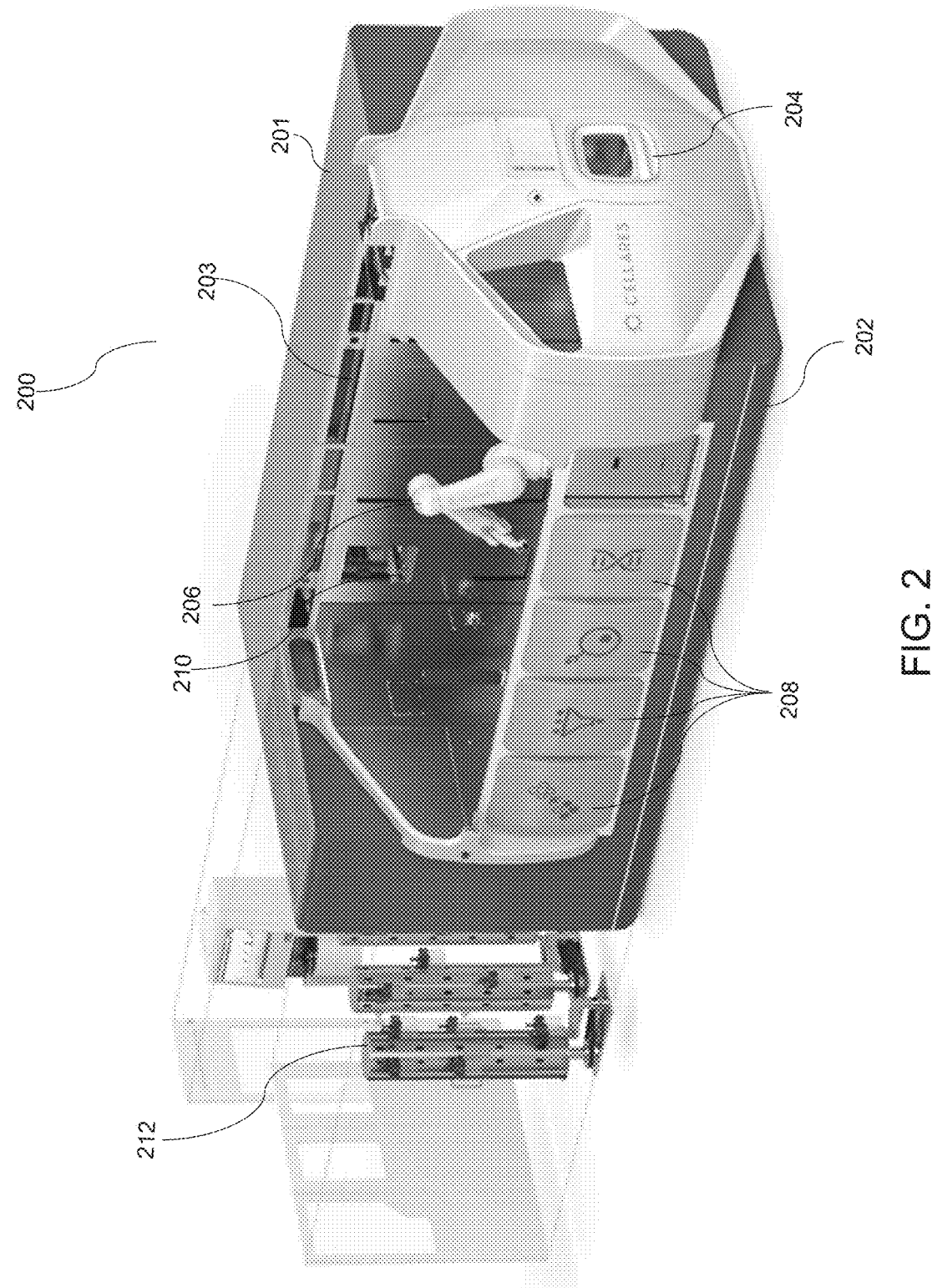
FIG. 2 is a perspective view of an illustrative variation of a cell processing system.

Similarly, FIG. 2 is a sectional depiction of an exemplary cell processing system 200 including workcell 202 having enclosure 203 and interior 201. A cartridge (not shown) may be loaded into the interior 201 of workcell 202 may through a feedthrough 204. In some variations, the feedthrough 204 may be a first of a plurality of feedthroughs 204. In some variations, the cartridge may undergo one or more sterilization steps within the feedthrough 204. For example, the sterilization may include one or more of hot air sterilization, gamma radiation, vaporized hydrogen peroxide (VHP) processing, ionized hydrogen peroxide decontamination, and/or the like. Once inside the workcell 202, the cartridge may be moved throughout its interior via robot(s) 206. For example, the robot(s) 206 may be configured to move the cartridge into one or more instruments 208, such as into a docking station 210 of an instrument 208. Additionally, the robot(s) 206 may be configured to move one or more fluid devices (not shown) about the workcell. For example, the robot(s) 206 may be configured to pick up and/or drop off one or more fluid devices within the reagent vault 212. Additionally, or alternatively, the robot(s) 206 may be configured to pick up and/or drop off one or more fluid devices at an instrument 208, such as to couple or decouple a fluid device from a cartridge interfacing with an instrument 208.

Cartridges

Figure 3:
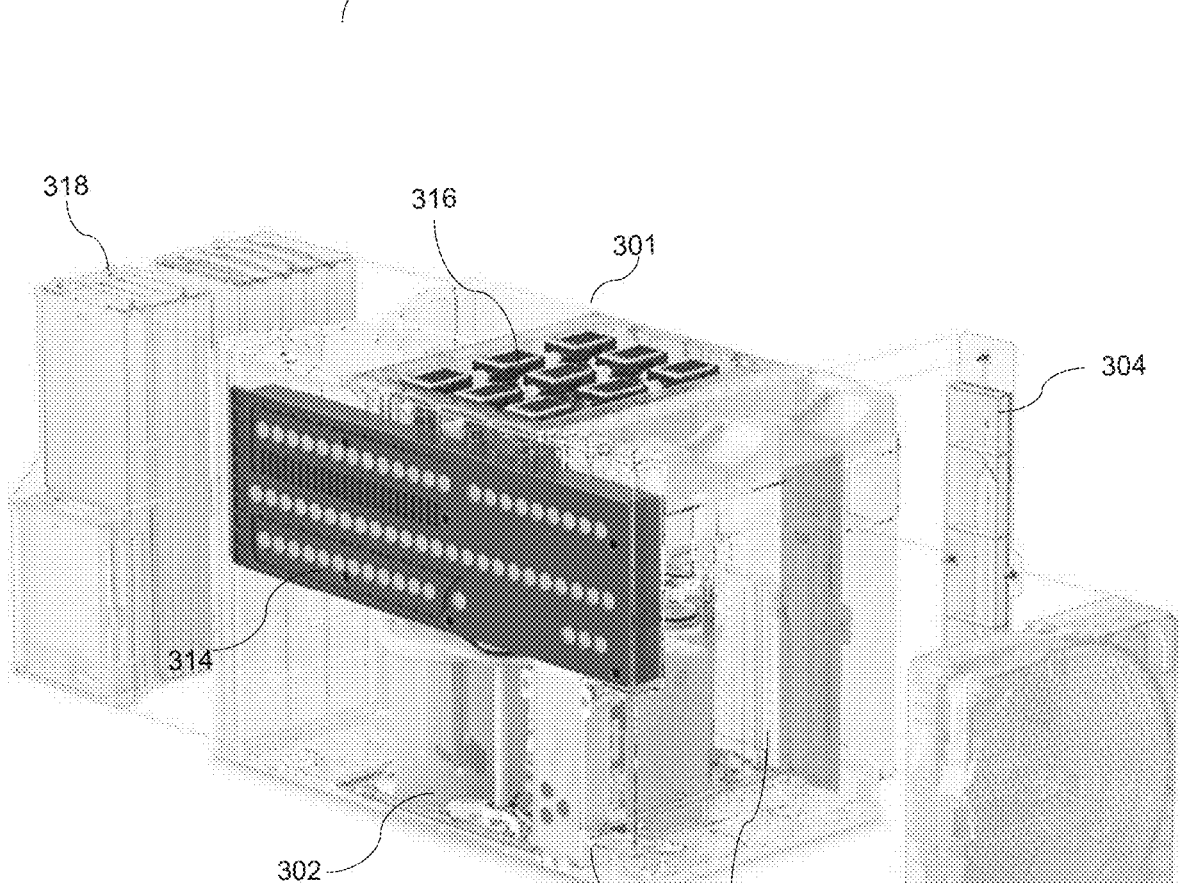
FIG. 3 is a perspective view of an illustrative variation of a cartridge of the cell processing systems herein.

The cell processing systems described herein may include one or more cartridges configured to contain a cell product for processing. The cartridges may include one or more modules configured to interface with one or more instruments within the workcell. In particular, the one or more modules of a cartridge may have fluid compartment(s) that are monitored by an instrument (e.g., by a vision system thereof) interfacing with the cartridge to detect liquid levels of the fluid compartment(s) and/or to detect flow rates and flow paths of fluid transfer within the cartridge. The cartridges herein may be calibration cartridges and/or cell processing cartridges. In some variations, a calibration cartridge may be structurally equivalent to a cell processing cartridge. In some variations, a calibration cartridge may include one or more fiducial markers while a cell processing cartridge may not include fiducial markers. For example, a calibration cartridge may include a plurality of fiducial markers for facilitating alignment between cartridges (e.g., calibration and cell processing cartridges) and a vision system of an instrument (e.g., vision system(s) 170 of FIG. 1A). In particular, the vision system may be configured to detect the fiducial markers (during, e.g., a calibration procedure using the calibration cartridge) to define one or more regions-of-interest (ROIs) of the cartridge. In some variations, an ROI may include one or more portions of a cartridge module, such as one or more fluid compartments thereof, and the vision system may be configured to detect and/or generate data (e.g., optical data) for monitoring a same module of a cell processing cartridge during a cell processing operation, such as during a fluid transfer step within the cartridge. For example, a vision system may detect liquid levels and/or fluid transfer parameters within a cartridge indirectly such that the vision system does not interfere with fluid flow paths within the cartridge. Accordingly, in some variations, the vision systems herein may not include sensors that contact or obstruct flow paths of the cartridge. As will be discussed herein, the vision system may additionally be configured to illuminate the ROI via, for example, a light source. In some variations, monitoring the cell processing module may facilitate modifying the cell processing operation in a closed loop manner based on predetermined criteria. For example, the module (e.g., one or more fluid compartments thereof) may be monitored to track liquid levels and/or fluid transfer parameters within the module to allow for precise filling, provide detailed feedback for an operator, and/or to prevent system damage due to liquid overflow within the module. In some variations, FIG. 3 provides a stylized depiction of an exemplary cartridge 300 which includes a housing 301 and a plurality of modules therein. For example, the cartridge 300 includes a bioreactor module 302. A bioreactor module may include one or more fluid compartments for facilitating cell expansion, such as one or more bioreactors (e.g., one, two, three, four, or more than four thereof), one or more mixing chambers (e.g., one, two, three, four, or more than four thereof), and one or more thermal containers (e.g., one, two, three, four, or more than four thereof). The cartridge 300 of FIG. 3 also includes an MCS module 304. An MCS module may include one or more fluid compartments for facilitating cell sorting and/or cell transduction, such as one or more flow cells (e.g., one, two, three, four, or more than four flow cells), and one or more target cell reservoirs (e.g., one, two, three, four, or more than four target cell reservoirs). Further, the cartridge 300 includes CCE module 306. A CCE module may include one or more fluid compartments for facilitating cell separation, such as one or more elutriation chambers (e.g., one, two, three, four, or more than four elutriation chambers). Additionally, the cartridge 300 includes a waste module 308. A waste module may include one or more fluid compartments for storing waste (e.g., liquid waste) therein, such as one or more waste columns. Moreover, the cartridge 300 includes an EP module 312 for electroporating cells, a fluidic bus 314 for enabling fluid transfer between the modules of the cartridge 300, sterile liquid transfer port(s) 316 for supporting fluid transfer (e.g., reagent additions, waste removal and/or automated sampling) between the cartridge 300 and other component(s) of the system (e.g., a fluid device), and fluid compartment(s) 318 for storing a final cell product. For a cartridge including a plurality of modules, each of the modules may be fluidically coupled to the fluidic bus such that fluid may be transferred among the modules.

The fluid paths of the cartridges herein may generally include paths within a single module, such as between two different fluid compartments of a module, as well as paths between a plurality of modules (e.g., fluid compartments thereof), such as between 2, 3, 4, 5, 6, 7, 8, 9, 10, or more than 10 modules. For example, a fluidic bus and tubing between first module or fluid compartment and a second (same or different) module or fluid compartment may define a fluid path within a cartridge. In some variations, the first (e.g., origin) module or fluid compartment and the second (e.g., destination) module or fluid compartment may be the same. For example, a transduction step may involve numerous transfers of cells between a bioreactor module and a flow cell of an MCS module. The bioreactor module, which may be the origin module, may also be the destination module (or vice versa with respect to the flow cell). Alternatively, in some variations, the bioreactor module may only be the origin module or the destination module (and/or vice versa with respect to the flow cell).

Moreover, a flow rate of fluid transfer within the cartridges herein may be constant or variable. In some variations, an operator and/or a controller of the system (e.g., controller 120 of FIG. 1A) may set and/or adjust the flow rate of a given fluid transfer. Generally, the flow rate may be about 1 mL/min to about 150 mL/min, about 2 mL/min to about 125 mL/min, about 3 mL/min to about 100 mL/min, about 4 mL/min to about 75 mL/min, about 5 mL/min to about 50 mL/min, about 6 mL/min to about 25 mL/min, about 7 mL/min to about 15 mL/min, or about 8 mL/min to about 10 mL/min (including all ranges and subranges in-between). In some variations, the flow rate may be about 1 mL/min, about 2 mL/min, about 3 mL/min, about 4 mL/min, about 5 mL/min, about 6 mL/min, about 7 mL/min, about 8 mL/min, about 9 mL/min, about 10 mL/min, about 15 mL/min, about 20 mL/min, about 25 mL/min, about 30 mL/min, about 35 mL/min, about 40 mL/min, about 45 mL/min, or about 50 mL/min. Similarly, in some variations, the flow rate may be at least 1 mL/min, at least 2 mL/min, at least 3 mL/min, at least 4 mL/min, at least 5 mL/min, at least 6 mL/min, at least 7 mL/min, at least 8 mL/min, at least 9 mL/min, or at least 10 mL/min.

Various materials may be used to construct the cartridges herein and the cartridge housing, including metal, plastic, rubber, glass, and/or combinations thereof. In some variations, the cartridges herein may be constructed (at least in part) of transparent and/or translucent materials. For example, at least a portion of one or more cartridge modules herein may be transparent and/or translucent to facilitate illumination by a light source and data generation (e.g., image data generation) by a sensor (e.g., a camera of an instrument configured to interface with a given module). In some variations, one or more fluid compartments of a cartridge module may be constructed of transparent and/or translucent materials such that a liquid level of liquid within each of the fluid compartments may be detected via a vision system (e.g., one or more sensors) of an associated instrument (e.g., supported by a housing of the instrument). A cartridge, its components, and its housing may be molded, machined, extruded, 3D printed, or any combination thereof. The cartridge may contain components that are commercially available (e.g., tubing, valves, fittings, etc.)—these components may be attached or integrated with custom components or devices. The housing of the cartridge may constitute an additional layer of enclosure that further protects the sterility of the cell product.

In some variations, the cartridge modules herein may be comprised of distinct sections that are integrated in a fixed configuration. Additionally, or alternatively, the modules may be configurable or moveable within a cartridge, permitting various formats of cartridges to be assembled. For example, a cartridge may be a single, closed unit with fixed components for each module, or the cartridge may contain configurable modules coupled by configurable fluidic, mechanical, optical, and electrical connections. In some variations, one or more sub-cartridges, each containing a set of modules, may be used to perform various cell processing workflows. The modules may each be provided in a distinct housing or may be integrated into a cartridge or sub-cartridge with other modules. The disclosure generally shows modules as distinct groups of components for the sake of simplicity, but it should be noted that these modules may be arranged in any suitable configuration. For example, the components for different modules may be interspersed with each other such that each module is defined by the set of connected components that collectively perform a predetermined function. However, the components of each module may or may not be physically grouped within the cartridge. In some variations, multiple cartridges may be used to process a single cell product through transfer of the cell product from one cartridge to another cartridge of the same or different type and/or by splitting cell product into more cartridges and/or pooling multiple cell products into fewer cartridges.

Several cartridge modules, which may include one or more fluid compartments for monitoring during one or more cell processing steps, are described in more detail below. Additionally, suitable cartridges, modules, and aspects thereof, are additionally provided in, e.g., U.S. Pat. No. 11,872,557, issued Jan. 16, 2024, U.S. Prov. Pat. App. 63/470,381, filed Jun. 1, 2023, and U.S. Prov. Pat. App. 63/524,596, filed Jun. 30, 2023, and U.S. Prov. Pat. App. 63/612,987, filed Dec. 20, 2023, the contents of each of which are hereby incorporated by reference herein in their entirety.

Bioreactor Module

Figure 4A:
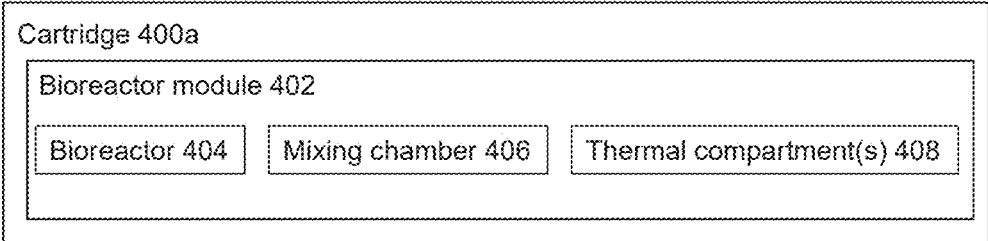
FIG. 4A is a block diagram of an illustrative variation of a cartridge having a bioreactor module.

A bioreactor module may support one or more cell processing steps such as one or more of activation, transduction, and expansion. In general, the bioreactor module may include a bioreactor for providing closed-loop control and real-time monitoring of one or more of the temperature, dissolved oxygen concentration, and acidity of a cell solution. FIG. 4A shows a block diagram of an exemplary bioreactor module 402 of a cartridge 400a for use with the systems, devices, and methods herein. The bioreactor module 402 may include a bioreactor 404, a mixing chamber 406, and one or more thermal compartments 408. For example, the one or more thermal compartments 408 may include 1, 2, 3, 4, 5, or more than 5 thermal compartments, such as first and second thermal compartments, or first, second, and third thermal compartments.

In some variations, fluid may be transferred between the bioreactor 404, the mixing chamber 406, and/or the one or more thermal compartments 408. Additionally, or alternatively, fluid may be transferred to and/or from another module of the cartridge 400a from and/or to any one of the bioreactor 404, the mixing chamber 406, and/or the one or more thermal compartments 408.

The bioreactor 404 may be configured to hold a volume of fluid and perform one or more processes to the fluid therein. For example, the bioreactor 404 may be configured to perform one or more of a stirring process, static process, and perfusion process as described herein. That is, the bioreactor 404 may advantageously facilitate high-throughput cell processing by performing one or more processes within the bioreactor 404 itself and thereby reducing or eliminating the need to transfer the fluid to another module. The one or more processes and/or fluid transfers in and/or out of the bioreactor 404 may be performed in accordance with a pre-determined workflow. In some variations, the bioreactor 404 may comprise one or more sidewalls that may be impermeable to liquid and/or gas. The bioreactor 404 may be configured to hold a volume of fluid of about 5 mL to about 2 L, about 50 mL to about 800 mL, or about 100 mL to about 600 mL, including about 50 mL, about 100 mL, about 200 mL, about 300 mL, about 400 mL, about 500 mL, about 600 mL, about 700 mL, about 800 mL, about 900 mL, about 1 L, about 1.5 L, or about 2 L (including all ranges and subranges therein). The bioreactor 404 may have any suitable cross-sectional shape, such as, for example, a circle, an oval, a rectangle, a triangle, or a combination thereof.

The mixing chamber 406 may be configured to hold a volume of fluid and perform one or more processes to the fluid therein. For example, the mixing chamber 406 may be configured to perform a stirring process. That is, the mixing chamber 406 may receive one or more reagents, which may be combined with a fluid using an impeller of the mixing chamber 406. The impeller may rotate such that the one or more reagents may mix with (e.g., contact) target cells (e.g., cells intended for further processing and/or use in cell therapies). The resulting mixture may be transferred out of the mixing chamber 406 to the bioreactor 404, thermal compartments 408, and/or another module of the cartridge 114. The fluid and/or reagent(s) may be transferred in and/or out of the mixing chamber 406 in accordance with a pre-determined workflow. For example, the mixing chamber 406 may comprise one or more sidewalls that may be impermeable to liquid and/or gas. The mixing chamber 406 may be configured to hold a volume of fluid of about 5 mL to about 1 L, about 50 mL to about 800 mL, or about 100 mL to about 600 mL, including about 50 mL, about 100 mL, about 200 mL, about 300 mL, about 400 mL, about 500 mL, about 600 mL, about 700 mL, about 800 mL, about 900 mL, or about 1 L (including all ranges and subranges therein). The mixing chamber 406 may comprise a cross-sectional shape such as a circle, an oval, a rectangle, a triangle, or a combination thereof.

The thermal compartments 408 may each be configured to hold a volume of fluid in a stable environment. For example, one or more the thermal compartments 408 may be thermally coupled to the bioreactor 404 and/or mixing chamber 406, such that there be thermal equilibrium therebetween. The thermally balanced configuration may facilitate cell culturing by mitigating issues associated with a cell solution experiencing changes in temperature. For example, cell growth and/or division may slow down or stop completely if the cell solution temperature drops below an intended value. In another example, one or more cell proteins may denature if the cell solution temperature increases above an intended value. Additionally, or alternatively, the thermal compartments 408 may maintain a stable gaseous environment therein. That is, one or more the thermal compartments 408 may be fluidically connected to a port system (not shown), which may be configured to provide oxygen, carbon dioxide, nitrogen, and/or sterile air as required to maintain the cell solution at a stable pH and with sufficient oxygen and/or nitrogen dissolved therein. Accordingly, the thermal compartments 408 may be configured to facilitate cell culturing by maintaining a thermal and/or gaseous environment. In some variations, each of the thermal compartments 408 may comprise one or more sidewalls that may be impermeable to liquid and/or gas. Each of the thermal compartments 408 may be configured to hold a volume of fluid of about 5 mL to about 1 L, about 50 mL to about 800 mL, or about 100 mL to about 600 mL, including about 50 mL, about 100 mL, about 200 mL, about 300 mL, about 400 mL, about 500 mL, about 600 mL, about 700 mL, about 800 mL, about 900 mL, or about 1 L (including all ranges and subranges therein). In some variations, the thermal compartments 408 may be configured to hold the same volume of fluid, but need not. For example, a first thermal compartment may be configured to hold a volume of about 600 mL, a second thermal compartment may be configured to hold a volume of about 100 mL, and a third thermal compartment may be configured to hold a volume of about 600 mL. The volume(s) may be determined by a pre-determined workflow. For example, after a cell sorting step, cellular material may be transferred to the second thermal compartment. The relatively smaller volume of the second thermal compartment may correspond to the relatively small number of cells that may be obtained via the cell sorting step described previously. In another example, the 600 mL capacity of the first and third thermal compartments may be appropriate to house cellular material after performing an expansion step, which may correspond to a relatively high number of cells. The fluid may be transferred in and/or out of each of the thermal compartments 408 in accordance with a pre-determined workflow.

Figure 5:
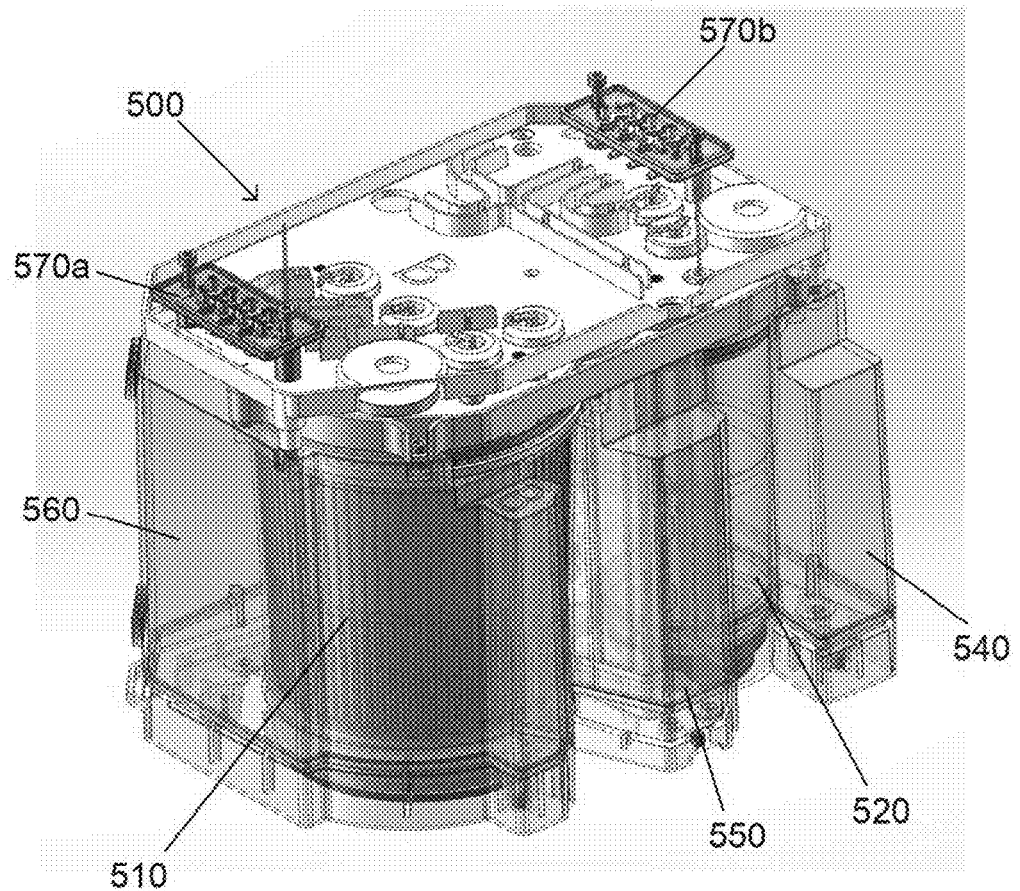
FIG. 5 is a rendering of a perspective view of an illustrative variation of a bioreactor module of a cartridge.

Referring to FIG. 5, an illustrative variation of a bioreactor module 500 is shown. The bioreactor module 500 may comprise a bioreactor 510, a mixing chamber 520, a first thermal compartment 540, a second thermal compartment 550, a third thermal compartment 560, a first plurality of fluid ports 570a, and a second plurality of fluid ports 570b. The plurality of fluid ports 570a, 570b may be positioned on a top surface of the bioreactor module 500. The plurality of fluid ports 570a, 570b may be configured to transfer a fluid to one or more of the bioreactor 510, mixing chamber 520, first thermal compartment 540, second thermal compartment 550, and third thermal compartment 560. That is, the plurality of fluid ports 570a, 570b may be fluidically connected to a fluidic manifold, such that a fluid may be transferred between the fluidic bus and the bioreactor module via the plurality of fluid ports 570a, 570b.

As shown, the bioreactor 510 may comprise a sidewall configured to contain a fluid. The sidewall of the bioreactor 510 may be coupled to a gas (e.g., air) permeable liner (not shown). Accordingly, the bioreactor 510 may be configured to retain a liquid while enabling a gas to flow through the sidewall. In some variations, the sidewall and/or gas permeable liner may be two-way permeable. In this way, the gas(es) within and around the bioreactor 510 may permeate such that equilibrium may be established between the bioreactor and adjacent components (e.g., one or more of the thermal compartments and mixing chamber). Additionally, or alternatively, the gas permeability of the sidewall may avoid a build of pressure within the bioreactor 510. For example, a relatively high pressure may permeate through the gas permeable liner to a location with a lower pressure. The bioreactor may further comprise a bottom having a concave shape. The concave shape of the bottom may help prevent cells or other material from sticking to an inner surface thereof. Additionally, the concave shape of the bottom surface may provide a cavity for receiving the impeller blades to help allow the impeller blades to agitate substantially all cells contained within the bioreactor 510.

Additional bioreactor modules and aspects thereof are provided in, e.g., U.S. Prov. Pat. App. No. 63/520,858, filed Aug. 21, 2023, the contents of which are hereby incorporated by reference herein in their entirety.

Magnetic Cell Sorter Module

A magnetic cell sorter (MCS) module may support one or more cell processing steps, such as one or both of selection and transduction. In general, the MCS module may include a flow cell (e.g., at least one flow cell, such as a plurality of flow cells, including two, three, four, or more than four flow cells) for facilitating positive and/or negative magnetic selection with one or both of microbeads and nanobeads. The flow cell may be disposed in proximity to a magnet array (e.g., permanent magnets, electromagnet) generating a magnetic field having a gradient across the flow cell to attract the labeled cells for separation, capture, recovery, and/or purification. The magnet array may be configured to generate non-uniform magnetic fields at the edges and the interfaces of the individual magnets so as to cover the full volume of the flow cell such that a magnetophoretic force equals a drag force exerted by the fluid flowing through the flow cell. In general, the MCS may be a column-free design configured to receive batches of a cell sample to process any volume of cells. Further, the MCS modules herein may include one or more additional fluid compartments, such as one or more of a first fluid compartment for storing the target cells (e.g., a target cell reservoir) and/or a second fluid compartment for storing waste (e.g., a waste reservoir), such as cellular waste. One or more flow cells of the MCS modules herein (e.g., flow cell 412 of FIG. 4B) may be fluidically coupled to each of the one or more additional fluid compartments, and/or fluidically coupled to each other, such as via tubing. For example, a flow cell may be fluidically coupled to each of a target cell reservoir and a waste reservoir.

A flow cell of an MCS module may be configured to hold a liquid volume of about 0.025 mL to about 25 mL, such as about 0.05 mL to about 20 mL, about 0.075 mL to about 15 mL, about 1 mL to about 10 mL, about 1.5 mL to about 9 mL, about 2 mL to about 8 mL, about 2.5 mL to about 7 mL, about 3 mL to about 6.5 mL, about 3.5 mL to about 6 mL, about 4 mL to about 5.5 mL, or about 4.5 mL to about 5 mL.

Moreover, each of the target cell reservoir and waste cell reservoir may be configured to how a liquid volume of about 0.5 mL to about 10 L, such as about 1 mL to about 9 L, about 10 mL to about 8 L, about 50 mL to about 7 L, about 100 mL to about 6 L, about 500 mL to about 5 L, about 600 mL to about 4.5 L, about 700 mL to about 4 L, about 800 mL to about 3.5 L, about 900 mL to about 3 L, about 1 L to about 2.5 L, or about 1.5 L to about 2 L (including all ranges and subranges in between).

Figure 4B:
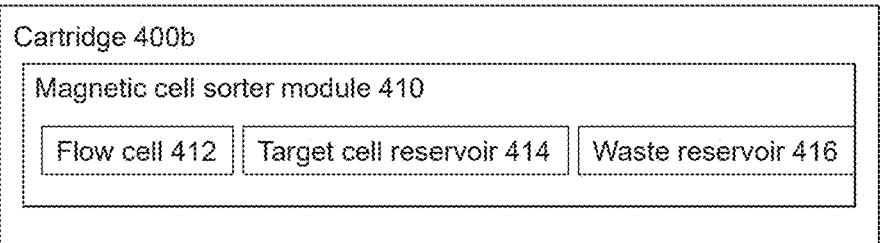
FIG. 4B is a block diagram of an illustrative variation of a cartridge having a magnetic cell sorter module.

FIG. 4B shows a block diagram of an exemplary MCS module 410 of a cartridge 400b for use with the systems, devices, and methods herein. The MCS module 410 may include a flow cell 412 and, in some variations, one or both of a target cell reservoir 414 and a waste reservoir 416. In some variations, fluid may be transferred between the flow cell 412, the target cell reservoir 414, and/or the waste reservoir 416 (e.g., from the flow cell 412 to the target cell reservoir 414 or the waste reservoir 416). Additionally, or alternatively, fluid may be transferred to and/or from another module of the cartridge 400b from and/or to any one of the flow cell 412, the target cell reservoir 414, and/or the waste reservoir 416.

Figure 6:
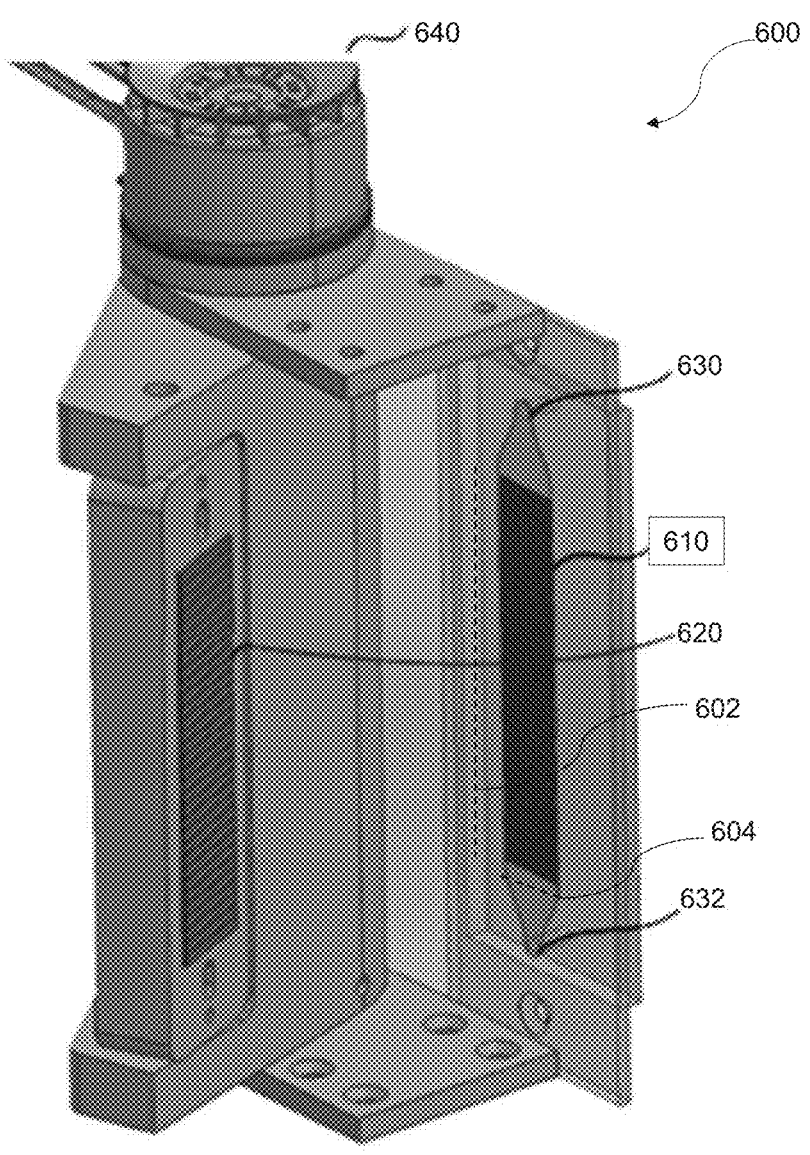
FIG. 6 is a rendering of a perspective view of an illustrative variation of a magnetic cell sorter module of a cartridge.

FIG. 6 is a perspective view of an exemplary MCS module 600. The MCS module 600 may include a flow cell 610 including an elongate cavity having an inlet 630 and an outlet 632. In some variations, the MCS module 600 may further comprise a magnet array 620 comprising a plurality of magnets. In some variations, the magnet array 620 may be external to the MCS. For example, the magnet array 620 may be a component of a cell sorting instrument of a workcell. The cavity of the flow cell 610 may comprise a cavity height 602 and a cavity width 604. In some variations, a ratio of the cavity height 602 to the cavity width 604 may be about 20:1 to about 1:20, about 10:1 to about 1:10, about 5:1 to about 1:5, or about 3:1 to about 1:3, including all values and subranges in-between. In some variations, the cavity of the flow cell 610 may have a first side and a second side to bring samples through the cavity. The first and second sides of the flow cell 610 may each be configured to hold a volume (e.g., a same or different volume) of fluid therein. Fluid may be configured to flow through the flow cell 610 in a first direction 606.

In some variations, one or more flow cells of an MCS module may have a label attached thereto. The label may include one or more features, such as one or more holes or other geometrical features, which may be detected by a vision system (e.g., vision system(s) 170 of FIG. 1A) during a calibration procedure (e.g., using a calibration cartridge) to compensate for misalignment between a cartridge and the vision system.

Additional MCS modules and aspects thereof are provided in, e.g., U.S. Prov. Pat. App. No. 63/520,861, filed Aug. 21, 2023, the contents of which are hereby incorporated by reference herein in their entirety.

Counterflow Centrifugal Elutriation Module

Counterflow centrifugal elutriation (CCE) combines centrifugation with counterflow elutriation, where the centrifugation corresponds to the process of sedimentation under the influence of a centrifugal force field and the counterflow elutriation corresponds to the process of separation by washing. Separation takes place in a cone (e.g., bicone, funnel) shaped elutriation chamber. Particles (e.g., cells) conveyed in a fluid into the elutriation chamber are acted upon by two opposing forces: centrifugal force driving the fluid away from an axis of rotation; and fluid velocity driving the fluid towards the axis of rotation (e.g., counterflow). By varying the flow rate and the centrifugal force, the separation of particles (e.g., cells) may be achieved. For example, particles may be separated based on properties such as size and density.

Counterflow centrifugal elutriation may perform multiple operations useful for cell therapy manufacturing workflows including, but not limited to, cell washing, cell concentration, media/buffer replacement and exchange, transduction, and separation of white blood cells from other blood components (e.g., platelets, and red blood cells). In some variations, a fluid source (e.g., apheresis bag) for a cell separation process may comprise a suspension of white blood cells, red blood cells, platelets, and plasma. In order to separate immune cells of interest, white blood cells may be isolated and subsequently magnetically tagged for magnetic separation. A white blood cell separation step may be performed in a CCE module to separate cells based on size and density, while magnetic separation may be performed in a MCS module, as discussed above. In some variations, a CCE module may be integrated into a cartridge to enable a cell processing system to separate cells based on one or more of a progression through a cell cycle (e.g., $G_1/M$ phase cells being larger than $G_0$, S, or G2 phase cells) and cell type (e.g., white blood cells from red blood cells and/or platelets).

Figure 4C:
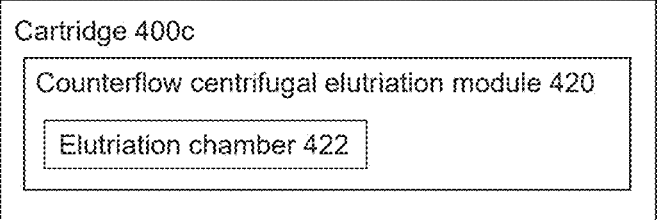
FIG. 4C is a block diagram of an illustrative variation of a cartridge having a counterflow centrifugal elutriation module.
Figure 4D:
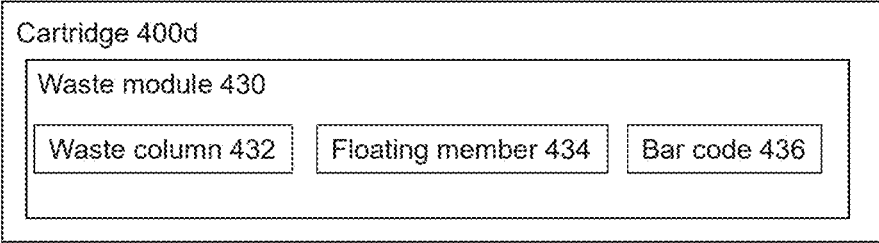
FIG. 4D is a block diagram of an illustrative variation of a cartridge having a waste module.

Accordingly, the CCE modules herein may include a fluid compartment, such as an elutriation chamber or a plurality thereof. As shown in FIG. 4C, a cartridge 400c may include CCE module 420, which includes elutriation chamber 422. The elutriation chamber 422 may be shaped as a cone or a bicone. In some variations, the CCE modules herein may include a rotor that configured to spin, where the rotor is integrally formed with the elutriation chamber (or other fluid compartment). A fluid comprising a suspension of cells may be pumped under continuous flow into the rotor. As cells are introduced into the cone (e.g., bicone), the cells migrate according to their sedimentation rates to positions in the gradient where the effects of the two forces upon them are balanced. Smaller cells having low sedimentation rates (e.g., platelets) may be quickly washed toward the axis of rotation with increased flow velocity. Such smaller cells may be output (e.g., washed out) of the cone. Relatively larger (or denser) cells (e.g., red blood cells) flow through the cone relatively more slowly and reach equilibrium at an elutriation boundary where the centrifugal force and the drag force are in balance, and the fluid velocity is relatively low because the cone has widened. The largest or densest cells (e.g., white blood cells) remain near the inlet to the chamber where centrifugal force and fluid velocity are high. By increasing the flow rate in gradual steps, successive fractions of increasingly large or dense cells (e.g., platelets→red blood cells→white blood cells) may be output from the rotor. Continued incremental increases in fluid flow rate will eventually elutriate all cells from the cone.

Figure 7:
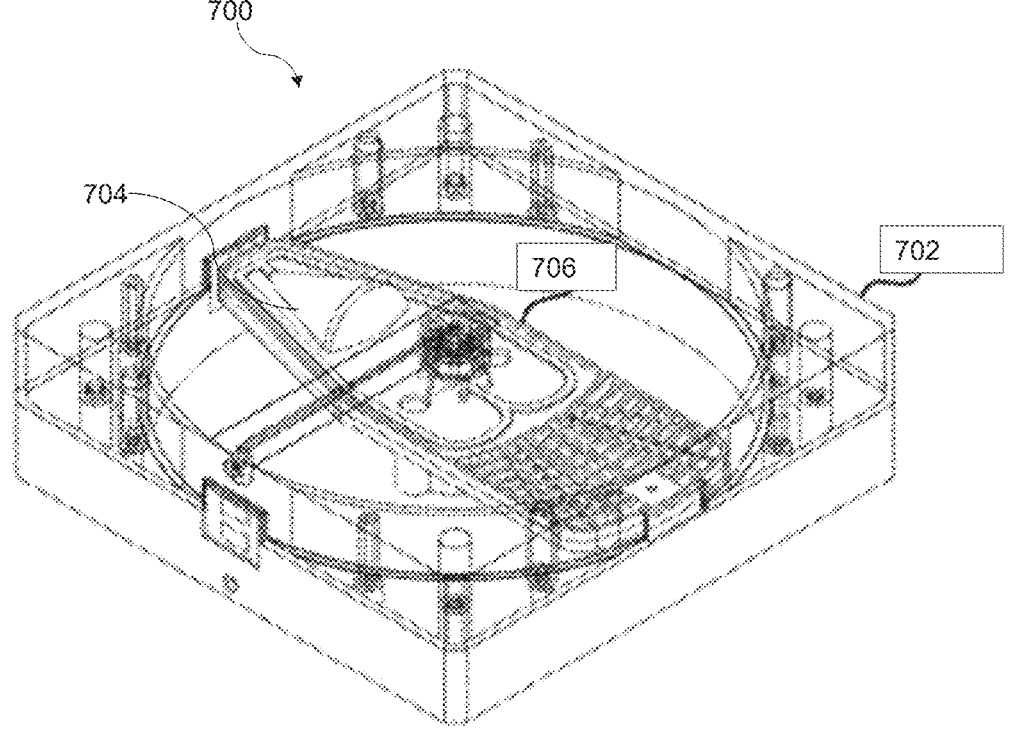
FIG. 7 is a depiction of a perspective view of an illustrative variation of a counterflow centrifugal elutriation module of a cartridge.

FIG. 7 is a perspective view of a CCE module 700 including a housing 702, an elutriation chamber 704, and a rotor 706. A CCE instrument may include a magnet configured to magnetically rotate the rotor 706. That is, the magnet may not be within the CCE module 700 of a cartridge. In some variations, the housing 702 may enclose the rotor 706. In some variations, the housing 702 may comprise one or more apertures configured to facilitate visualization (e.g., imaging) of the elutriation chamber 704 and/or the rotor 706.

Waste Module

The waste modules herein may generally include one or more fluid compartments, such as one or more waste columns for storing waste. For example, a waste column may be fluidically coupled to one or more other modules of a cartridge (e.g., a bioreactor module, an MCS module, CCE module, and/or the like) via a fluidic bus such that waste may be transferred throughout the cartridge and into the waste column. The waste column(s) of a waste module may be configured to hold a volume of fluid of about 0.5 mL to about 10 L, such as about 1 mL to about 9 L, about 10 mL to about 8 L, about 50 mL to about 7 L, about 100 mL to about 6 L, about 500 mL to about 5 L, about 600 mL to about 4.5 L, about 700 mL to about 4 L, about 800 mL to about 3.5 L, about 900 mL to about 3 L, about 1 L to about 2.5 L, or about 1.5 L to about 2 L (including all ranges and subranges in between). Moreover, the waste modules herein may include a barcode and/or a radio-frequency identification tag (RFID) for identifying one or both of the waste module and the cartridge housing the waste module. For example, a robot of the systems herein (e.g., robot 116 of FIG. 1A) may be configured to scan a barcode and/or RFID tag for precise handling of the cartridge and/or of one or more waste columns of a waste module thereof. As another example, a vision system of one or more cell processing instruments (e.g., instrument(s) 112 of FIG. 1A) may be configured to monitor barcode and/or RFID tag during a cell processing operation in order to categorize the data detected and/or generated during the cell processing operation (e.g., to assign the data to a particular cartridge). In some variations, a calibration cartridge may include one or more fiducial markers (e.g., 1, 2, 3, 4, 5, or greater than 5 markers) defining a barcode region of the calibration cartridge. As will be described herein, a calibration procedure may use a vision system of an instrument to define an ROI that includes the barcode region (e.g., a waste and barcode region) such that a barcode of a cell processing cartridge that is subsequently engaged with the instrument may be identified by the vision system. Additionally, or alternatively, the waste modules herein may include a floating member configured to float at (e.g., through) or proximal to a liquid surface of the waste within the module in order to facilitate tracking of a liquid level within the waste modules (e.g., within one or more waste columns thereof). For example, a controller (e.g., controller 120) communicably coupled to a vision system imagining a given waste module may be configured to determine an outline and/or size of the floating member, and with this, an accurate, real-time liquid level within the waste column (as will be described in detail herein).

In some variations, the waste modules herein may be utilized within one or more instruments of a workcell, such as within all bioprocessing and/or liquid transfer instruments of a workcell. That is, waste may be transferred from a first module (e.g., a bioreactor, MCS, CCE, or other module) to the waste module when the cartridge is within any cell processing instrument (e.g., a bioreactor instrument, an MCS instrument, a CCE instrument, or other instrument). In some variations, a cartridge may include one or more waste modules, such as a plurality thereof. In some variations, a waste module may be a part of another module of a cartridge. In particular, one or more other modules of the cartridge may include individual waste columns. For example, each of one or more of an MCS module, CCE module, bioreactor module, and EP module itself may comprise an associated waste column.

FIG. 8A is a perspective view of an exterior of a waste module 800. The waste module 800 may include a waste column 802a and a barcode region 804. In some variations, a barcode and/or RFID tag may be within the barcode region 804. For example, a cell processing cartridge may include a barcode within the barcode region 804. In some variations, the waste module 800 may include one or more fiducial markers for defining a ROI of the waste module 800 to monitor during one or more cell processing operations. For example, as shown in FIG. 8, the waste module 800 may include first and second markers 806, 808 defining a barcode region to visualize during cell processing, as well as third and fourth markers 810, 812 defining a waste region (e.g., the waste column 802) to visualize during cell processing. Further, the waste module 800 may include one or more fiducial markers to encode a vision system identification (e.g., a camera identification for one or more cameras of a vision system of an instrument), such as fifth marker 814 shown in FIG. 8A. Moreover, FIG. 8B is a stylized, cross-sectional view of a waste column 802*b*. As shown, the waste column 802*b* may carry a floating member 820 therein. As explained in detail below, the floating member 820 may be configured to float at a liquid surface 822 of the liquid waste within the waste column 802*b* such that a liquid level of the liquid surface 822 may be accurately calculated (e.g., by a controller).

Workcell

The workcell(s) of the automated cell processing systems herein may be configured to receive one or more cartridges for processing (e.g., for parallel processing of a plurality of cartridges). A workcell may include an enclosure defining a housing or interior zone and one or more feedthrough accesses for transferring cartridges in and out of the interior zone. The workcell may also include a plurality of instruments (e.g., disposed in the interior zone), such as one or more bioprocessing instruments, including one or more of a bioreactor instrument, a magnetic cell selection (MCS) instrument, a cell sorting instrument (e.g., FACS), an electroporation (EP) instrument, a counterflow centrifugation elutriation (CCE) instrument, and one or more liquid transfer instruments (e.g., one or more sterile liquid transfer instruments). Generally, each of the instruments within a workcell may interface with its respective module or modules on the cartridge. For example, to perform a cell processing operation with the bioreactor module of a cartridge, the cartridge may be moved (e.g., by a robot) to a bioreactor instrument of the workcell to perform the operation. The workcell may further include one or both of a reagent vault for storing reagents for cell processing and a sterilization system for sterilizing cartridges and/or fluid devices.

Figure 9A:
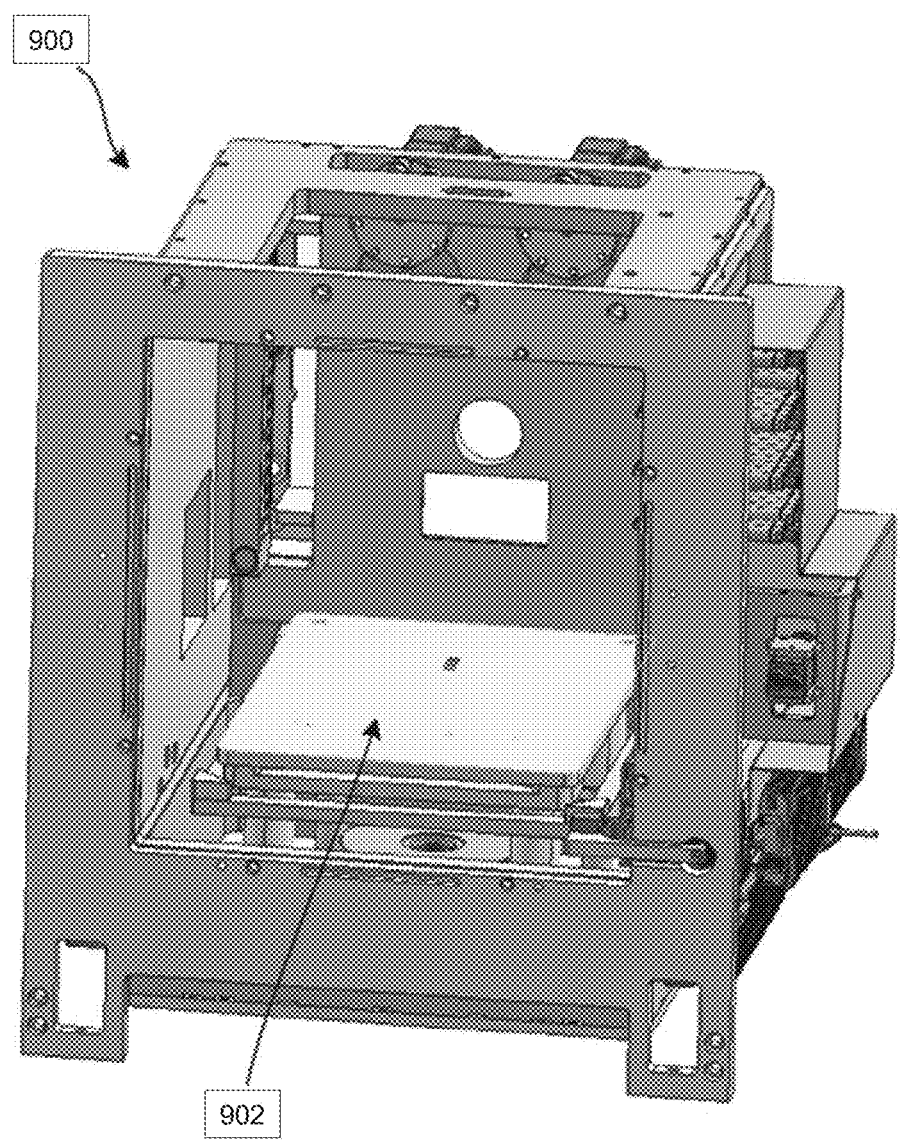
FIG. 9A is a rendering of a perspective view of an illustrative variation of an instrument of a workcell.
Figure 9B:
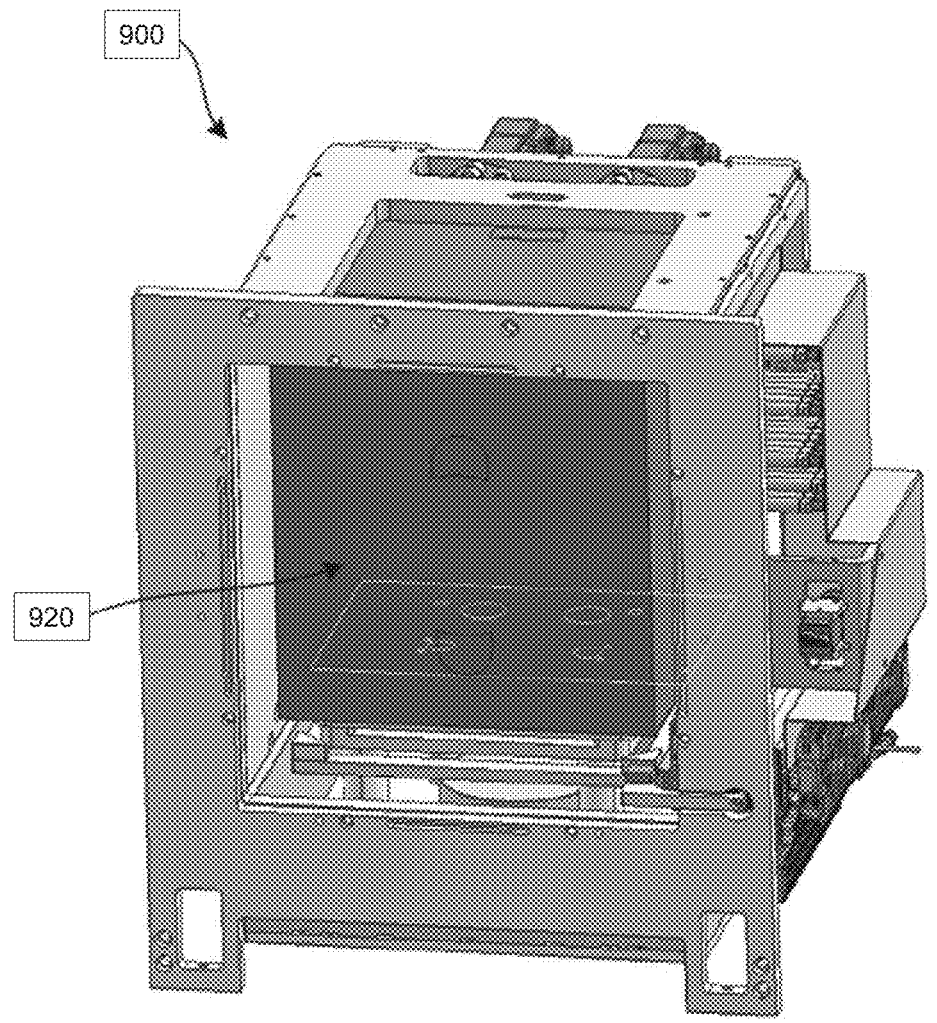
FIG. 9B is a rendering of a perspective view of an illustrative variation of a cartridge within the instrument of FIG. 9A.

Each instrument of a workcell may be configured to interface with (e.g., mechanically and/or electrically) a cartridge to perform one or more cell processing steps on the cells within the cartridge (and/or to perform a calibration procedure using the cartridge). FIGS. 9A-9B are exemplary perspective views of a cell processing instrument 900 configured to interface with a cartridge (e.g., cartridge 920 of FIG. 9B). The instrument 900 may include an enclosure 902 configured to support a plurality of components (e.g., one or more sensor(s), pump(s), magnet(s), etc.) that enable the instrument 900 to interface with a cartridge and perform one or more cell processing steps. For example, the enclosure 902 may have walls (e.g., three sidewalls, a base, and/or a ceiling, as shown in FIG. 9A) that support the plurality of components thereon and/or therein. That is, each of the components of the instrument 900 may be mounted on or within the enclosure 902. The enclosure 902 may be constructed at least in part of a rigid or semi-rigid material for structurally supporting the components of the instrument 900. In some variations, the enclosure 902 may support a vision system (not shown) including one or more sensors (e.g., cameras) for monitoring liquid levels and/or flow rates and paths within a cartridge (e.g., cartridge 920) during cell processing. The vision system may additionally include one or more light sources for illuminating a region-of-interest (ROI) of a cartridge, and/or one or more mirrors for directing light to the sensors of the vision system. For example, each sensor of the vision system may include one or more light sources (e.g., 1, 2, 3, 4, 5, or more than 5 light sources) for illuminating at least a portion of a module of a cartridge (e.g., cartridge 920) within the instrument 900.

Vision System

As discussed herein throughout, one or more of the workcell instruments herein may include a vision system (e.g., vision system 170 of FIG. 1A) for detecting and/or generating liquid level and/or fluid transfer data for cell processing cartridges (e.g., within one or more modules thereof) during cell processing. In general, the vision systems described herein may be operably coupled to one or more controllers of a workcell (e.g., controller 120 of workcell 110). The vision systems may be configured to transmit (e.g., continuously or at a set or variable rate via one or both of a wired and wireless connection) data, such as image data, to the controller(s) to be analyzed, stored, processed, edited, visualized, transferred, and/or the like. Suitable controllers and aspects thereof for use with the vision systems above (and/or with other systems, devices, and methods herein) are described in more detail below.

For example, the vision systems herein may be configured to generate a series or sequence of images of at least a portion of a cartridge (e.g., a module or fluid compartment thereof) to determine (e.g., via a controller) one or more real-time liquid levels (i.e., volumes) fluid (e.g., liquid) flow rates, and/or fluid (e.g., liquid) flow paths within the cartridge. These determinations may be used (e.g., by the controller) to precisely fill the fluid compartments of the cartridge (e.g., by using feedback to achieve a desired liquid level) and/or to modify (e.g., speed up, slow down, or stop) fluid transfer. Additionally, or alternatively, the vision systems may be used during a calibration process (e.g., when a calibration cartridge is interfacing with an instrument) to compensate for distortion caused by the vision system (e.g., by camera lenses) and/or to compensate for misalignment between the calibration cartridge and the vision system (e.g., one or more sensors thereof). During the calibration procedure, one or more regions-of-interest (ROIs) of the cartridge (e.g., for monitoring liquid levels and/or volumes therein) may be defined for the vision system. Generally, each ROI may be defined (e.g., in two dimensions) along at least a portion of an exterior surface of a fluid compartment (or one or more fluid compartments of a same module). For example, each ROI may include at least one dimension (e.g., height) that is the about the same as a corresponding dimension of the fluid compartment so that the that the liquid level (e.g., surface level of liquid) within the fluid compartment may be accurately tracked by the vision system within the ROI. In some variations, a height of the ROI for a given fluid compartment may be about 60% to about 100% of the height of the container, such as about 65% to about 99%, about 70% to about 98%, about 75% to about 97%, about 80% to about 96%, about 85% to about 95%, about 86% to about 94%, about 87% to about 93%, about 88% to about 92%, about 89% to about 91%, or about 90% of the height of the container (including all ranges and subranges in between). In some variations, a width of the ROI for a given fluid compartment may be about 5% to about 100% of the width of the container, such as about 15% to about 90%, about 25% to about 80%, about 35% to about 70%, or about 45% to about 60% of the width of the container (including all ranges and subranges in between).

In general, the vision systems of the instruments herein may include one or more sensors, such as one or more cameras, for detecting and/or generating liquid level and/or fluid transfer data of cartridges interfacing with the instruments. For example, in some variations, a cartridge module configured to store (e.g., temporarily store) liquid therein may be monitored by at least one camera of the vision system. As another example, in some variations, at least one first camera may be configured to monitor a first ROI including a first subset of fluid compartments of the module, and at least one second camera may be configured to monitor a second ROI including a second, different subset of fluid compartments of the module. In another example, at least one first camera may be configured to monitor a first ROI including a first side of one or more fluid compartments of the module, and at least one second camera may be configured to monitor a second ROI including second, different (e.g., opposite) side of the one or more fluid compartments. As yet another example, at least one camera may be configured to monitor an ROI including one of a plurality of fluid compartments of the module. In some variations, an ROI defined for each of the plurality of fluid compartments of the module may be monitored by a corresponding unique camera of the vision system. In some variations, one or more modules (or fluid compartments thereof) being monitored by a vision system may contain a floating member configured to float proximal to (e.g., through) the liquid surface of liquid therein for facilitating determination of the liquid level. For example, a waste column of a waste module may be configured to store various types of liquids and thus different types of divide within the waste column. Additionally, there may be foam or bubbles produced by the waste liquid may obscure the liquid surface, complicating a tracking procedure (e.g., of the controller based on a liquid level detected by the vision system, as discussed below). Accordingly, the vision system may be configured to generate an output (e.g., a series of real-time images) including the floating member so that the liquid level of the waste column may be determined. Moreover, it should be understood that a configuration of a given vision system may be unique compared to the vision systems of other instruments of the workcell. That is, each vision system within a workcell may include a unique number of sensors, and/or each sensor may have a unique orientation and/or may be configured to monitor a unique ROI of a cartridge. In some variations, a configuration of one or more of the vision systems (e.g., all of the vision systems) of the workcell may have a same or similar configuration. Furthermore, in some variations, a configuration of the vision systems herein may be variable and/or adjustable. For example, one or more sensors of a vision system may be movable (e.g., translatable and/or rotatable relative to a wall of the enclosure of the instrument supporting the system), such that the one or more sensors may monitor a plurality of ROIs throughout a cell processing operation. In some variations, when a fluid transfer is initiated within the cartridge (e.g., automatically by a controller of the system) or selected (e.g., by an operator of the system), one or more cameras of the associated vision system may be triggered to observe an origin fluid compartment and/or destination fluid compartment of the fluid transfer. In some variations, triggering these observations may include instructing (e.g., via a controller) the one or more cameras to reposition itself to gain visual access to the origin and/or destination fluid compartment Moreover, the vision systems herein may be configured to continuously detect liquid level and/or fluid transfer data, and/or may be configured to discretely collect the data at a constant or varied rate (which may be adjustable by a controller of the system and/or an operator). For example, one or more liquid levels and/or fluid transfer parameters may be detected by a vision system at a rate of 1 Hz to 50 MHz, such as at a rate of 50 Hz to 30 MHz, 100 Hz to 10 MHz, 500 Hz to 5 MHz, 1 KHz to 1 MHz, 50 KHz to 500 KHz, or 100 KHz to 250 KHz (including all ranges and subranges in-between).

Furthermore, the vision systems herein may additionally include one or more light sources, mirrors, prisms, and/or polarizers. For example, a vision system may include a plurality of cameras, where each of the plurality of cameras includes at least one light source for illuminating a portion of a cartridge, and where a subset (e.g., all or fewer than all) of the cameras include associated mirrors and/or polarizers for directing light to the cameras. Each camera of the plurality of cameras may include a lens and an aperture. Each lens may be configured to provide a normal or wide-angle view of a cartridge. For example, a lens having a focal length of between about 35 mm and about 50 mm may be used to provide a normal-angle view of a portion of the cartridge. As another example, a lens having a focal length of between about 8 mm and about 18 mm may be used to provide a wide-angle view of a portion of the cartridge. In some variations, one or more mirrors, polarizers, and/or prisms associated with a camera (e.g., in the optical path of the camera) may be supported by the instrument. Additionally, or alternatively, in some variations, one or more mirrors, polarizers and/or prisms associated with a camera may be supported by a cartridge. One or more light sources associated with a camera of the vision system may be configured to illuminate a liquid surface within the cartridge. Accordingly, an optical path for the camera may originate from one or more light sources, pass through liquid surface (s), then through one or more walls of the cartridge (e.g., a fluid compartment wall and/or an exterior wall thereof), then (optionally) through one or more walls of the instrument (e.g., through a panel protecting the camera, such as an acrylic panel), then through the camera lens and aperture and to the image sensor of the camera. Additionally, in some variations, an optical path for one or more of the cameras of the vision system may include one or more mirrors, prisms, and/or polarizers (e.g., positioned between the cartridge fluid compartment wall and the camera lens) for reflecting, separating, and/or filtering the light from the light source to the image sensor. Moreover, in some variations, a vision system for each instrument of a workcell may be operably coupled to a controller of the workcell (e.g., controller 120 of FIG. 1A). As discussed in detail below, the controller may display (e.g., via display 130 of FIG. 1A) the data collected and/or generated by the vision systems so that an operator may have access to the data (e.g., for viewing and/or modification).

Turning to FIG. 10, a stylized, exemplary variation of an instrument 1000 with a vision system is shown. The instrument 1000 includes a vision system (e.g., mounted within the instrument 1000) with at least one camera 1002*a,b,c,d, e,f* and at least one associated light source 1012*a,b,c,d,e,f,g* for imaging each of a bioreactor (BR) module 1004, an MCS module 1006, a CCE module 1008, and a waste module 1010 of cartridge 1001. Each of the cameras 1002*a,b,c,d,e,f* may be oriented such that they are opposing a module (or a portion thereof) where liquid is contained so that each camera has visual access to a liquid level within the module. In particular, camera 1002*a* and light source 1012*a* may be used to image the waste module 1010 (e.g., a waste column and barcode thereof). Additionally, two cameras 1002*b,c* and light sources 1012*b,c* may be used to image first and second sides of the BR module 1004. Camera 1002*b* imagining the first side (i.e., side A) of the BR module 1004 may be focused on a first ROI of the BR module 1004 including at least portion of one or more fluid compartments of the BR module 1004, such as at least a portion of one or more of a bioreactor, a mixing chamber, and one or more thermal compartments (e.g., 1, 2, 3, 4, 5, 6, 7, 8, 9, 10, or more than 10 thermal compartments) of the BR module 1004. Similarly, camera 1002*c* imagining the second side (i.e., side B) of the BR module 1004 may be focused on a second ROI of the BR module 1004 including at least portion of one or more same and/or different fluid compartments of the BR module 1004, such as at least a portion of one or more of the bioreactor, the mixing chamber, and one or more same or different thermal compartments (e.g., 1, 2, 3, 4, 5, 6, 7, 8, 9, 10, or more than 10 same or different thermal compartments) of the BR module 1004. In some variations, the camera 1002*b* may be configured to image three thermal compartments of the BR module 1004, and the camera 1002*c* may be configured to image three different thermal compartments of the BR module 1004. Next, two cameras 1002*d,e* and light sources 1012*d,e* may be used to image first and second sides of the MCS module 1006. Camera 1002*d* imaging the first side (i.e., side A) of the MCS module 1006 may be focused on a first ROI of the MCS module 1006 including at least a portion of one or more fluid compartments thereof, such as a target cell reservoir or a flow cell of the MCS module 1006. Likewise, camera 1002*e* imaging the second side (i.e., side B) of the MCS module 1006 may be focused on a second ROI of the MCS module 1006 including at least a portion of one or more fluid compartments thereof, such as a waste reservoir or a flow cell of the MCS module 1006. Further, camera 1002*f* and light sources 1012*f,g* may be used to image at least a portion of the CCE module 1008, such as an elutriation chamber of the CCE module 1008.

Figure 10A:
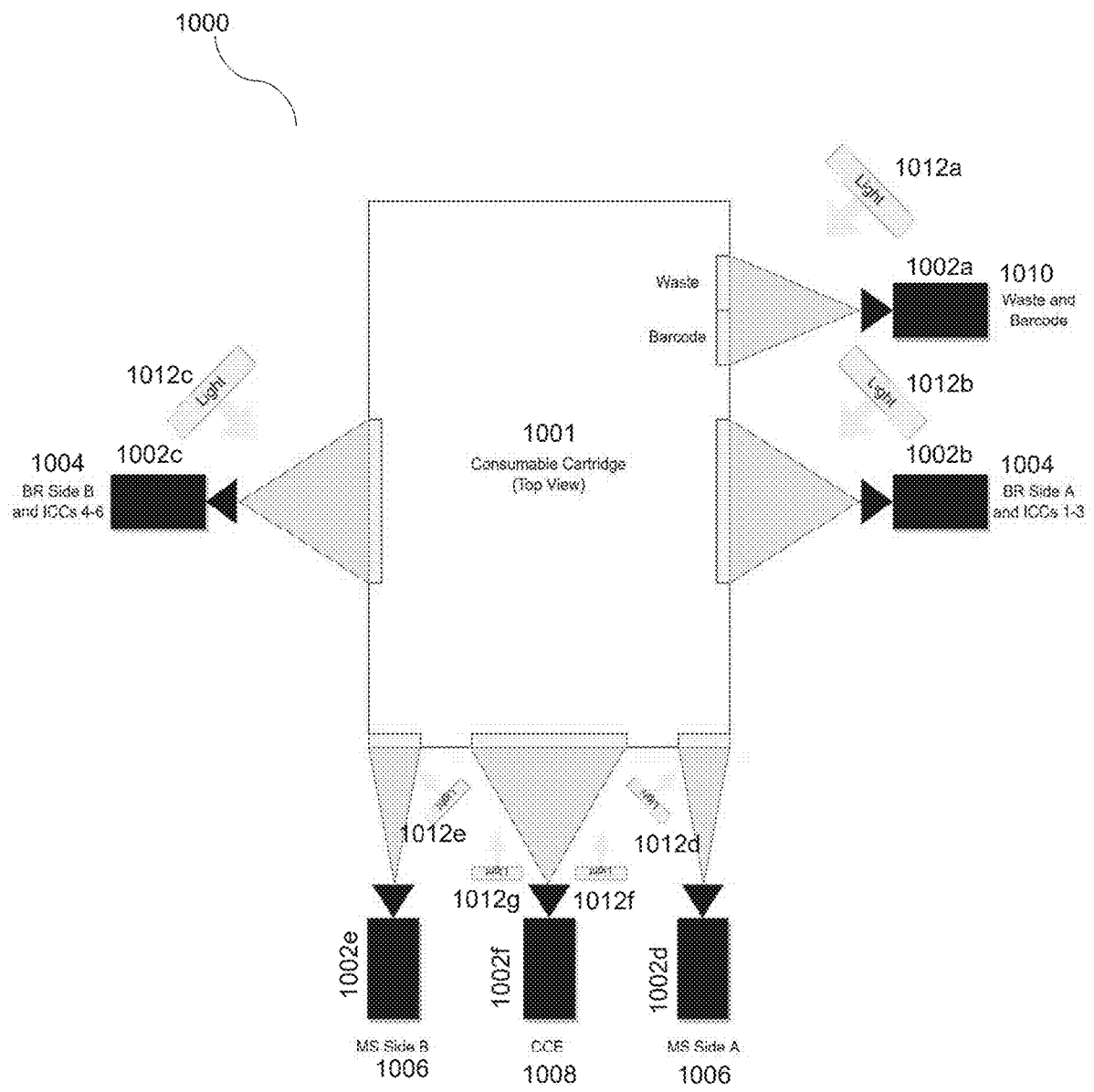
FIG. 10A is a stylized depiction of a top view of an illustrative variation of a vision system of an instrument directed toward a cartridge interfacing with the instrument.
Figure 10B:
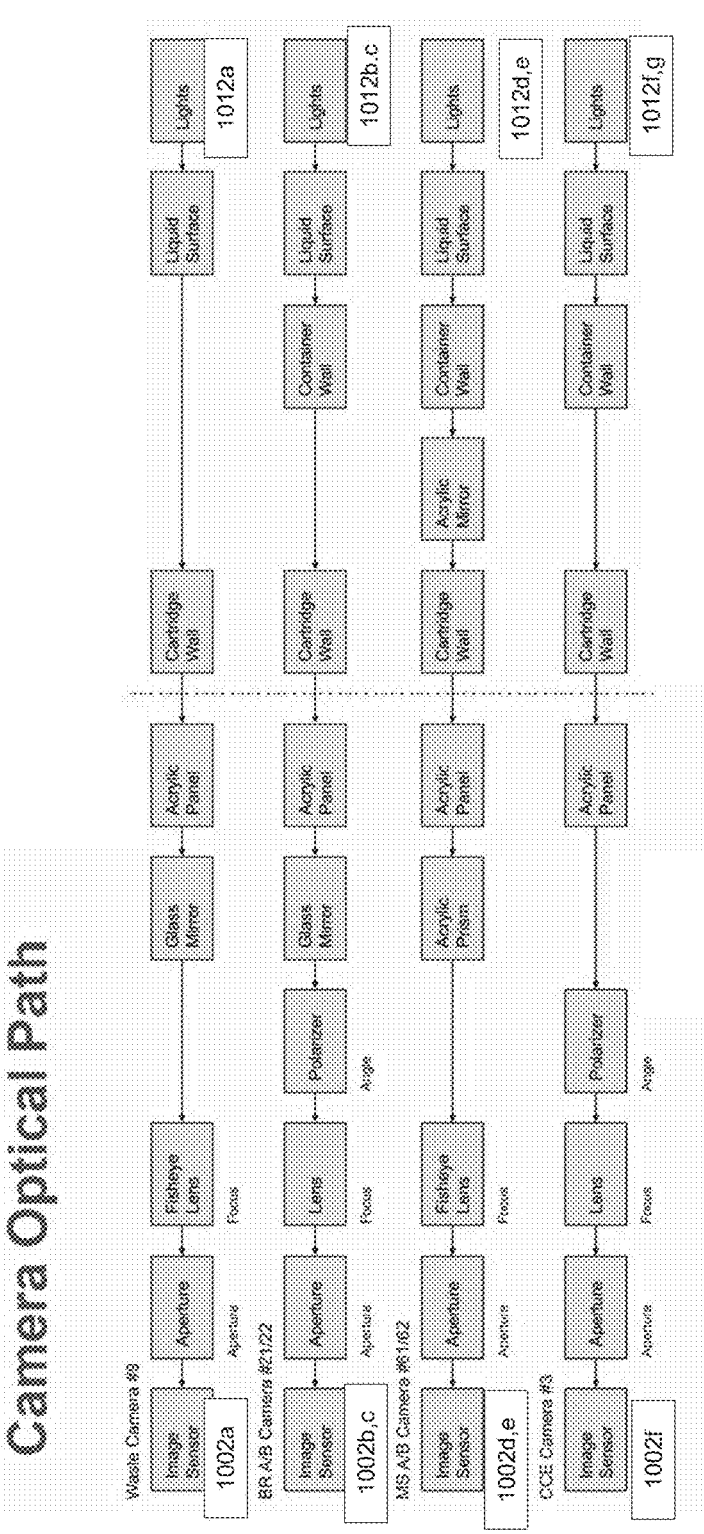
FIG. 10B is a flow diagram illustrative variations of optical paths of the vision system of FIG. 10A.

FIG. 10B depicts flow diagrams of exemplary optical paths of the cameras 1002*a,b,c,d,e,f* of FIG. 10A. As shown, an optical path for the camera 1002*a*, which images the waste module 1010, may originate at the light source 1012*a*, then pass through a liquid surface within the waste module 1010 (e.g., within a waste column thereof), then through an exterior wall thereof of the cartridge (e.g., cartridge 1001 of FIG. 10A), then through an acrylic panel of the instrument (e.g., instrument 1000 of FIG. 10A), then, via a mirror, through the camera lens and aperture and to the image sensor of the camera 1002*a*. Additionally, an optical path for each of the cameras 1002*b,c*, which image the BR module 1004, may originate at the light sources 1012*b,c*, then pass through liquid surface(s) within the BR module 1004 (e.g., within one or more fluid compartments thereof), then through one or more fluid compartment walls, through an exterior wall of the cartridge, through an acrylic panel of the instrument, then, via a mirror, through a polarizer of the instrument, and through the camera lens and aperture to the image sensor of the cameras 1002*b,c*. Moreover, an optical path for each of the cameras 1002*d,e*, which image the MCS module 1006, may originate at the light sources 1012*d,e*, then pass through liquid surface(s) within the MCS module 1006 (e.g., within one or more fluid compartments thereof), then through one or more fluid compartment walls, then, via a mirror of the cartridge, through an exterior wall of the cartridge, then through an acrylic panel of the instrument, then, via a prism, through the camera lens and aperture and to the image sensor of the cameras 1002*d,e*. Further, an optical path for the camera 1002*f*, which images the CCE module 1008, may originate at the light sources 1012*f,g*, then pass through to a liquid surface within the CCE module 1008 (e.g., within an elutriation chamber thereof), then through an exterior wall thereof of the cartridge, through an acrylic panel of the instrument, then through a polarizer of the instrument, and finally through the camera lens and aperture and to the image sensor of the camera 1000*f*.

Figure 18A:
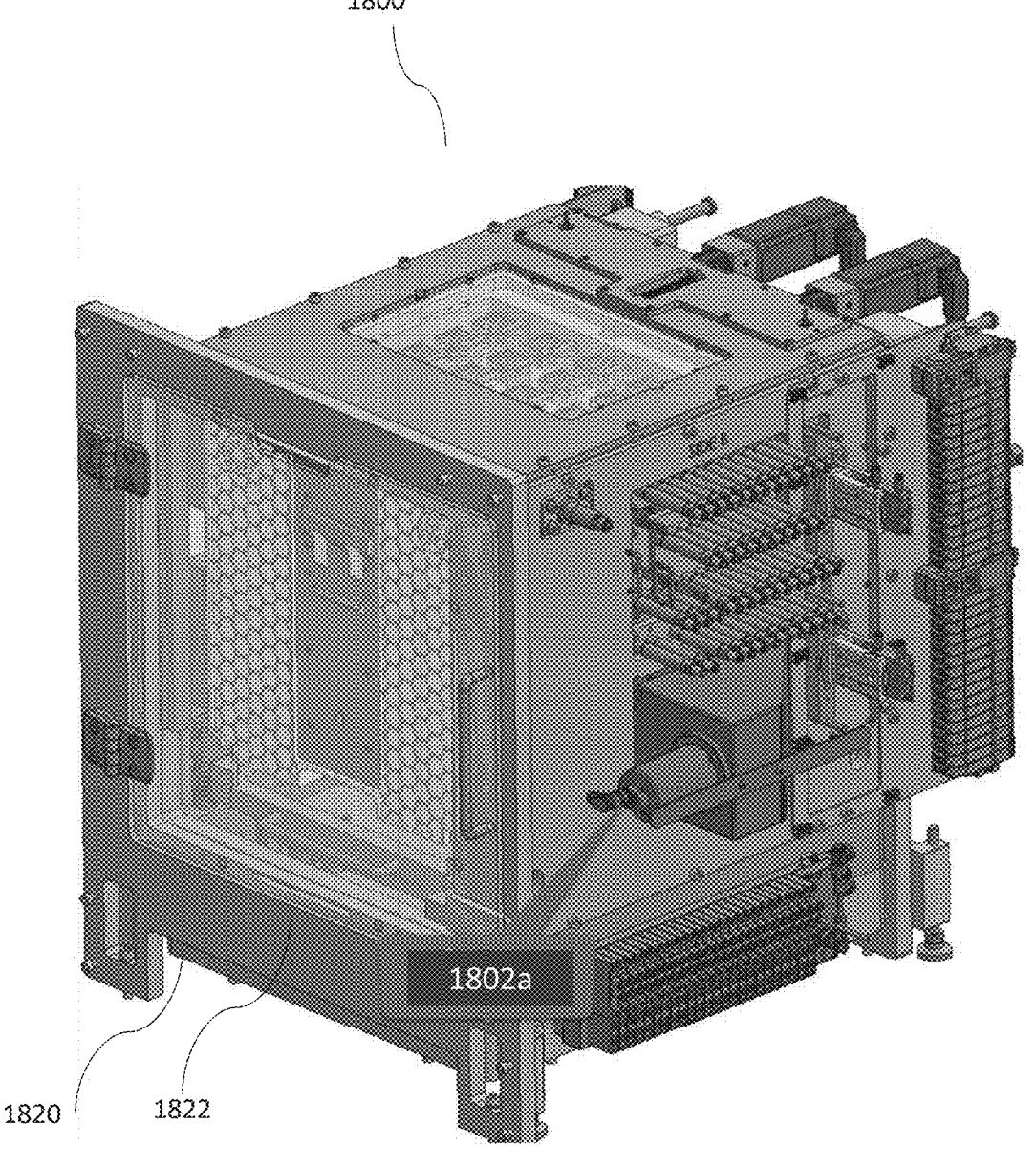
FIG. 18A is a rendering of a first side view of an exemplary instrument of a workcell.
Figure 18B:
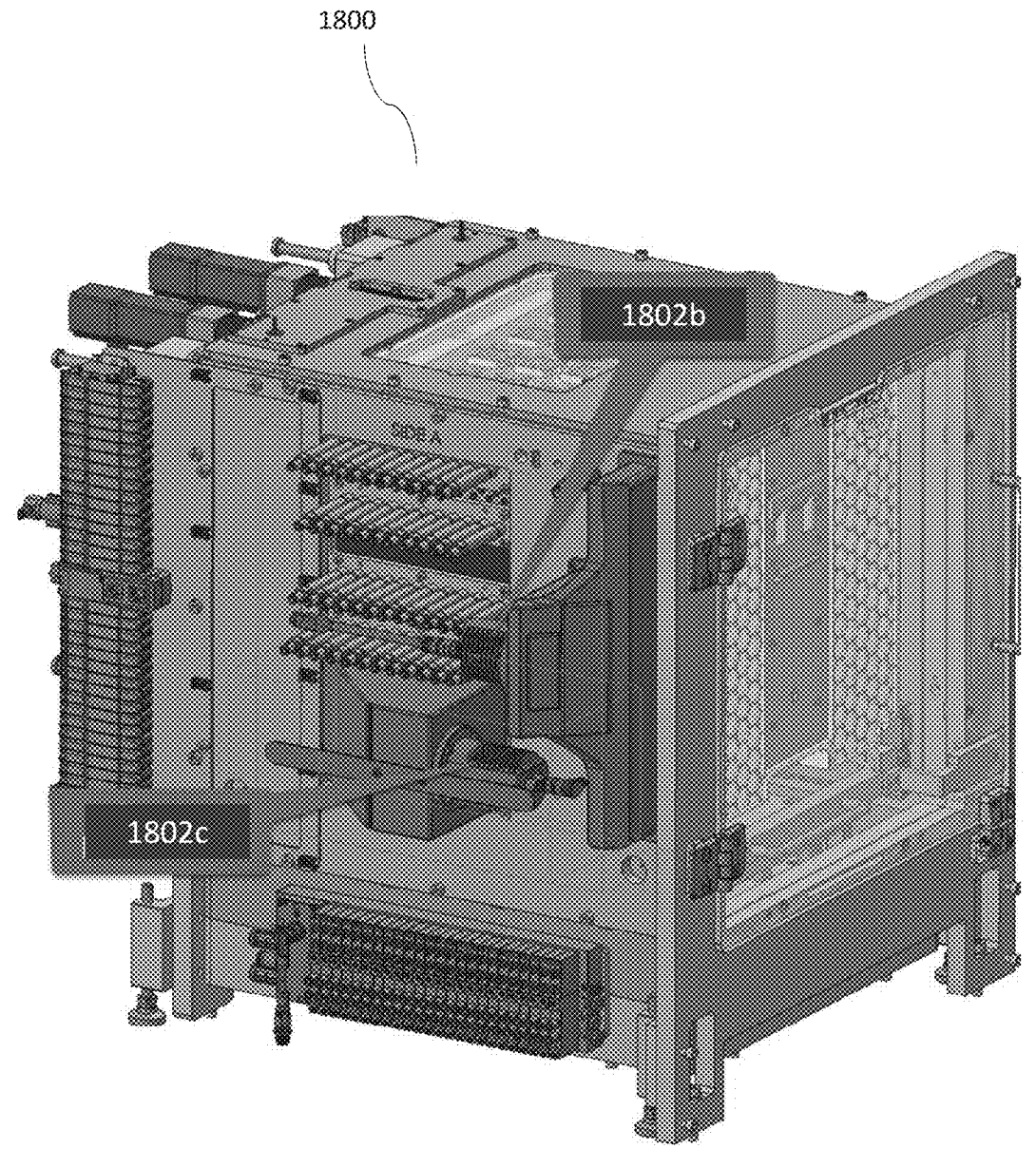
FIG. 18B is a second side view of the exemplary instrument of FIG. 18A.
Figure 18C:
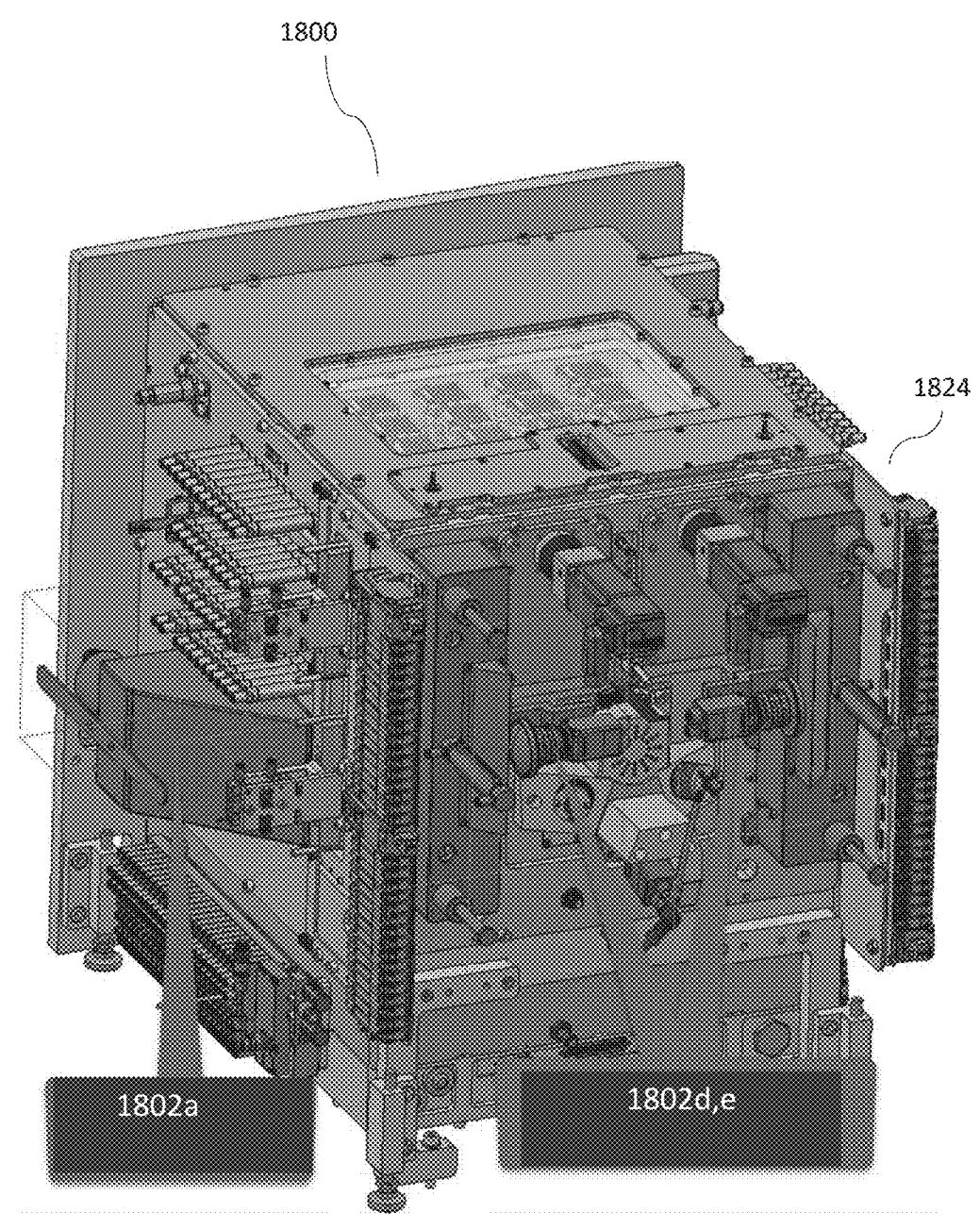
FIG. 18C is a back view of the exemplary instrument of FIGS. 18A and 18B.

Another exemplary vision system mounted on an instrument 1800 is shown in FIGS. 18A-18C. A front side 1820 (e.g., shown in FIGS. 18A-18B) of the instrument 1800 may include a feedthrough 1822 to receive a cartridge (e.g., cartridge 300 of FIG. 3). A back side 1824 (e.g., shown in FIG. 18C) of the instrument 1800 may be opposite the front side 1820, and may be within a sidewall of an enclosure of a workcell (e.g., workcell 202 of FIG. 2). As shown in FIG. 18A, a camera 1802*a* may be situated on a first sidewall 1804 on a first side of the instrument 1800. The camera 1802*a* may be configured to observe a first portion (e.g., a first side of one or more fluid compartments) of a bioreactor module within a cartridge (e.g., a first bioreactor module thereof). As shown in FIG. 18B, two cameras 1802*b,c* may be mounted on a second sidewall 1806 on a second side of the instrument 1800. The camera 1802*b* may be configured to observe the first portion (e.g., a second side of one or more fluid compartments) of the bioreactor module. The camera 1802*c* may be configured to view a second portion (e.g., one or more same or different fluid compartments viewed by cameras 1802*a,b*) of the bioreactor module. Finally, as shown in FIG. 18C, cameras 1802*d,e* may be mounted on the back side 1824 of the instrument 1800. The cameras 1802*d,e* may be configured to view first and second sides, respectively, of an MCS module within a cartridge (e.g., first and second sides of a flow cell thereof).

As exemplified in FIGS. 10A-10B and FIGS. 18A-18C, the vision systems herein may be configured to detect a liquid level (e.g., at least one liquid level) within one or more ROIs of a cartridge via one or more sensors (e.g., cameras) that are directed toward a ROI (e.g., for visual access) and/or toward an optical path originating at an ROI. While the exemplary variations of vision systems above may describe specific numbers of sensors, light sources, and other components (e.g., mirrors, polarizers and/or prisms) thereof, it should be understood that the vision systems herein may be equipped with any number or combination of sensors, light sources, and other components. For example.

Generally, the data output by the vision systems herein may be image data comprising one or more ROIs and associated liquid levels. For example, the data may include a real-time image of an ROI and associated liquid level(s), and/or a series of images of an ROI and associated liquid level(s). As is described herein throughout, the vision systems herein may be operably coupled to a controller (e.g., controller 120 of FIG. 1A), and may be configured to transmit some or all of the liquid level detections to the controller. The controller may then use the data provided to determine one or more real-time liquid levels within the cartridge, as is described in detail below (e.g., with respect to FIGS. 12 and 13A-13B).

Additionally, the vision systems herein may be configured to verify parameters of fluid transfer within cartridges, and/or may be used within active feedback systems for controlling fluid transfer within the cartridges. In some variations, a vision system may be configured to verify one or both of a flow rate and/or flow path of fluid transfer within a cartridge (e.g., from a first module to a second, different module). The vision system may be configured to verify the flow rate of a fluid transfer step by detecting motion of a pump configured to interface with the cartridge to actuate the fluid transfer therein (e.g., pump 138 of FIG. 1A). That is, an operational speed (e.g., rotational speed) of the pump may correspond to the flow rate of fluid transfer. In general, the operational speed of the pump may be controlled by a controller (e.g., controller 120 of FIG. 1A). Thus, when the pump is operating (e.g., in motion), the flow rate of fluid transfer within the cartridge may be known. The vision system may be configured to verify this known (e.g., desired) flow rate to ensure that the fluid transfer step is proceeding as planned. For example, the vision system (e.g., one or more sensors thereof) may be configured to detect a rotor of the pump and generate an output (e.g., image data) of the rotor that may be used (e.g., by the controller) to calculate the real-time operational speed of the pump.

Additionally, or alternatively, the vision system (e.g., one or more same or different sensors thereof) may be configured to verify that the path of fluid transfer is a desired path (selected by, e.g., the controller and/or an operator). For example, as explained above, the vision system may be configured to monitor an origin and/or destination module of the fluid transfer to verify the fluid path. More specifically, one or more sensors of the system may be configured to detect the liquid level within one or both of the origin and destination module to verify that fluid is transferring out of the origin module (e.g., via a decreasing liquid volume) and/or into the destination module (e.g., via an increasing liquid volume). As discussed below, a controller may analyze the outputs of the one or more sensors to determine whether the liquid volumes of the origin and/or destination module are transferring accurately (e.g., are increasing or decreasing as planned).

In some variations, the vision system may be configured to monitor the liquid level in the origin and/or destination modules throughout some or all of a duration of the fluid transfer, and to transmit to the controller an output (e.g., an image or series thereof) of the changing liquid level(s) over the duration so that the controller may calculate the flow rate of the transfer using recorded (e.g., within a memory, such as memory 124 of FIG. 1A) liquid level measurements based on the changing liquid level(s) detected by the vision system (discussed in further detail below).

Further, data output by the vision system may be used to control filling of one or more modules or fluid compartments of a cartridge. For example, image data (e.g., a real-time image or series thereof) of a liquid level of a fluid compartment (e.g., of a flow cell of an MS module) of the cartridge may be used (e.g., by controller 120 of FIG. 1A) to determine when a liquid level condition of the fluid compartment is met, such as when a desired fill level of the fluid compartment is achieved. As discussed in more detail below, in some variations, a current fill level (i.e., real-time or near real-time liquid level) within the fluid compartment may be continuously updated, or updated at a fast rate, using data generated by the vision system. The current fill level may be compared to the desired fill level after each update, or periodically at a predetermined time interval. In some variations, when the current fill level is determined to be about equal to the desired fill level, the fluid transfer may be stopped (e.g., a flow rate thereof may be reduced or stopped).

In another example, a liquid level condition may include a depletion level for one or more modules (e.g., one or more fluid compartments thereof) of the cartridge. As explained above and discussed in more detail below, the current fill level within a module may be updated (e.g., continuously or at a predetermined rate) using data generated by the vision system. In some variations, the current fill level may be compared to the depletion level set for the module (e.g., after each update or at a predetermined periodic time interval).

When the current fill level is determined to be about equal to, or about equal to or less than, the depletion level, a fluid transfer step may be initiated to replenish the module with fresh liquid. For example, in some variations, a vision system may assist in continuous perfusion within a bioreactor module by providing feedback (e.g., to a controller) about a current liquid level therein so that depleted media may be replenished with fresh media.

Moreover, prior to determining the liquid levels, fluid rates, and/or fluid flow paths within cell processing cartridges, the vision systems herein may be calibrated for fluid transfer using a calibration cartridge. For example, a vision system may be used to generate one or more calibration results to be applied to an output (e.g., to each image of a camera stream) of the vision system during cell processing with cell processing cartridges to compensate for one or more of misalignment caused by the vision system, misalignment caused by the cartridge, and distortion caused by the vision system. To compensate for misalignment between the cartridge and vision system that is caused by the vision system, the vision system may be configured to detect a location of one or more fiducial markers, and/or other features (e.g., holes within a label on a flow cell of an MCS module), of the calibration cartridge and use the locations of the fiducial markers (which may define an ROI of the calibration cartridge) to generate a calibration result. For example, the locations of the markers may be mapped onto an ideal reference image to create an alignment map defining an ideal alignment between the vision system and the one or more fiducial markers of the calibration cartridge. The alignment map may be applied to the output of each of one or more sensors of the vision system during cell processing to accurately align the one or more sensors to the calibration cartridge.

Figure 11:
FIG. 11 depicts a perspective view of an exemplary variation of a calibration image for calibrating a vision system of an instrument.

In some variations, generating the alignment map may be sufficient to properly align the vision system and calibration cartridge. Alternatively, in some variations, it may be beneficial to additionally compensate for misalignment between the vision system and cartridge that is caused by one or more modules (or portions thereof) of the cartridge. To compensate for misalignment between the cartridge and vision system that is caused by the cartridge (e.g., by an MCS module of the cartridge, or a flow cell thereof), the vision system may be configured to detect a location of one or more features (e.g., holes within a label on a flow cell of an MCS module) of a module of the calibration cartridge and use the locations of the features (which may define an area that is different than an ROI of the module) to generate a calibration result. For example, the locations of the features may be related to an ideal reference image to create a module map defining an ideal alignment between the vision system and the one or more features of the module. The module map may be applied to the output of each of one or more sensors of the vision system during cell processing to accurately align the one or more sensors to the calibration cartridge. In some variations, the module map may be combined with the alignment map to generate a combined map for applying to the output of the portion of the vision system configured to monitor the given module during cell processing using a cell processing cartridge. In some variations, the module and alignment maps may be generated simultaneously in a single calibration operation. An exemplary calibration image 1100 for generating a module map is depicted in FIG. 11. As shown, the calibration image 1100 may include a checkerboard pattern. Additionally, the calibration image 1100 may have known dimensions, such as a known overall height and width, and/or a known height and width of each of the (equivalent) squares of the image. To rectify the distortion caused by a given camera lens, the camera view may be projected onto the calibration image 1100, and the corner point coordinates of the checkerboard detected by the camera may be used to estimate the distortion map.

Additionally, or alternatively, the vision systems herein may be calibrated for fluid transfer to compensate for distortion caused by the vision system (e.g., by one or more sensors thereof). For example, a camera lens (e.g., wide-angle lens) may distort a raw image output by the camera, which may skew the positional information of a liquid level detected by the camera and therefore potentially introduce error into a real-time liquid level calculation based on images from the camera. To rectify the distorted image from the camera, the vision system (e.g., the camera) may be used to generate a calibration result by detecting coordinates of a calibration image having a known dimension. The calibration result may be a distortion map defining distortion of the calibration image from the coordinates of an output of the vision system, and the output of the vision system during cell processing may be mapped onto the known coordinate system detected from the calibration image to compensate for the distortion. In some variations, the distortion map may be combined with one or both of the module map and the alignment map to generate a combined map for applying to the output of the portion of interest of the vision system (e.g., the one or more sensors configured to monitor a given module during cell processing). In some variations, any combination of the distortion, alignment, and module maps may be generated simultaneously via a single calibration operation, thereby generating a combined map for applying to the output of the portion of interest of the vision system during cell processing.

In general, the vision systems described herein may be operably coupled to one or more controllers of the cell processing system. The vision systems may be configured to transmit (e.g., continuously or at a set or variable rate via one or both of a wired and wireless connection) data, such as image data, to the controller(s) to be analyzed, stored, processed, edited, visualized, transferred, and/or the like. Suitable controllers and aspects thereof for use with the vision systems above (and/or with other systems, devices, and methods herein) are described in more detail below.

Controller

The workcells of the cell processing systems herein may include one or more controllers for directing and monitoring a cell processing procedure. In general, or more components of a workcell, such as each of a plurality of instruments of the workcell, may include or be operably coupled to a controller. As such, the controllers herein may be configured to control one or more cell processing procedures taking place in a cell processing system. For example, the controllers may be configured to simultaneously control a plurality of cell processing procedures being carried out on cell products of a corresponding plurality of cell processing cartridges. In some variations, the controllers herein may be configured to control one or more cell processing operations for a given cartridge by communicating (e.g., using wireless and/or wired transmissions) with one or more instruments that interface with the cartridge throughout a cell processing procedure.

Referring again to FIG. 1A, a controller 120 (e.g., computing device) of the workcell 110 may include one or more of a processor 122, memory 124, communication device, 126, input device 128, and display 130. A processor of the system controller (e.g., processor 122) may process data and/or other signals to control one or more components of the system. The processor may be configured to receive, process, compile, compute, store, access, read, write, and/or transmit data and/or other signals. Additionally, or alternatively, the processor may be configured to control one or more components of a device (e.g., console, touchscreen, personal computer, laptop, tablet, server).

In some variations, the processor may be configured to access or receive data and/or other signals from one or more of workcell 110, server, controller 120, and a storage medium (e.g., memory, flash drive, memory card, database). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

The processor may operate the systems/perform the methods herein using software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including structured text, typescript, C, C++, C#, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

A memory (e.g., memory 124) of the controller may be configured to store data and/or information. In some variations, the memory may include one or more of a random-access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with the device, such as image processing, image display, sensor data, data and/or signal transmission, data and/or signal reception, and/or communication. Some embodiments described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The computer code (also may be referred to as code or algorithm) may be those designed and constructed for the specific purpose or purposes. In some variations, the memory may be configured to store any received data and/or data generated by the controller and/or workcell. In some variations, the memory may be configured to store data temporarily or permanently.

An input device (e.g., input device 128) of the controller may comprise or be coupled to a display (e.g., display 130). Input device may be any suitable device that is capable of receiving input from an operator via, for example, a keyboard, buttons, touch screen, and/or the like. The input device may include at least one switch configured to generate a user input. For example, an input device may include a touch surface for a user to provide input (e.g., finger contact to the touch surface) corresponding to a user input. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In embodiments of an input device including at least one switch, a switch may have, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a user input. A microphone may receive audio data and recognize a user voice as a user input.

Graphical and/or image data may be output on a display (e.g., display 130) of the controller. In some variations, a display may include at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display. In some variations, a GUI may be configured for designing a process and monitoring a product and may be shown on the display.

Further, in some variations, the controller may include a communication device (e.g., communication device 126) configured to communicate with another controller and one or more databases. The communication device may be configured to connect the controller to another system (e.g., Internet, remote server, database, workcell) by wired or wireless connection. In some variations, the system may be in communication with other devices via one or more wired and/or wireless networks. In some variations, the communication device may include a radiofrequency receiver, transmitter, and/or optical (e.g., infrared) receiver and transmitter configured to communicate with one or more devices and/or networks. The communication device may communicate by wires and/or wirelessly.

As described herein throughout, the controllers herein may be configured to use data, such as image data, detected by the vision systems herein to determine real-time liquid levels and/or fluid transfer parameters (e.g., flow rates) within cell processing cartridges and/or to control fluid transfer within the cartridges.

Figure 12:
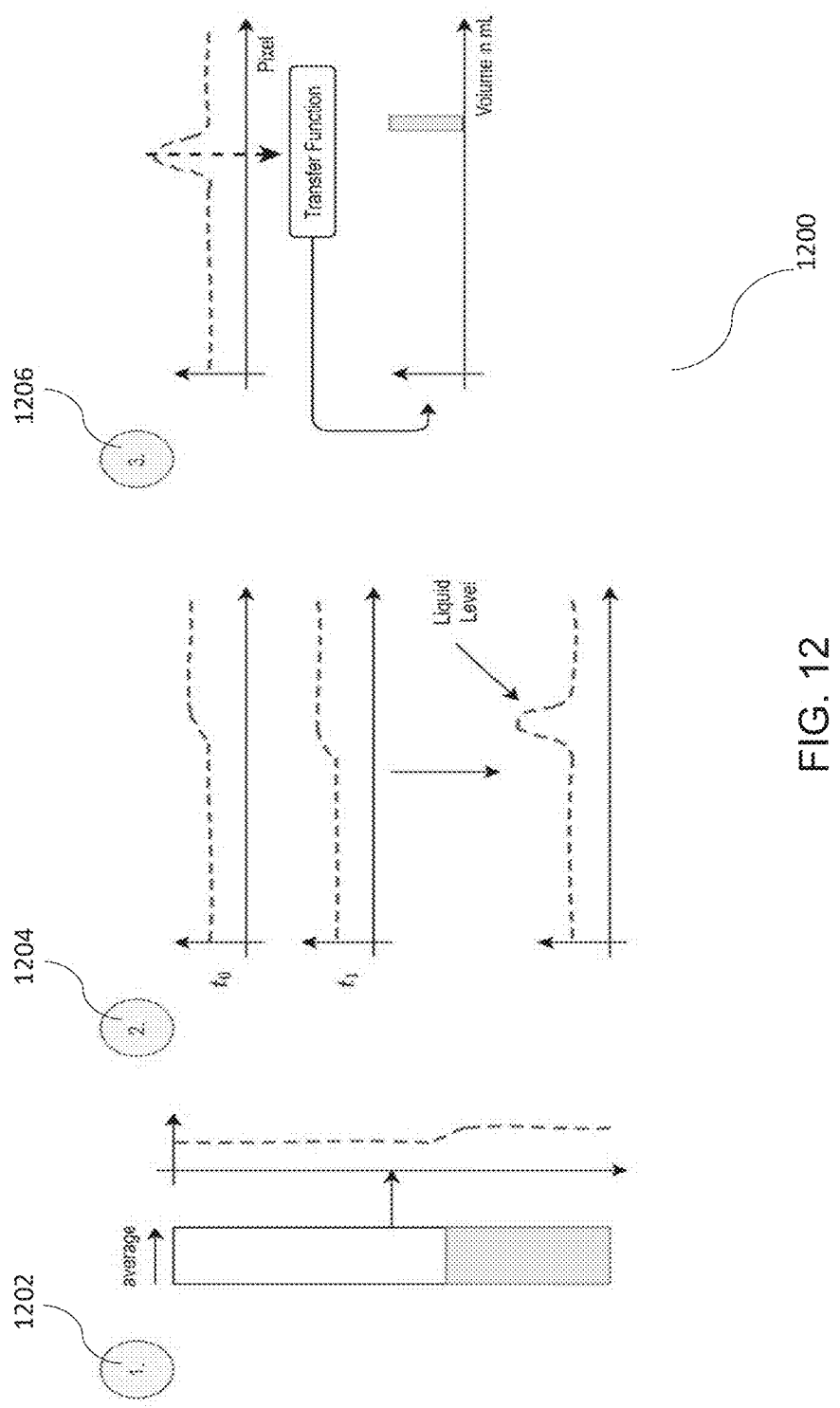
FIG. 12 is a representation of an illustrative variation of a method for determining a liquid level of a fluid compartment using image data of the liquid within the fluid compartment.

For example, in a first aspect, a controller (e.g., controller 120 of FIG. 1A) may be configured to process and analyze image data of a cartridge region-of-interest (ROI) detected by a vision system (e.g., vision system 170 of FIG. 1A) to determine a real-time liquid level of liquid within the ROI. In some variations, the image data may include a real-time image and/or a series of images of the ROI. FIG. 12 depicts an illustrative variation of a method 1200, which may be employed by the controllers herein, for determining a liquid level of a fluid compartment using image data of the liquid within the fluid compartment. To determine the liquid level using the image data, a controller may first process the data, such as by averaging the data over a time period and/or reducing the data into a 1D or 2D signal. This process is shown as step 1202 of FIG. 12. In some variations, the image data may be reduced to a numerical array or image gradient, which may represent a rate of change of a liquid level of liquid within the ROI during the time period. Additionally, as in step 1204 of the method 1200, the controller may analyze the processed data (e.g., the gradients thereof) to identify a pixel position of a peak intensity gradient of the data, which may define a real-time position of the liquid level (e.g., relative to the ROI and/or fluid compartment containing the liquid). That is, the liquid level may be located as a function of pixel position of the image(s) provided to the controller by the vision system. Further, as in step 1206 of the method 1200, the controller may be configured to convert (e.g., using a transfer function) the pixel position of the peak intensity gradient to the real-time liquid level (i.e., real-time liquid volume) of the liquid within the ROI. In some variations, the controller may additionally be configured to analyze (e.g., periodically) a signal to noise ratio between the background signal and the detected signal of the image provided by the vision system to verify that the detected signal represents the liquid level of the liquid over time.

Figure 13A:
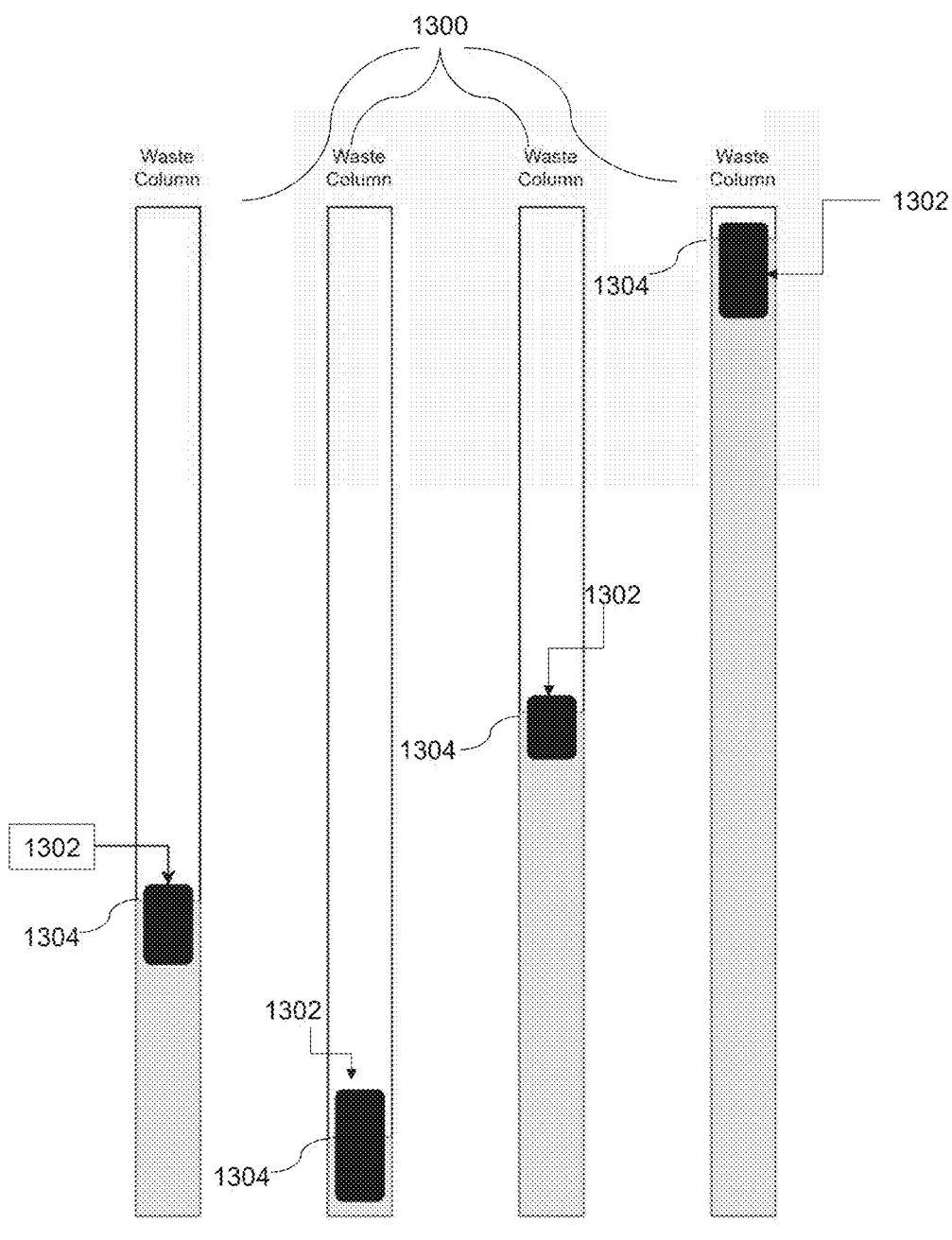
FIG. 13A is a depiction of front views of an illustrative variation of a waste column of a waste module.
Figure 13B:
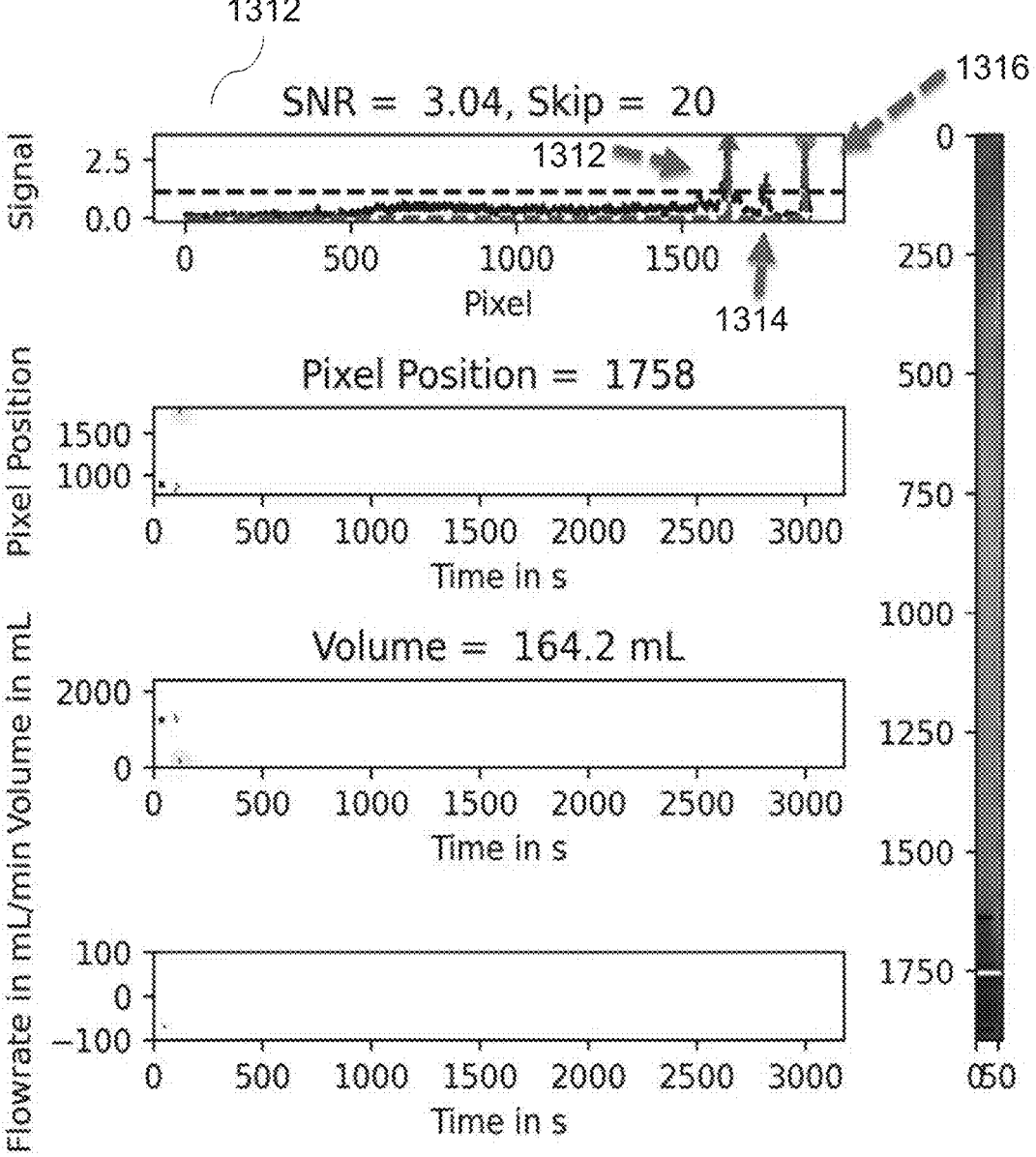
FIG. 13B is a graph showing how a liquid level of the waste column of FIG. 13A was determined using a floating member within the waste column.

Additionally, or alternatively, in a second aspect, the controllers herein may be configured to determine a liquid level of liquid within an ROI of a cartridge by analyzing a size and/or outline of a floating member (e.g., a 3D floating member) configured to float at a liquid surface of the liquid within the ROI. For example, in some variations, a liquid surface within a module or fluid compartment of the cartridge (e.g., within a waste column of a waste module) may be obscured (e.g., by bubbles). Without clear image data of the liquid surface, it may be difficult for the controller to accurately determine the liquid level within the ROI. Thus, the controller may calculate the size and/or outline of a floating member therein, which may change (in 2D) along a vertical axis of the ROI due to refraction, to determine the liquid level of the obscured liquid surface. That is, in such variations, the controller may not determine the maximum intensity value of the vision system image data to calculate the real-time liquid level. Instead, because the floating member, depending on its level within the ROI, may have a perceived changing size and/or outline (e.g., relative to the waste column and/or ROI defined for the waste column), the controller may calculate the size of the floating member and/or a ratio of its outline extending above versus below the liquid surface to determine the liquid level. For example, referring briefly to FIG. 13A, an outline of the floating member 1302 within the waste column 1300 appears larger if it is at the bottom or top of the column 1300, and looks the smallest when it is floating at the center of the column 1300. Additionally, a fraction of the outline of the floating member 1302 that extends above the liquid surface 1304 is greater when the floating member 1302, and thus the liquid surface 1304, is near the bottom of the waste column 1300 versus the top. Oppositely, a fraction of the outline of the floating member 1302 that extends below the liquid surface 1304 is greater when the floating member 1302, and thus the liquid surface 1304, is near the top of the waste column 1300 versus the bottom. When the floating member 1302 travels from the bottom toward the middle of the waste column 1300 (e.g., when the waste column 1300 is being filled), a fraction or percentage of the total outline of the floating member 1302 that extends above the liquid surface 1304 may decrease and may remain a similar fraction or percentage thereon from the middle to the top of the waste column, while a fraction or percentage of the total outline of the floating member 1302 that extends below the liquid surface 1304 may decrease slightly, and then may increase from thereon from the middle to the top of the waste column. Thus, a large or maximum signal peak, and the prior trend of the signal amplitude, may be analyzed to determine that a floating member, and thus liquid surface, within a fluid compartment is at a particular position adjacent either the top or the bottom of the fluid compartment. Conversely, an average peak, and the prior trend of the signal amplitude, may be analyzed to determine that the floating member, and thus liquid surface, is at a particular position adjacent the middle of the container. The controller may accordingly be configured convert the signal amplitude to pixel position, and then map (e.g., using a transfer function) the pixel position to the real-time liquid volume of liquid within the ROI. For example, turning to FIG. 13B, a plot 1310 shows an exemplary signal representing a change in the liquid level (and thus change in the size and outline of the floating member 1302 therein) shown over the four interactions of the waste column 1300 of FIG. 13A is shown. A first signal peak 1312 corresponds to the second column 1300 (from the left), where the floating member 1302 is proximal to the bottom of the second waste column 1300. A second signal peak 1314 corresponds to the third column 1300 (from the left), where the floating member 1302 is proximal to the center of the third waste column 1300. Finally, a third signal peak 1416 corresponds to the fourth column 1300 (from the left), where the floating member 1302 is proximal to the top of the fourth waste column 1300.

Moreover, in another aspect, the controllers herein may be configured to use image data from the vision systems herein to verify fluid transfer parameters within a cartridge (e.g., a cartridge 114), such as fluid flow rates using a stream of image data provided by a vision system. For example, a controller may receive, from a vision system, a series of images of an ROI of one or both of a fluid transfer origin and destination module during a fluid transfer step. The controller may be configured to determine and record liquid level measurements (e.g., volumes) of the origin and/or destination modules throughout the duration of the fluid transfer (or a portion thereof) using the image data, as explained above with respect to FIG. 12 and FIGS. 13A-13B. In some variations, the controller may be configured to generate a liquid level trend for one or both of the origin and destination modules. For example, each liquid level trend may include liquid level calculations made using data collected from time $X_0$ (e.g., the beginning of the fluid transfer) to time $X_1$ (e.g., between the beginning of the fluid transfer and up to and including the end of the fluid transfer). Further, the controller may determine a real-time flow rate of the fluid transfer using the recorded liquid level measurements, such as via time derivative. Additionally, or alternatively, the controller may determine a flow rate (e.g., a real-time flow rate) of the fluid transfer by monitoring and/or controlling an operational speed of a pump (e.g., pump 138 of FIG. 1A) engaged with the given cartridge. Accordingly, in some variations, the controller may determine the flow rate of the fluid transfer using data from the vision system and compare this real-time flow rate to a desired flow rate defined by the operational speed of the pump in order to verify that the operational parameters of the fluid transfer step are accurate.

Figure 14:
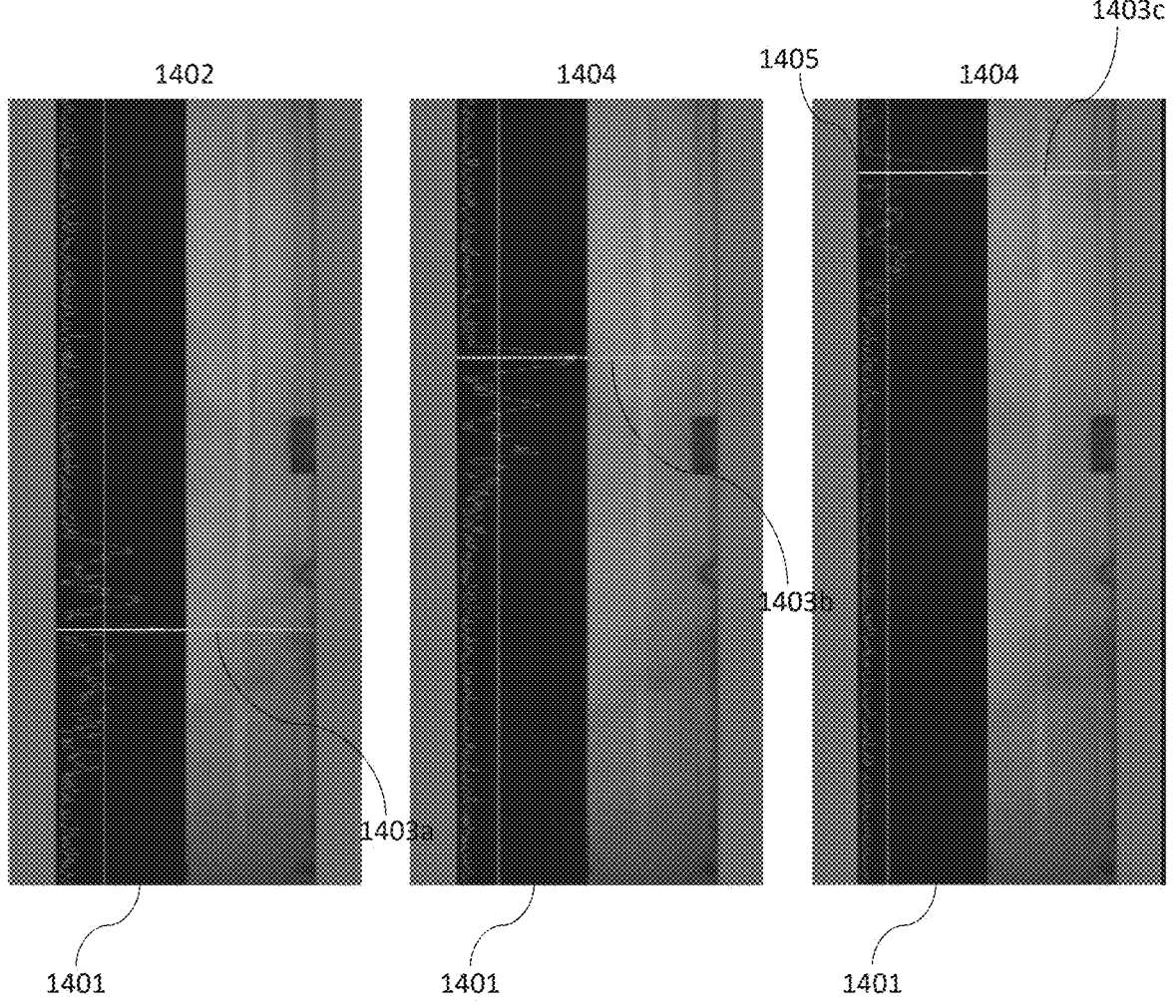
FIG. 14 depicts perspective views of an exemplary flow cell of a magnetic cell sorter module during fluid transfer into the flow cell.

Further, in yet another aspect, the controllers herein may be configured to use data from a vision system to control filling of one or more modules or fluid compartments of a cartridge interfacing with the vision system. For example, a controller may use image data (e.g., a real-time image or series thereof) of a liquid level of an ROI of the cartridge may to determine when a liquid level condition of the fluid compartment is met, such as when a desired fill level of the fluid compartment is achieved. In some variations, the controller may be configured to determine a current fill level (i.e., real-time liquid level) of the ROI using the latest image data received from the vision system (as explained above with respect to FIG. 12 and FIGS. 13A-13B). The controller may be configured to compare the current fill level to the desired fill level, and may be further configured to stop the fluid transfer when the current fill level is about equal to, or about equal to or greater than, the desired fill level. For example, the controller may be configured to stop or reduce an operational speed of a pump (e.g., pump 138 of FIG. 1A) driving the fluid transfer. An example of such a process is shown with respect to a flow cell 1401 of an MCS module in FIG. 14. The images 1402, 1404, 1406 each show the flow cell 1401 during a filling step such as the one described above. That is, the flow cell may be continuously filled while a controller (not shown) is calculating its current fill level using image data of the ROI including the flow cell from a vision system (not shown). As shown, the current fill levels 1403*a,b* of the images 1402, 1404 calculated by the controller are both less than the desired fill level 1405. However, in image 1404, the current fill level 1403*c* calculated by the controller is about equal to the desired fill level 1405. Thus, the controller may trigger the pump to stop operating upon comparing the current fill level 1403*c* to the desired fill level 1405.

In another example, a liquid level condition may include a depletion level for one or more modules (e.g., one or more fluid compartments thereof) of the cartridge. The controller may be configured to calculate and compare a current fill level for a given ROI (e.g., for an ROI of a bioreactor module) to the depletion level using data generated by the vision system, as explained above. When the controller determines that the current fill level is about equal to, or about equal to or less than, the depletion level, the controller may be configured to initiate a fluid transfer step may to replenish the module with fresh liquid. For example, the controller may trigger movement (e.g., rotation) of a rotor of a pump (e.g., pump 138 of FIG. 1A) engaged with the cartridge containing the ROI to cause fluid to fill the module (e.g., one or more fluid compartments thereof, such as a bioreactor, a mixing chamber, and/or one or more thermal compartments of a bioreactor module). Accordingly, in some variations, the controllers herein may be configured to manage one or more back-to-back fluid transfer steps, such as a back-to-back combination of depletion and filling steps for a given module.

Moreover, the controllers herein may additionally or alternatively be configured to determine one or more ROIs of a cartridge during a calibration procedure, such as by generating a calibration result (e.g., one or more calibration results) based on a location of each of one or more fiducial markers of a cell processing cartridge detected by a vision system. The controllers may also be configured to apply the calibration result to an output (e.g., a real-time image) of the vision system during cell processing using a cell processing cartridge.

Additional workcells, instruments, controllers, and aspects thereof, suitable for use with the systems, devices, and methods herein are provided in, e.g., U.S. Pat. No. 11,872,557, issued Jan. 16, 2024, U.S. Prov. Pat. App. 63/470,381, filed Jun. 1, 2023, and U.S. Prov. Pat. App. 63/524,596, filed Jun. 30, 2023, and U.S. Prov. Pat. App. 63/612,987, filed Dec. 20, 2023, each of which was previously incorporated by reference herein.

II. Methods for Cell Processing

Also described herein are methods for cell processing, including methods for calibrating fluid transfer within a cell processing system and methods for monitoring liquid levels and/or fluid transfer (e.g., within one or more cartridges) during cell processing. While the following methods may be described with respect to a single cartridge and instrument, it should be understood that the methods herein may be used with a plurality of cartridges and/or instruments (and/or workcells) of a cell processing system. Additionally, the methods herein may be used individually and/or in combination in any suitable order. For example, in some variations, methods for monitoring liquid levels and/or fluid transfer within a cell processing cartridge may occur after, or separately from, a calibration procedure (e.g., after method 1500 of FIG. 15) using a calibration cartridge. However, in some variations, the methods for monitoring liquid levels and/or fluid transfer parameters within a cell processing cartridge may occur prior to a calibration procedure, or prior to and following a calibration procedure (e.g., when the calibration procedure is periodically repeated for maintenance of a cell processing system, as described above). Moreover, the methods for monitoring liquid levels within a cartridge may occur before, during, and/or after the methods for monitoring fluid transfer within a cartridge, and vice versa. For example, a method for monitoring fluid transfer of a cartridge may include all the steps of a method for monitoring liquid levels of the cartridge. In some variations, one or more methods for monitoring a liquid level within a cartridge may be carried out (e.g., by a vision system and controller, such as vision system(s) 170 and controller 120 of FIG. 1A) simultaneously or may partially overlap. For example, a procedure for monitoring a liquid level and/or a fluid transfer within a cartridge may be performed at least partially simultaneously for each of a plurality of cartridges being processed in parallel within a workcell. Likewise, a procedure for monitoring a liquid level and/or a fluid transfer within a cartridge may additionally or alternatively be performed at least partially simultaneously for each of a plurality of modules of the cartridge. Similarly, a procedure for monitoring a liquid level and/or a fluid transfer within a cartridge may additionally or alternatively be performed at least partially simultaneously for each of a plurality of portions (e.g., fluid compartments) of one or more modules of the cartridge Generally, the methods herein may include a step for coupling a cartridge (e.g., a calibration cartridge and/or a cell processing cartridge) to a cell processing instrument. This coupling step may be a first step for performing a majority (e.g., all) of cell processing operations using the systems and devices herein. The coupling formed during this step may be releasable or temporary. The instrument may include a vision system. For example, the vision system may be positioned on an enclosure of the instrument. In some variations, one or more sensors of the vision system may be supported by the enclosure of the instrument. Each of the one or more sensors may be oriented or directed toward a cartridge module (e.g., toward an ROI of the module) and/or toward an optical path originating at the module when the cartridge is interfacing with (e.g., within a docking station of) the instrument. Further, the instrument may be a bioprocessing instrument (e.g., a bioreactor instrument, an MCS instrument, a FACS instrument, an EP instrument, a CCE, instrument, etc.) or a liquid transfer instrument (e.g., a sterile liquid transfer instrument). In some variations, some or all of the methods herein may be performed when a cartridge is interfacing with any one of the workcell instruments herein.

As described below, the methods herein may include one or more detecting steps for calibration or for monitoring part of a cell processing procedure (e.g., for verifying liquid levels and/or transfers within a cartridge). In general, the detecting may occur via a vision system (e.g., a vision system 170 of FIG. 1A) of an instrument (e.g., instrument 112 of FIG. 1A) such as via one or more of a plurality of sensors (e.g., cameras) of the vision system. The detecting may be continuous or may utilize discrete measurements taken at a constant or varied rate. In some variations, the rate of the detecting may be adjustable (e.g., by an operator and/or controller of the cell processing system). As an example, each of one or more modules of a cartridge (e.g., a cell processing and/or calibration cartridge) may have an associated sensor (e.g., a camera) configured to monitor at least a portion of the module, such as at least one fluid compartment of the module. In some variations, as discussed with respect to FIGS. 10A-10B, the vision system may additionally include one or more light sources, mirrors, prisms, polarizers, and/or combinations thereof for providing light for the sensors to detect and reflecting, angling, and/or filtering the light for optimal detection. Accordingly, all of the one or more sensors need not directly face the portion(s) of the module being monitored. In some variations, a subset (e.g., all or less than all) of a plurality of sensors of the vision system may be directly oriented toward the portion(s) of the module being monitored.

Calibrating Fluid Transfer within Cell Processing Systems

In general, a method for calibrating fluid transfer within a cell processing system (e.g., system 100 of FIG. 1A) may occur during initial setup of the system and/or periodically thereafter (e.g., for maintenance). For example, the method may be carried out during initial setup of the system and/or repeated at intervals of about 1 day to about 5 years, such as about 1 week to about 2.5 years, about 2 weeks to about 2 years, about 1 month to about 20 months, about 2 months to about 18 months, about 3 months to about 16 months, about 4 months to about 14 months, about 6 months to about 12 months, or about 7 months to about 10 months (including all ranges and subranges therein). The method may include coupling (e.g., releasably coupling) a cartridge (e.g., a calibration cartridge, such as a cartridge 114 of FIG. 1B) to an instrument (e.g., an instrument 112 of FIG. 1A) of the system. The cartridge may have one or more fiducial markers ("markers") and/or other features (e.g., holes). In some variations, the locations of the markers and/or other features on the cartridge may define one or more ROIs for monitoring liquid levels and/or fluid transfer parameters during cell processing. The instrument may include a vision system for detecting a location of each of the one or more markers and/or other features. Next, the method may include generating a calibration result (e.g., via a controller operably coupled to the vision system) using the locations of each of the one or more markers and/or other features. The calibration result may be an alignment map defining alignment between the vision system and the one or more fiducial markers and/or other features of the calibration cartridge. The calibration result may be applied to an output (e.g., an image or a series of images) of the vision system during cell processing with a cell processing cartridge to compensate for misalignment between the vision system (e.g., one or more sensors thereof) and the fiducial markers and/or other features of the cartridge. In some variations, the method may include generating a plurality of calibration results using the calibration cartridge and one or more calibration images (e.g., images having a known dimension). In some variations, the calibration result may be a first calibration result, and the method may include generating a second calibration result by using coordinates of a calibration image detected by the vision system. The second calibration result may be a distortion map defining distortion of the calibration image from the coordinates of an output (e.g., a real-time image) of the vision system. In some variations, this distortion may be due to one or more lenses of sensors of the vision system. The distortion map may be applied to the output of each of the one or more sensors during cell processing to compensate for the distortion. In some variations, the first and second calibration results may be generated and/or applied simultaneously during calibration and cell processing, respectively. In some variations, the method may include combining the first and second calibration results into a combined calibration results and applying the combined calibration result to the vision system output during cell processing.

Figure 15:
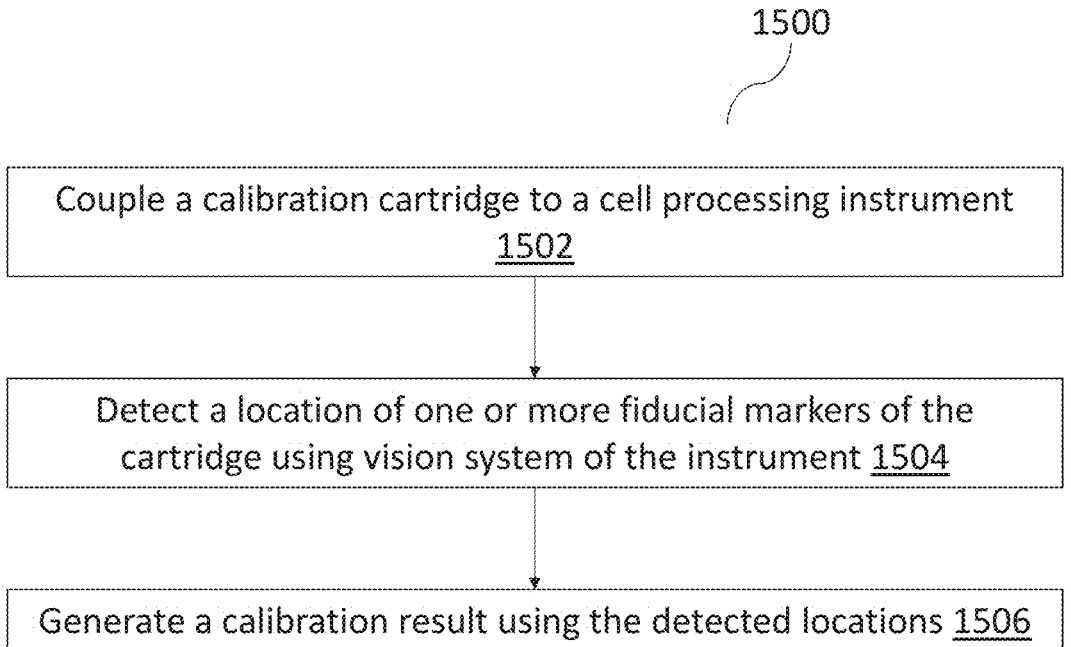
FIG. 15 is a flow diagram of an illustrative method for calibrating fluid transfer within a cell processing system.

A flow chart illustrating an exemplary method 1500 for calibrating a cell processing system is shown in FIG. 15. First, the method 1500 may include coupling 1502 a calibration cartridge to a cell processing instrument. The calibration cartridge may include one or more fiducial markers, such as a plurality thereof, and may be shaped and sized to be fit within a cell processing instrument (e.g., may include the same modules in the same configuration).

Second, the method 1500 may include detecting 1504 a location of one or more of the fiducial markers of the calibration cartridge using the vision system of the instrument. For example, a first set of fiducial markers may define a first ROI of the calibration cartridge, and a second set of fiducial markers may define a second, different ROI of the calibration cartridge. The first ROI may include a portion of a first module of the cartridge, such as a side of a fluid compartment of the first module of the cartridge. In some variations, a second ROI may include a different portion of the first module, such as a different side of the same fluid compartment or a side of a different fluid compartment of the first module. In some variations, the second ROI may include a portion of a second, different module of the cartridge, such as a side of a fluid compartment of the second module of the cartridge. In some variations, the second ROI may include a different portion of the first module, and the detecting may further include detecting a third set of fiducial markers defining a third, different ROI of the calibration cartridge, such as a third ROI including a portion of the second, different module of the cartridge. Similarly, it should be understood that the detecting 1504 may include detecting 1504 some or all of the subsets of fiducial markers of the calibration cartridge defining the ROIs for liquid level and/or fluid transfer monitoring during cell processing with a cell processing cartridge.

Next, the method 1500 may include generating 1506 a calibration result using the detected locations of the fiducial markers. In some variations, the generating 1506 may include transmitting an output (e.g., one or more images, such as a real-time image) of the vision system to a controller, and the controller may generate the calibration result. In some variations, the generating 1506 may include identifying or determining the ROI defined by the locations of each of the one or more fiducial markers and mapping the ROI onto a reference image. The calibration result may be a map (e.g., an alignment map) defining alignment between the vision system and the one or more fiducial markers, such as defining a misalignment between the vision system and the one or more fiducial markers caused by the vision system. The method 1500 may then include applying the map to an output (e.g., one or more images) of the vision system (e.g., one or more sensors thereof) during cell processing to accurately align the one or more sensors to a cell processing cartridge. Like the detecting 1504, it should be understood that the generating 1506 may include generating 1506 a calibration result associated with some or all of the detected fiducial markers of the calibration cartridge (and, correspondingly, for some or all of the sets of sensors used to detect the sets of fiducial markers) defining the ROIs for liquid level and/or fluid transfer monitoring during cell processing with a cell processing cartridge. For example, a calibration result may be generated for one or more of a bioreactor module, an (MCS) module, a CCE module, and a waste module of the calibration cartridge. In some variations, a calibration result may be generated for one or more fluid compartments of each of the one or more modules.

Moreover, in some variations, the generating 1506 may further include generating a calibration result for compensating for misalignment caused by the calibration cartridge. For example, the calibration result may define alignment between an actual position of the calibration cartridge and a desired position of the calibration cartridge based on one or more detected features of a module or fluid compartment thereof of the calibration cartridge (e.g., a bioreactor, MSC, CCE, and/or waste module) that. The calibration result, which may be a module map, may be mapped onto an output (e.g., one or more images, such as a real-time image) of a portion of the vision system focused on the particular module during cell processing to align the portion of the vision system to the module. Like the fiducial markers, the one or more detected features may be a plurality of physical features on an exterior of or adjacent to a module. For example, a flow cell of the MCS module may include a label attached thereto, the label having a plurality of holes that are the features detected by the portion of the vision system during the calibration.

Furthermore, in some variations, the generating 1506 may further include generating a calibration result for compensating for distortion (e.g., of the output of the vision system) caused by the vision system, such as distortion caused by a lens of one or more sensors of the vision system. In such variations, the distortion may be compensated for by generating a calibration result using the detected coordinates of a calibration image having a known dimension. During cell processing, an output of the vision system (e.g., of the one or more sensors causing the distortion) may be mapped to the coordinates of the known image mapping an output of the vision system to the coordinates of the calibration image to compensate for the distortion.

In some variations, the method may include combining two or more of the calibration results discussed above (e.g., the alignment map, the module map, and/or the distortion map) into a single, combined calibration result. Then, the method may include applying the combined calibration result to an output (e.g., to one or more images) of the vision system during a cell processing procedure.

Monitoring Liquid Levels within Cell Processing Cartridges

Another method for use with the systems, devices, and methods herein may include monitoring a liquid level (i.e., volume) of a liquid within a cell processing cartridge (e.g., cartridge 114 of FIG. 1B) during a cell processing procedure. In some variations, the method may include monitoring one or more liquid levels, such as a plurality thereof, within a cell processing cartridge simultaneously. Each liquid level monitored may be associated with (e.g., visible within at least a portion of) at least one region of interest (ROI) detected by a vision system interfacing with the cartridge.

An exemplary variation of such a method is illustrated in FIG. 16. As shown, the method 1600 may first include coupling 1602 (e.g., releasably coupling) a cell processing cartridge to an instrument (e.g., an instrument 112 of FIG. 1A) that is configured to perform a cell processing operation with at least one module of the cartridge. Next, the method may include detecting 1604 a liquid level of a liquid within one or more modules (e.g., within one or more ROIs and/or fluid compartments thereof) of the cartridge. The detecting 1604 may occur via a vision system of the instrument, such as via one or more of a plurality of sensors of the vision system. For example, each of a plurality of ROIs of the cartridge may have an associated sensor (e.g., a camera) of the vision system that is configured to monitor a liquid level within the ROI. In some variations, the detecting 1604 may include transferring, such as automatically transferring, some or all of the liquid level data from the vision system to a controller of the system.

Next, method may include determining 1606 a volume of the liquid within each of the one or more modules based on the liquid level. In some variations, the determining 1606 may occur via a controller of the system. In some variations, the determining 1606 may include processing and/or analyze data detected by the vision system to determine a real-time liquid level (i.e., volume) of liquid within the one or more modules. In some variations, the determining 1606 may include one or more steps of the method 1200 of FIG. 12 described herein above. For example, the determining 1606 may include transforming a real-time image of an ROI (e.g., of a module and/or one or more fluid compartments associated with the ROI) to a numerical array representing one or more intensity gradients of the real-time image. Next, the determining 1606 may include identifying a peak intensity gradient of the numerical array, and finally determining a location of the liquid level (e.g., with respect to a reference point of an ROI or fluid compartment holding the liquid) based on a position of the peak intensity gradient.

In some variations, the determining 1606 may additionally or alternatively include analyzing a size and/or outline of a 3D object, such as a floating member, that is configured to float at a liquid surface of the liquid of interest (e.g., within an ROI associated with the liquid level being detected). For example, the determining 1606 may include analyzing a size and/or outline of a floating member within a waste module, such as within a waste column of the waste module. Because the floating member, depending on its position within an ROI of the waste module, may have a perceived variable size and/or outline (e.g., due to refraction and relative to the waste column and/or ROI defined for the waste column), the determining 1606 may include calculating the size of the floating member and/or a ratio of its outline extending above versus below the liquid surface to determine the liquid level. When the determining includes analyzing a size and/or outline of a floating member, one or more sub steps of the determining 1606 may be: identifying a location of the surface of the liquid (e.g., based on one or both of an outline and a size of the floating member), transforming a real-time image of a fluid compartment (e.g., a waste column) of the waste module to a numerical array representing one or more intensity gradients of the real-time image, identifying a peak intensity gradient of the numerical array, and determining a location of the liquid level (e.g., within an ROI or fluid compartment of the cartridge) based on the location of the surface of the liquid and a position of the peak intensity gradient. A variation of such a method is described in detail above with reference to FIGS. 13A-13B. Furthermore, in some variations, the determining 1606 may include converting the location of the liquid level to a volume of the liquid based on known geometry of the module and/or fluid compartment containing the liquid.

Moreover, the method 1600 may optionally include one or more steps for notifying an operator of a calculation, estimation, and/or observation made (e.g., via the controller 120) that is related to the liquid level(s) and/or liquid transfer(s) within the cartridges. In some variations, notifying the operator may include displaying (e.g., visually via a display such as display 130, or a user interface thereof) an alert, such as a low liquid level or high-liquid level alert for a module. The low liquid level alert may be generated when a liquid level or volume is determined to be below a threshold for the liquid level or volume (e.g., within a given fluid compartment). Oppositely, a high liquid level alert may be generated when a liquid level or volume is determined to be above a threshold for the liquid level or volume (e.g., within a given fluid compartment). In some variations, notifying the operator may include prompting the operator to adjust parameters of the fluid transfer (e.g., the flow rate and/or flow path and/or desired liquid volume for transfer) within the cartridge. For example, the operator may reduce or stop the fluid transfer (e.g., reduce an operational speed of or turn off a pump of interfacing with the cartridge to stop the liquid flow), and/or may remove the cartridge from the instrument.

Monitoring Fluid Transfer within Cell Processing Cartridges

Another method for use with the systems, devices, and methods herein may include monitoring a fluid transfer, such as monitoring one or more parameters thereof, within a cell processing cartridge (e.g., cartridge 114 of FIG. 1B). In some variations, the method may include some or all of the steps of the method for monitoring liquid levels within a cell processing cartridge, as described above. For example, each of one or more liquid levels monitored may be associated with (e.g., visible within at least a portion of) at least one region of interest (ROI) detected by a vision system of an instrument interfacing with the cartridge. In some variations, monitoring the fluid transfer may include verifying one or more planned parameters of a fluid transfer step. For example, the method may include verifying one or both of a flow rate and/or flow path of fluid transfer within a cartridge.

An exemplary variation of such a method is illustrated in FIG. 17. As shown, the method 1700 may first include coupling 1702 (e.g., releasably coupling) a cell processing cartridge to an instrument (e.g., an instrument 112 of FIG. 1A) that is configured to perform a cell processing operation with at least one module of the cartridge. Next, the method may include verifying 1704 one or more parameters of fluid transfer within the cartridge via a vision system of the instrument. In some variations, the verifying 1704 may include detecting, via the vision system, motion of a pump configured to interface with the cartridge (and control the fluid transfer therein) to verify the flow rate of a fluid transfer step (because an operational speed of the pump may correspond to the flow rate of fluid transfer). For example, one or more sensors thereof of the vision system may be configured to detect a rotor of the pump and generate an output (e.g., image data) of the rotor that may be used (e.g., by a controller) to calculate a real-time operational speed of the pump. Additionally, or alternatively, the verifying 1704 may include identifying and/or monitoring (e.g., via the vision system) an origin and/or destination module of the fluid transfer to verify a fluid path thereof. Next, the method 1700 may include detecting 1706 a liquid level within one or more modules of the cartridge. In some variations, the detecting 1706 may including detecting a liquid level within one or both of the origin and destination modules to verify that fluid is transferring out of the origin module (e.g., via a decreasing liquid volume) and/or into the destination module (e.g., via an increasing liquid volume). For example, the detecting 1706 may further include analyzing (e.g., via a controller) an output of the vision system to determine whether the liquid volumes of the origin and/or destination modules are transferring accurately (e.g., are increasing or decreasing as planned). In some variations, the detecting 1706 may occur throughout some or all of a duration of the fluid transfer. Further, the method 1700 may include determining 1708 a fluid flow rate using the detected liquid levels each of the one or more modules (e.g., within one or both of the origin and destination modules for the fluid transfer) over the duration of the fluid transfer (or at least a portion thereof). In some variations, the determining 1708 may include generating a liquid level trend for one or both of the origin and destination modules. For example, each liquid level trend may include liquid level calculations made using data collected from time $X_0$ (e.g., the beginning of the fluid transfer) to time $X_1$ (e.g., between the beginning of the fluid transfer and up to and including the end of the fluid transfer). Then, a real-time flow rate of the fluid transfer may be determined using the recorded liquid level measurements, such as via time derivative. Additionally, or alternatively, the method 1700 may include determining a second flow rate (e.g., a real-time flow rate) of the fluid transfer by monitoring and/or controlling (e.g., via a controller) an operational speed of a pump engaged with the given cartridge. Thus, the flow rate of the fluid transfer calculated during the determining step 1708 may, in a separate step of the method 1700, be compared to a second, desired flow rate defined by the operational speed of the pump in order to verify that the operational parameters of the fluid transfer step are accurate.

In some variations, the method 1700 may further include controlling (e.g., modifying) a fluid transfer step within the cartridge. For example, during the detecting step 1706, the method may optionally include comparing a current fill level of one or more of the modules involved in the transfer to a liquid level condition of the module. The liquid level condition may include one or both of, for example, a desired fill level (e.g., a high-liquid threshold) and a depletion level (e.g., a low liquid threshold). When a current fill level being detected is determined to be about equal to or greater than the desired fill level, or about equal to or less than the depletion level, the method may include modifying the fluid transfer step to prevent liquid overflow from the given module or to replenish fluids needed to carry out a cell processing operation with the given module. An example of such a process is shown with respect to a flow cell 1401 of an MCS module in FIG. 14. The images 1402, 1404, 1406 each show the flow cell 1401 during a filling step such as the one described above. That is, the flow cell may be continuously filled while a controller (not shown) is calculating its current fill level using image data of the ROI including the flow cell from a vision system (not shown). As shown, the current fill levels 1403*a,b* of the images 1402, 1404 calculated by the controller are both less than the desired fill level 1405. However, in image 1404, the current fill level 1403*c* calculated by the controller is about equal to the desired fill level 1405. Thus, the controller may trigger the pump to stop operating upon comparing the current fill level 1403*c* to the desired fill level 1405. For example, the controller may be configured to stop or reduce an operational speed of a pump driving the fluid transfer in order to stop the fluid transfer.

Referring again to the method 1700 of FIG. 17, for a module (e.g., a bioreactor module) having a current fill level that is determined to be about equal to, or about equal to or less than, the depletion level, the method 1700 may include initiating a fluid transfer step may to replenish the module with fresh liquid. For example, in some variations, a vision system may assist in continuous perfusion within a bioreactor module by providing feedback (e.g., to a controller) about a current liquid level therein so that depleted media may be replenished with fresh media.

Moreover, like the method 1600, the method 1700 may optionally include one or more steps for notifying an operator of a calculation, estimation, and/or observation made (e.g., via the controller 120) that is related to the liquid level(s) and/or liquid transfer(s) within the cartridges. In some variations, notifying the operator may include displaying (e.g., visually via a display such as display 130, or a user interface thereof) an alert, such as a low liquid level or high-liquid level alert for a module. The low liquid level alert may be generated when a liquid level or volume is determined to be below a threshold for the liquid level or volume (e.g., within a given fluid compartment). Oppositely, a high liquid level alert may be generated when a liquid level or volume is determined to be above a threshold for the liquid level or volume (e.g., within a given fluid compartment). In some variations, notifying the operator may include prompting the operator to adjust parameters of the fluid transfer (e.g., the flow rate and/or flow path and/or desired liquid volume for transfer) within the cartridge. For example, the operator may reduce or stop the fluid transfer (e.g., reduce an operational speed of or turn off a pump of interfacing with the cartridge to stop the liquid flow), and/or may remove the cartridge from the instrument.

Throughout this application, the term "about" is used to indicate that a value includes the inherent variation of error for the device, or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

The above-described systems and methods can be implemented in any of numerous ways. For example, at least some methods described herein may be implemented using hardware, firmware, software, or a combination thereof. When implemented in firmware and/or software, the firmware and/or software code can be executed on any suitable processor or collection of logic components, whether provided in a single device or distributed among multiple devices.

In this respect, various aspects described herein may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods disclosed herein need not reside on a single computer or processor but may be distributed in a modular fashion amongst a number of different computers or processors to implement various aspects of the inventions disclosed herein.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in different variations.

Additionally, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Further, the acts performed as part of the methods herein may be ordered in any suitable way. Accordingly, various methods may be constructed in which acts are performed in an order different than illustrated, which may include performing some acts simultaneously, even though shown as sequential acts in illustrative examples.

Additionally, it should be appreciated that ranges disclosed herein may be exemplary, and include all ranges and subranges therein.

While certain variations are described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive variations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive variations described herein. It is, therefore, to be understood that the foregoing variations are presented by way of example only and that, within the scope of the appended claims and equivalents thereto; inventive variations may be practiced otherwise than as specifically described and claimed. Inventive variations of the present disclosure are directed to each individual feature and/or method described herein. In addition, any combination of two or more such features and/or methods, if such features and/or methods are not mutually inconsistent, is included within the inventive scope of the present disclosure.

What is claimed is:

1. A method for calibrating an automated cell processing system, comprising:
  coupling a calibration cartridge to an instrument within the automated cell processing system, wherein the instrument comprises a vision system and the calibration cartridge comprises one or more fiducial markers;
  detecting a location of each of the one or more fiducial markers using the vision system; and
  generating a calibration result for one or more modules of the calibration cartridge using the locations of each of the one or more fiducial markers, wherein the one or more modules of the calibration cartridge correspond to one or more modules of a cell processing cartridge configured to interface with the instrument to perform a cell processing operation.

2. The method of claim 1, wherein generating the calibration result comprises:
  determining a region of interest (ROI) defined by the locations of each of the one or more fiducial markers; and
  mapping the ROI onto a reference image.

3. The method of claim 1, wherein the calibration result comprises an alignment map defining alignment between the vision system of the instrument and the one or more fiducial markers of the calibration cartridge.

4. The method of claim 3 further comprising applying the alignment map to an output of each of one or more sensors of the vision system during an automated cell processing procedure.

5. The method of claim 4, wherein the output comprises one or more images of the calibration cartridge obtained by the vision system.

6. The method of claim 1, wherein the one or more modules comprises one or more of a bioreactor module, a magnetic cell separation (MCS) module, a centrifugal counterflow elutriation module, and a waste module.

7. The method of claim 6, wherein the bioreactor module comprises a bioreactor compartment, a mixing compartment, and one or more thermal compartments.

8. The method of claim 6, wherein the calibration result comprises a first calibration result and the one or more modules comprise the MCS module, the method further comprising:

detecting one or more features of the MCS module of the calibration cartridge using the vision system;

generating an MCS module map based on the one or more features that defines alignment between an actual position of the calibration cartridge and a desired position of the calibration cartridge; and applying the MCS module map to an output of the vision system during a cell processing procedure to align the vision system to the MCS module.

9. The method of claim 1, wherein each of the one or more modules comprises at least one fluid compartment configured to store a liquid therein.

10. The method of claim 1 further comprising coupling the cell processing cartridge to the instrument, wherein one or more cameras of the vision system are directed toward the one or more modules of the cell processing cartridge when the cell processing cartridge is coupled to the instrument.

11. The method of claim 1, wherein the calibration result comprises a first calibration result, the method further comprising:

detecting coordinates of a calibration image having a known dimension using the vision system; and generating a second calibration result using the coordinates of the calibration image.

12. The method of claim 11, wherein generating the second calibration result comprises mapping an output of the vision system to the coordinates of the calibration image.

13. The method of claim 12, wherein the second calibration result comprises a distortion map defining distortion of the calibration image from the coordinates of the output of the vision system.

14. The method of claim 13 further comprising applying the distortion map to the output of each of one or more sensors of the vision system during an automated cell processing procedure to compensate for the distortion.

15. The method of claim 12, wherein the output comprises a real-time image.

16. The method of claim 11 further comprising:

combining the first and second calibration results into a combined calibration result; and applying the combined calibration result to an output of the vision system during a cell processing procedure.

17. The method of claim 1, wherein the vision system comprises a plurality of cameras supported by the instrument.

18. The method of claim 17, wherein one or more of the plurality of cameras comprises a lens having a focal length of between about 8 mm and about 18 mm.

19. The method of claim 17, wherein one or more of the plurality of cameras comprises a lens having a focal length of between about 35 mm and about 50 mm.

20. The method of claim 1, wherein the automated cell processing system is calibrated during initial setup of the system.

21. The method of claim 1, wherein the instrument comprises a bioprocessing instrument or a sterile liquid transfer instrument.

22. The method of claim 1, wherein the calibration result is used to compensate for one or more of misalignment between the vision system and the calibration cartridge or distortion from the vision system.

\* \* \* \* \*